United States Patent
Bhatia et al.

(10) Patent No.: US 9,775,886 B2
(45) Date of Patent: *Oct. 3, 2017

(54) HUMAN PLACENTAL COLLAGEN COMPOSITIONS, AND METHODS OF MAKING AND USING THE SAME

(75) Inventors: Mohit Bhatia, Manalapan, NJ (US); Chris Lugo, Edison, NJ (US); Qian Ye, Livingston, NJ (US); James W. Edinger, Belford, NJ (US)

(73) Assignee: Celularity, Inc., Warren, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/610,375

(22) Filed: Sep. 11, 2012

(65) Prior Publication Data

US 2013/0071362 A1    Mar. 21, 2013

Related U.S. Application Data

(63) Continuation of application No. 13/467,736, filed on May 9, 2012, now Pat. No. 8,877,180, which is a continuation of application No. 13/212,661, filed on Aug. 18, 2011, now Pat. No. 8,821,857, which is a continuation of application No. 11/973,902, filed on Oct. 9, 2007.

(60) Provisional application No. 60/850,131, filed on Oct. 6, 2006.

(51) Int. Cl.
| | | |
|---|---|---|
| A61K 38/39 | (2006.01) | |
| C07K 14/78 | (2006.01) | |
| A61K 8/65 | (2006.01) | |
| A61Q 19/00 | (2006.01) | |
| A61Q 19/08 | (2006.01) | |

(52) U.S. Cl.
CPC ............ *A61K 38/39* (2013.01); *A61K 8/65* (2013.01); *A61Q 19/00* (2013.01); *A61Q 19/08* (2013.01); *C07K 14/78* (2013.01); *A61K 2800/92* (2013.01)

(58) Field of Classification Search
None
See application file for complete search history.

(56) References Cited

U.S. PATENT DOCUMENTS

| | | |
|---|---|---|
| 3,157,524 A | 11/1964 | Artandi |
| 3,800,792 A | 4/1974 | McKnight et al. |
| 4,060,081 A | 11/1977 | Yannas et al. |
| 4,320,201 A | 3/1982 | Berg et al. |
| 4,361,552 A | 11/1982 | Baur, Jr. |
| 4,420,339 A | 12/1983 | Kato |
| 4,599,226 A | 7/1986 | Fox, Jr. et al. |
| 4,704,131 A | 11/1987 | Noishiki et al. |
| 4,772,284 A | 9/1988 | Jefferies et al. |
| 4,837,285 A | 6/1989 | Berg et al. |
| 4,969,912 A * | 11/1990 | Kelman et al. ............ 128/898 |
| 4,973,493 A | 11/1990 | Guire |
| 5,028,695 A | 7/1991 | Eckmayer et al. |
| 5,036,056 A | 7/1991 | Kludas |
| 5,116,620 A | 5/1992 | Chvapil et al. |
| 5,141,747 A | 8/1992 | Scholz |
| 5,230,693 A | 7/1993 | Williams et al. |
| 5,308,889 A | 5/1994 | Rhee et al. |
| 5,428,022 A | 6/1995 | Palefsky et al. |
| 5,436,135 A | 7/1995 | Tayot |
| 5,486,359 A | 1/1996 | Caplan |
| 5,523,291 A | 6/1996 | Janzen et al. |
| 5,607,590 A | 3/1997 | Shimizu |
| 5,612,028 A | 3/1997 | Sackier et al. |
| 5,618,312 A | 4/1997 | Yui et al. |
| 5,635,517 A | 6/1997 | Muller |
| 5,639,796 A | 6/1997 | Lee |
| 5,656,478 A | 8/1997 | Tanagho et al. |
| 5,658,582 A | 8/1997 | Dorigatti et al. |
| 5,686,425 A | 11/1997 | Lee |
| 5,698,579 A | 12/1997 | Muller |
| 5,705,488 A | 1/1998 | Janzen et al. |
| 5,723,010 A | 3/1998 | Yui et al. |
| 5,739,113 A | 4/1998 | Lee |
| 5,763,399 A | 6/1998 | Lee |
| 5,798,368 A | 8/1998 | Muller |
| 5,814,328 A | 9/1998 | Gunasekaran |
| 5,830,548 A | 11/1998 | Andersen et al. |
| 5,837,278 A | 11/1998 | Geistlich et al. |
| 5,874,448 A | 2/1999 | Muller |
| 5,876,451 A | 3/1999 | Yui et al. |
| 5,877,200 A | 3/1999 | Muller |
| 5,916,266 A | 6/1999 | Yui et al. |
| 5,929,117 A | 7/1999 | Muller |

(Continued)

FOREIGN PATENT DOCUMENTS

| | | |
|---|---|---|
| DE | 2631909 | 7/1976 |
| EP | 214853 A2 | 3/1987 |

(Continued)

OTHER PUBLICATIONS

U.S. Appl. No. 11/893,409, filed Aug. 15, 2007, Liu et al.
U.S. Appl. No. 11/906,961, filed Oct. 3, 2007, Liu et al.
U.S. Appl. No. 11/973,125, filed Oct. 4, 2007, Liu et al.
Akle et al., 1981, "Immunogenicity of Human Amniotic Epithelial Cells After Transplantation Into Volunteers," The Lancet, 2: 1003-1005.

(Continued)

*Primary Examiner* — Maury Audet
(74) *Attorney, Agent, or Firm* — Celularity, Inc.; Thomas L. Smith

(57) ABSTRACT

The present invention provides compositions comprising human placental telopeptide collagen, methods of preparing the compositions, methods of their use and kits comprising the compositions. The compositions, kits and methods are useful, for example, for augmenting or replacing tissue of a mammal.

18 Claims, 4 Drawing Sheets

(56) References Cited

U.S. PATENT DOCUMENTS

Figure 1:
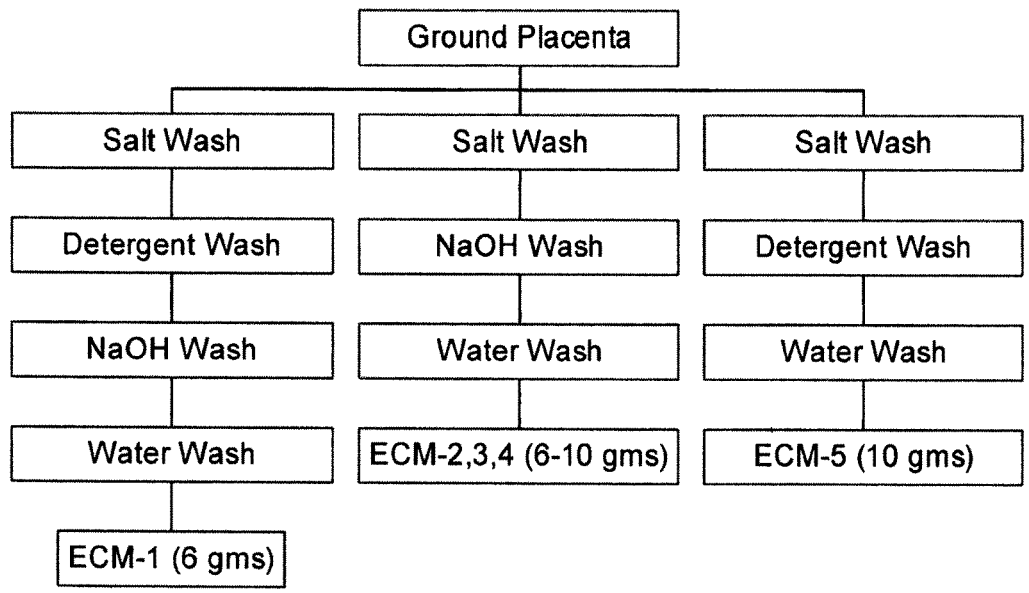

| | | |
|---|---|---|
| 5,932,205 A | 8/1999 | Wang et al. |
| 5,939,323 A | 8/1999 | Valentini et al. |
| 5,955,476 A | 9/1999 | Muller |
| 5,993,844 A | 11/1999 | Abraham et al. |
| 6,093,417 A | 7/2000 | Petrus |
| 6,113,932 A | 9/2000 | Hoath et al. |
| 6,124,259 A | 9/2000 | Delmage et al. |
| 6,143,315 A | 11/2000 | Wang et al. |
| 6,152,142 A | 11/2000 | Tseng |
| 6,165,489 A | 12/2000 | Berg et al. |
| 6,261,549 B1 | 7/2001 | Fernandez |
| 6,281,230 B1 | 8/2001 | Muller |
| 6,300,315 B1 | 10/2001 | Liu |
| 6,316,471 B1 | 11/2001 | Muller |
| 6,326,019 B1 | 12/2001 | Tseng |
| 6,335,349 B1 | 1/2002 | Muller |
| 6,371,992 B1 | 4/2002 | Tanagho et al. |
| 6,379,323 B1 | 4/2002 | Patterson |
| 6,380,239 B1 | 4/2002 | Muller |
| 6,387,367 B1 | 5/2002 | Davis-Sproul |
| 6,395,754 B1 | 5/2002 | Muller |
| 6,403,613 B1 | 6/2002 | Man |
| 6,417,166 B2 | 7/2002 | Liu |
| 6,428,802 B1 | 8/2002 | Atala |
| 6,432,710 B1 | 8/2002 | Boss et al. |
| 6,432,712 B1 | 8/2002 | Wolfinbarger, Jr. |
| 6,458,810 B1 | 10/2002 | Muller |
| 6,476,052 B1 | 11/2002 | Muller |
| 6,479,064 B1 | 11/2002 | Atala |
| 6,555,554 B2 | 4/2003 | Muller |
| 6,652,594 B2 | 11/2003 | Francis et al. |
| 6,734,018 B2 | 5/2004 | Wolfinbarger et al. |
| 6,753,181 B2 | 6/2004 | Atala |
| 6,866,686 B2 | 3/2005 | Ollerenshaw et al. |
| 6,933,103 B1* | 8/2005 | Klein et al. ............... 435/1.2 |
| 6,962,814 B2 | 11/2005 | Mitchell et al. |
| 7,045,148 B2 | 5/2006 | Hariri |
| 7,091,353 B2 | 8/2006 | Robarge |
| 7,121,999 B2* | 10/2006 | Abraham et al. ............. 600/36 |
| 8,877,180 B2* | 11/2014 | Bhatia .................. A61K 38/39 424/93.7 |
| 2001/0037014 A1 | 11/2001 | Liu |
| 2001/0038848 A1 | 11/2001 | Donda et al. |
| 2002/0090725 A1* | 7/2002 | Simpson et al. ............. 435/402 |
| 2002/0103542 A1 | 8/2002 | Bilbo |
| 2002/0151974 A1 | 10/2002 | Bonassar et al. |
| 2002/0197296 A1 | 12/2002 | Gen |
| 2003/0032179 A1 | 2/2003 | Hariri |
| 2003/0045552 A1 | 3/2003 | Robarge |
| 2003/0143207 A1 | 7/2003 | Livesey et al. |
| 2003/0180269 A1 | 9/2003 | Hariri |
| 2003/0187515 A1* | 10/2003 | Hariri et al. ............. 623/23.72 |
| 2003/0235909 A1 | 12/2003 | Hariri |
| 2004/0028660 A1 | 2/2004 | Hariri |
| 2004/0048796 A1* | 3/2004 | Hariri et al. ............. 514/12 |
| 2005/0096351 A1 | 5/2005 | Jaworsky |
| 2005/0271614 A1 | 12/2005 | Wolfinbarger |
| 2006/0084815 A1 | 4/2006 | Muller |
| 2007/0020225 A1* | 1/2007 | Abramson et al. ......... 424/78.27 |
| 2007/0021704 A1 | 1/2007 | Hariri et al. |
| 2007/0021762 A1 | 1/2007 | Liu et al. |
| 2007/0038298 A1 | 2/2007 | Sulner et al. |
| 2007/0202189 A1 | 8/2007 | Ahlfors |
| 2008/0044848 A1 | 2/2008 | Heidaran |

FOREIGN PATENT DOCUMENTS

| | | |
|---|---|---|
| EP | 0 330 389 A | 8/1989 |
| EP | 0399782 A2 | 11/1990 |
| EP | 526756 A1 | 2/1993 |
| EP | 637452 A1 | 2/1995 |
| EP | 734736 A1 | 10/1996 |
| EP | 773033 A1 | 5/1997 |
| EP | 781564 A2 | 7/1997 |
| EP | 1031356 A2 | 8/2000 |
| EP | 1103277 A1 | 5/2001 |
| FR | 2613620 A1 | 10/1988 |
| GB | 2360789 A | 10/2001 |
| JP | 62-268875 | 11/1987 |
| JP | 5056987 | 3/1993 |
| NL | 9101149 | 2/1993 |
| SU | 1286211 | 1/1987 |
| WO | WO 88/08305 A1 | 11/1988 |
| WO | WO 95/07095 A1 | 3/1995 |
| WO | WO 95/22301 A1 | 8/1995 |
| WO | WO 96/13974 A1 | 5/1996 |
| WO | WO 97/48405 A1 | 12/1997 |
| WO | WO 98/03502 A1 | 1/1998 |
| WO | WO 98/37903 A1 | 9/1998 |
| WO | WO 98/54170 A1 | 12/1998 |
| WO | WO 99/63051 A1 | 12/1999 |
| WO | WO 99/65427 A1 | 12/1999 |
| WO | WO 01/15750 A1 | 3/2001 |
| WO | WO 01/66162 A1 | 9/2001 |
| WO | WO 02/09647 A2 | 2/2002 |
| WO | WO 02/40630 A | 5/2002 |
| WO | WO 02/059106 A1 | 8/2002 |
| WO | WO 03/020297 A2 | 3/2003 |
| WO | WO 03/082201 A | 10/2003 |
| WO | WO 03/087333 A2 | 10/2003 |
| WO | WO 2006/095342 A | 9/2006 |

OTHER PUBLICATIONS

Allman, 2001, "Xenogenic Extracellular Matrix Grafts Elicit a TH2-Restricted Immune Response," Transplantation, 71(11):1631-1640.
Amenta et al., 1986, "The Extracellular Matrix is an Integrated Unit: Ultrastructural Localization of Collagen Types I, III, IV, V, VI, Fibronectin, and Laminin in Human Term Placenta," Coll. Relat. Res. 6(2):125-52.
Anderson et al., 2001, "Amniotic Membrane Transplantation After the Primary Surgical Management of Band Keratopathy," Cornea, 20(4):354-361.
Anderson et al., 2001, "Amniotic Membrane Transplantation for Partial Limbal Stem Cell Deficiency," British J. of Opthamology, 85:567-575.
Aplin et al., 1985, "The Extracellular Matrix of Human Amniotic Epithelium: Ultrastructure, Composition and Deposition," J. Cell Sci., 79:119-136.
Arora et al., 1994, "Controlled Comparison of Interceed and Amniotic Membrane Graft in the Prevention of Postoperative Adhesions in the Rabbit Uterine Horn Model," European Journal of Obstetrics Gynecology and Reproductive Biology, 55: 179-182.
Ashworth et al., 1986, "Vaginoplasty Using Amnion," Obstet. Gynecol., 67:443-446.
Atanassov et al., 1994, "Use of Amniotic Membranes As Biological Dressings in Contemporary Treatment of Burns," Ann. Medit. Burns Club, 7(4).
Atiyeh et al., 2002, "Management of Acute and Chronic Open Wounds: The Importance of Moist Environment in Optimal Wound Healing," Curr. Pharm. Biotechnol., 3:179-195.
Bachinger et al., 1990, "The Relationship of the Biophysical and Biochemical Characteristics of Type VII Collagen to the Function of Anchoring Fibrils," J. Biol. Chem., 265: 0095-10101.
Badawy et al., 1989, "Evaluation of Tissue Healing and Adhesion Formation After an Intraabdominal Amniotic Membrane Graft in the Rat," J. Reprod. Med., 34(3):198-202.
Badylak, 1999, "Endothelial Cell Adherence to Small Intestinal Submucosa: An Acellular Bioscaffold," Biomaterials, 20:2257-2263.
Badylak, 2002, "The Extracellular Matrix as a Scaffold for Tissue Reconstruction," Semin. Cell Dev. Biol., 13:377-383.
Bapat et al., 1974, "Preliminary Report on Acceleration of Wound Healing by Amnion Membrane Graft," Indian J. Med. Res., 62:1342-1346.
Bari et al., 2002, "Role of Human Foetal Membranes (Amniotic Membrane) in the Management of Burn Wounds," Annals of Burns and Fire Disasters, XV(4):1-8.

(56) References Cited

OTHER PUBLICATIONS

Barlas et al., 1992, "Human Amniotic Membrane As an Intestinal Patch for Neomucosal Growth in the Rabbit Model," J. Pediatr. Surg., 27(5):597-601.
Barton et al., 1997, "Amniotic Membrane Translplantation in Glaucoma Surgery," Investig. Opthalmology and Visual Science, Abstract Book, Part I: Annual Meeting, Ft. Lauderdale, Florida, May 11-16, 1997, 38(4):5473, Abstract 2194.
Bennett et al., 1980, "Treatment of Chronic Ulceration of the Legs With Human Amnion," Lancet, 1: 1153-1155.
Benque et al., 1997, "Combined Collagen Membrane and Hydroxyapatite/Collagen Chondroitin-Sulfate Spacer Placement in the Treatment of 2-Wall Intrabony Defects in Chronic Adult and Rapidly Progressive Periodontitis Patients," J. Clin. Periodontol., 24(8):550-556.
Black et al., 1994, "Comparative Study of Collagen and Expanded Polytetrafluoroethylene Membranes in the Treatment of Human Class II Furcation Defects," J. Periodontol., 65(6):598-604.
Bleggi-Torres et al., 1997, "Ultrastructural Study of the Neovagina Following the Utilization of Human Amniotic Membrane for Treatment of Congenital Absence of the Vagina," Brazilian Journal of Medical and Biological Research, 30: 861-864.
Blumenthal, 1993, "A Clinical Comparison of Collagen Membranes With E-PTFE Membranes in the Treatment of Human Mandibular Buccal Class II Furcation Defects," J. Periodontol., 64(10):925-933.
Boc et al., 1985, "Implications for the Use of Amnion and Chorion in Podiatric Medicine and Surgery," J. Foot Surg., 24(4):236-242.
Bose, 1979, "Burn Wound Dressing With Human Amniotic Membrane," Ann. R. Coll. Surg. Engl., 61:444-447.
Brito et al., 2003, "Effect of Topical Application of Fibronectin in Duodenal Wound Healing in Rats," Acta Cirurgica Brasileira, 18(2):97-101.
Bunyaratavej et al., 2001, "Collagen Membranes: A Review," J. Periodontol., 72(2):215-229.
Chang et al., 1994, "Frozen Preservation of Human Amnion and Its Use as a Burn Wound Dressing," Chang Gung Med. J., 17(4):316-324.
Chaplin et al., 1999, "Use of an Acellular Dermal Allograft for Dural Replacement: An Experimental Study," Neurosurgery, 45(2):320-327.
Chen et al., 1999, "Acellular Collagen Matrix as a Possible 'Off the Shelf' Biomaterial for Urethral Repair," Urology, 54(3):407-410.
Cheng et al., 1988, "Fibronectin Enhances Healing of Excised Wounds in Rats," Arch. Dermatol., 124:221-225.
Chung, et al., 1990, "Clinical Evaluation of a Biodegradable Collagen Membrane in Guided Tissue Regeneration," J. Periodontol., 61(12):732-736.
Chvapil et al., 1973, "Medical and Surgical Applications of Collagen," Int. Rev. Connect. Tissue Res., 6:1-61.
Colocho et al., 1974, "Human Amniotic Membrane as a Physiologic Wound Dressing," Arch. Surg., 109: 370-373.
Constantino et al., 2000, "Human Dural Replacement With Acellular Dermis: Clinical Results and A Review of the Literature," Head & Neck, 22:765-771.
Davis et al., 1987, "Human Amnion Membrane Serves as a Substratum for Growing Axons In Vitro and In Vivo," Science, 236:1106-1109.
De Rotth, 1940, "Plastic Repair of Conjunctival Defects With Fetal Membranes," Arch. of Opthalm., 23(3):522-525.
Delustro et al., 1987, "Reaction to Injectable Collagen: Results in Animal Models and Clinical Use," Plast. Reconstr. Surg., 79(4):581-594.
Delustro et al.,1990, "Immune Responses to Allogeneic and Xenogeneic Implants of Collagen and Collagen Derivatives," Clin. Orthop., 260:263-279.
Demirkan et al., 2002, "The Use of Amniotic Membrane in Flexor Tendon Repair: An Experimental Model," Arch. Orthop. Trauma Surg., 122:396-399.
Dhall, 1984, "Amnion Graft for Treatment of Congenital Absence of the Vagina," Br. J. Obstet. Gynaecol., 91:279-282.

Dino et al., 1966, "Human Amnion: The Establishment of an Amnion Bank and Its Practical Applications in Surgery," J. Philipp. Med. Assoc., 42(7):357-366.
Dong et al., 2002, "Some New Aspects in Biosensors," Reviews in Mol. Biotechnol., 82:303-323.
Dua et al., 1999, "Amniotic Membrane Transplantation," Br. J. Opthalmol., 83:748-752.
Eade, 1958, "The Relationship Between Granulation Tissue, Bacteria, and Skin Grafts in Burned Patients," Plast. Reconstr. Surg., 22(1):42-55.
Eckes et al., 2000, "Fibroblast-Matrix Interactions in Wound Healing and Fibrosis," Matrix Biol., 19:325-332.
Eldad et al., 1977, "Amniotic Membranes as a Biological Dressing," S. Afr. Med. J., 51(9):272-275.
Erdener et al., 1992, "Amniotic Membrane Wrapping: An Alternative Method to the Splenorrhaphy in the Injured Spleen," Eur. J. Pediatr. Surg., 2:26-28.
Faulk et al., 1980, "Human Amnion as an Adjunct in Wound Healing," Lancet, 1:1156-1158.
Flageul et al., 1994, "Le Collagène injectable: bilan après 10 ans d'utilisation en complément de las chirurgie esthétique," Annales de Chirurgie Plastique Esthétique, 39(6):765-771.
Fletcher, 2000, "The Role of Collagen in Wound Healing," Prof. Nurse, 15(8):527-530.
Friess, 1998, "Collagen—Biomaterial for Drug Delivery," Eur. J. Pharm. Biopharm., 45(2):113-136.
Fujisato et al., 1999, "Cross-Linking of Amniotic Membranes," J. Biomater. Sci. Polym. Ed., 10:1171-1181.
Gamba et al., 2000, "Experimental Abdominal Wall Defect Repaired With Acellular Matrix," Pediatr. Surg. Int., 18:327-331.
Ganatra et al., 1996, "Method of Obtaining and Preparation of Fresh Human Amniotic Membrane for Clinical Use," J. Pak. Med. Assoc., 46(6):126-128.
Gebhardt et al., 1995, "Collagen as a Delivery System for Hydrophobic Drugs: Studies With Cyclosporine," J. Ocul. Pharmacol. Ther., 11(3):319-327.
Ghalambor et al., 2000, "The Amniotic Membrane: A Suitable Biological Dressing to Prevent Infection in Thermal Burns," Medical Journal of Islamic Academy of Sciences, 13(3):115-118.
Gharib et al., 1996, "Use of Amniotic Graft in the Repair of Gastroschisis," Pediatr. Surg. Int., 11:96-99.
Goepfert, 1991, "Collagen Injections," Arch. Otolaryngol. Head Neck Surg., 117(10):1189.
Gomes et al., 1996, "Effects of Human Amniotic Membrane on Dental Socket Wound Healing Process in Rats," Journal of Dental Research, 75(5):1114, Abstract 290.
Gomes et al., 2001, "Histologic Evaluation of the Osteoinductive Property of Autogenous Demineralized Dentin Matrix on Surgical Bone Defects in Rabbit Skulls Using Human Amniotic Membrane for Guided Bone Regeneration," International Journal of Oral & Maxillofacial Implants, 16(4):563-571.
Gomes et al., 2003, "Amniotic Membrane Transplantation for Partial and Total Limbal Stem Cell Deficiency Secondary to Chemical Burn," Opthamology, 110(3):466-473.
Graham, Med. Device Tech., 9(1):18-22 (1998).
Gris et al., 2002, "Amniotic Membrane Implantation as a Therapeutic Contact Lens for the Treatment of Epithelial Disorders," Cornea, 21(1):22-27.
Gris et al., 2002, "Histologic Findings after Amniotic Membrane Graft in the Human Cornea," Opthamology, 109(3):508-512.
Gruss et al., 1978, "Human Amniotic Membrane: A Versatile Wound Dressing," Can. Med. Assoc. J., 118:1237-1240 & 1245-1246.
Guler, et al., 1993, "A Comparative Histopathological Investigation of the Effect of Lyophilized Amniotic Membrane on Wound Healing as an Allograft Material in Rats," Journal of Islamic Academy of Sciences, 6(3), pp. 1-17.
Haberal et al., 1987, "The Use of Silver Nitrate-Incorporated Amniotic Membrane as a Temporary Dressing," Burns, 13(2):159-163.
Hammer et al., 1997, "Amnion Epithelial Cells, In Contrast to Trophoblast Cells, Express All Classical HLA Class I Molecules Together With HLA-G," Am. J. Reprod. Immunol., 37:161-171.

(56) References Cited

OTHER PUBLICATIONS

Heiligenhaus et al., 2001, "Improvement of HSV-1 Necrotizing Keratitis With Amniotic Membrane Transplantation," Investigative Opthamology and Visual Science, 42(9):1969-1974.
Hennink et al., 2002, "Novel Crosslinking Methods to Design Hydrogels," Advanced Drug Delivery Reviews, 54:13-36.
Herne et al., 2000, "New Facial Rejuvenation Techniques," Semin. Cutan. Med. Surg., 19(4):221-231.
Hodde, 2002, "Naturally Occurring Scaffolds for Soft Tissue Repair and Regeneration," Tissue Eng., 8(2):295-308.
Honovar et al., 2000, "Amniotic Membrane Transplantation for Ocular Surface Reconstruction in Stevens-Johnson Syndrome," Opthamology, 107(5):975-979.
John et al., 2002, "Amniotic Membrane in the Surgical Management of Acute Toxic Epidermal Necrolysis," Ophthalmology, 109(2):351-360.
John, 2003, "Human Amniotic Membrane Transplantation: Past, Present, and Future," Ophthalmol. Clin. North Am., 16:43-64.
Johnson, 1937, "Insulating Patches and Absorbable Sutures Made From Fetal Membranes," New England Journal of Medicine, 216(22):978-982.
Kakishita et al., 2000, "Human Amniotic Epithelial Cells Produce Dopamine and Survive After Implantation Into the Striatum of a Rat Model of Parkinson's Disease: A Potential Source of Donor for Transplantation Therapy," Exp. Neurol., 165(1):27-34.
Kane et al., 1996, "7.10 Burn Dressings," Biomaterials Science: An Introduction to Materials in Medicine, 360-370.
Kassouf et al., 2001, "Collagen Injection for Treatment of Urinary Incontinence in Children," J. Urol., 165(5):1666-1668.
Kershen et al., 2002, "Beyond Collagen: Injectable Therapies for the Treatment of Female Stress Urinary Incontinence in the New Millennium," Urol. Clin. North Am., 29(3):559-574.
Kim et al., 1995, "Transplantation of Preserved Human Amniotic Membrane for Surface Reconstruction in Severely Damaged Rabbit Corneas," Cornea, 14(5):473-484.
Kim et al., 2000, "Amniotic Membrane Patching Promotes Healing and Inhibits Proteinase Activity on Wound Healing Following Acute Corneal Alkali Burn," Experimental Eye Research, 70: 329-337.
Kirschbaum et al., 1963, "Use of Amnion in Extensive Burns," Third International Congress of Plastic Surgery, Washington, D.C., Oct. 13-18, 1963, Abstracts of Papers, p. 21, Abstract 33.
Klein, 2001, "Skin Filling. Collagen and Other Injectables of the Skin," Dermatol. Clin., 19(3):491-508.
Klen et al., 1976, "Influence of Ionizing Sterilization on the Permeability of Human Chorio-Amniotic, Dermo-Epidermal and Fascial Grafts," Res. Exp. Med., 167(1):15-21.
Koizumi et al., 2000, "Cultivation of Corneal Epithelial Cells on Intact and Denuded Human Amniotic Membrane," Investigative Opthamology and Visual Science, 41(9):2506-2513.
Koizumi et al., 2000, "Growth Factor mRNA and Protein in Preserved Human Amniotic Membrane," Current Eye Research, 20(3): 173-177.
Kubo et al., 2001, "Immunogenicity of Human Amniotic Membrane in Experimental Xenotransplantation," Invest. Ophthalmol. Vis. Sci., 42(7):1539-1546.
Kucan et al., 1982, "Amniotic Membranes as Dressings Following Facial Dermabrasion," Ann. Plast. Surg., 8(6):523-527.
Lee et al., 1996, "Effect of Amniotic Fluid in Corneal Sensitivity and Nerve Regeneration After Excimer Laser Ablation," Cornea, 15(5):517-524.
Lee et al., 1997, "Amniotic Membrane Transplantation for Persistent Epithelial Defects With Ulceration," Am. J. Opthalm., 123(3):303-312.
Lee et al., 1998, "Mesothelial Cell Regeneration in Purified Human Amnion Membrane Grafts Implanted in Dog Pericardium," Tissue Engineering, 4(2):131-141.
Lee et al., 2001, "Biomedical Applications of Collagen," Int. J. Pharm., 221:1-22.
Lee et al., 2002, "Laminin Modified Infection-Preventing Collagen Membrane Containing Silver Sulfadiazine-Hyaluronan Microparticles," Artif. Organs, 26(6):521-528.
Lightner, 2002, "Review of the Available Urethral Bulking Agents," Curr. Opin. Urol., 12(4):333-338.
Mantovani et al., 2002, "Reconstructive Urethroplasty Using Porcine Acellular Matrix: Preliminary Results," $59^{th}$ Convegno Associazione Urologi Lombardi—Milano, 26 Gennaio 2002, pp. 127-128 (Abstract in English).
Marzaro et al., 2002, "Autologous Satellite Cell Seeding Improves In Vivo Biocompatibility of Homologous Muscle Acellular Matrix Implants," International J. Mol. Med., 10:177-182.
Massee et al., 1962, "Use of Fetal Membranes as Replacement for Pelvic Peritoneum After Pelvic Exenteration in the Dog," Surg. Forum, 13:407-408.
Mattson et al., 1995, "Treatment of Intrabony Defects With Collagen Membrane Barriers," J. Periodontol., 66(7):635-645.
Mattson et al., 1999, "The Use of 2 Bioabsorbable Barrier Membranes in the Treatment of Interproximal Intrabony Periodontal Defects," J. Periodontol., 70(5):510-517.
McIndoe et al., 1938, "An Operation for the Cure of Congenital Absence of the Vagina," Journal of Obstetrics and Gynaecology, 490-494.
McPherson et al., 1986, "An Examination of the Biologic Response to Injectable Glutaraldehyde Cross Linked Collagen Implants," J. Biomed. Mater. Res., 20:93-107.
McPherson, 1992, "The Utility of Collagen-Based Vehicles in Delivery of Growth Factors for Hard and Soft Tissue Wound Repair," Clin. Mater., 9:225-234.
Meinert et al., 2001, "Proteoglycans and Hyaluronan in Human Fetal Membranes," Am. J. Obstet. Gynecol., 184(4): 679-685.
Meller et al., 2000, "Amniotic Membrane Transplantation for Symptomatic Conjunctivochalasis Refractory to Medical Treatments," Cornea, 19(6):796-803.
Meller et al., 2000, "Amniotic Membrane Transplantation for Acute Chemical or Thermal Burns," Opthamology, 107(5):980-989.
Merguerian et al., 2000, "Acellular Bladder Matrix Allografts in the Regeneration of Functional Bladders: Evaluation of Large-Segment (>24 $cm^2$) Substitution in a Porcine Model," BJU Intl., 85:894-898.
Mligiliche et al., 2002, "Extracellular Matrix of Human Amnion Manufactured Into Tubes as Conduits for Peripheral Nerve Regeneration," J. Biomed. Mater. Res., 63:591-600.
Morton et al., 1986, "Human Amnion in the Treatment of Vaginal Malformations," Br. J. Obstet. Gynaecol., 93:50-54.
Muralidharan et al., 1991, "A New Biological Membrane for Pericardial Closure," J. Biomed. Mater. Res., 25:1201-1209.
Murata et al., 1998, "Human Amniotic Membrane on Guided Bone Regeneration in Skull Defects," Journal of Dental Research, 77:840, Abstract 1668.
Nguyen et al., 2002, "Photopolymerizable Hydrogels for Tissue Engineering Applications," Biomaterials, 23(22):4307-4314.
Nisolle et al., 1992, "Vaginoplasty Using Amniotic Membranes in Cases of Vaginal Agenesis or After Vaginectomy," J. Gynecol. Surg., 8:25-30.
Oremus et al., 2002, "A Survey of Physician Efficacy Requirements to Plan Clinical Trials," Pharmacoepidemiology Drug Saf., 11(8):677-685.
Ozcan et al., 1997, "Combined Use of Root Conditioning, Fibrin-Fibronectin System and a Collagen Membrane to Treat a Localized Gingival Recession: A 10-Case Report," J. Marmara Univ. Dent. Fa., 2(4):588-598.
Ozeren et al., 1998, "The Effects of Human Amniotic Membrane and Fibrin Sealant in the Prevention of Postoperative Adhesion Formation in the Rabbit Ovary Model," Australian & New Zealand Journal of Obstetrics & Gynaecology, 38(2):207-209.
Pannek et al., 2001, "Particle Migration After Transurethral Injection of Carbon Coated Beads for Stress Urinary Incontinence," J. Urol., 166(4):1350-1353.
Parnigotto et al., 2000, "Experimental Defect in Rabbit Urethra Repaired with Acellular Aortic Matrix," Urol. Res., 28:46-51.
Patino et al., 2002, "Collagen as an Implantable Material in Medicine and Dentistry", J. Oral Implantol., 28(5):220-225.

(56) References Cited

OTHER PUBLICATIONS

Paul et al., 1992, "Use of a Collagen Barrier to Enhance Healing in Human Periodontal Furcation Defects," Int. J. Periodontics Restorative Dent., 12(2):123-131.
Paul et al., 2003, "Chemical Stabilisation of Collagen as a Biomimetic," The Scientific World, 3:138-155.
Peppas et al., 2000, "Hydrogels in Pharmaceutical Formulations," Eur. J. Pharm. Biopharm., 50(1):27-46.
Piazza et al., 1992, "Neovaginoplasty With McInndoe Technic and Use of Amniotic Membrane: Study With 15 Patients," Rev. Bras. Ginecol. Obstet., 14:224-226.
Pigeon, 1960, "Treatment of Second-Degree Burns with Amniotic Membranes," Can. Med. Assoc. J., 83:844-845.
Pires et al., 1999, "Amniotic Membrane Transplantation for Symptomatic Bullous Keratopathy," Archives of Opthamology, 117:1291-1297.
Power et al., 1995, "Analysis of the Acute Ophthalmic Manifestations of the Erythema Multiforme/Stevens-Johnson Syndrome/Toxic Epidermal Necrolysis Disease Spectrum," Ophthalmology, 102(11):1669-1676.
Prabhasawat et al., 1997, "Comparison of Conjunctival Autografts, Amniotic Membrane Grafts, and Primary Closure for Pterygium Excision," Ophthalmology, 104(6):974-985.
Prabhasawat et al., 1997, "Impression Cytology Study of Epithelial Phenotype of Ocular Surface Reconstructed by Preserved Human Amniotic Membrane," Arch. Ophthalmol., 115(11):1360-1367.
Prasad et al., 1986, "Use of Amnion for the Treatment of Stevens-Johnson Syndrome," J. Trauma, 26(10):945-946.
Prathiba et al., 2000, "Cutaneous Wound Healing: Significance of Proteoglycans in Scar Formation," Current Science, 78(6):1-5.
Quinby et al., 1982, "Clinical Trials of Amniotic Membranes in Burn Wound Care," Plast. Reconstr. Surg., 70:711-717.
Quteish et al., 1992, "The Use of Irradiated-Crosslinked Human Collagen Membrane in Guided Tissue Regeneration," J. Clin. Periodontol., 19(7):476-484.
Ramakrishnan et al., 1983, "Human Amniotic Membrane as a Temporary Biologic Dressing in Complicated Burns in a Developing Country," Journal of Burn Care & Rehabilitation, 4(3):202-204.
Rao et al., 1981, "Use of Dry Human and Bovine Amnion As a Biological Dressing," Arch. Surg., 116:891-896.
Rao, 1995, "Recent Developments of Collagen-Based Materials for Medical Applications and Drug Delivery Systems," J. Biomater. Sci. Polym. Ed., 7(7):623-645.
Reddy et al., 2000, "Regeneration of Functional Bladder Substitutes Using Large Segment Acellular Matrix Allografts in a Porcine Model," J. Urol., 164:936-941.
Rennekampff et al., 1994, "Evaluation of Amniotic Membrane as Adhesion Prophylaxis in a Novel Surgical Gastroschisis Model," J. Invest. Surg., 7:187-193.
Rigal-Sastourne et al., 2002, "Brulures Corneennes Et Metalloproteases: Influence Des Greffes De Membranes Amniotiques," J. Fr. Ophtalmol., 25:685-693.
Robson et al., 1973, "Amniotic Membranes as a Temporary Wound Dressing," Surg. Gynecol. Obstet., 136: 904-906.
Robson et al., 1973, "Quantitative Comparison of Biological Dressings," J. Surg. Res., 14: 431-434.
Robson et al., 1973, "The Effect of Human Amniotic Membranes on the Bacteria Population of Infected Rat Burns," Ann. Surg., 177(2):144-149.
Robson et al., 1974, "Clinical Experiences With Amniotic Membranes as a Temporary Biologic Dressing," Conn. Med., 38(9):449-451.
Sabella, 1913, "Use of Fetal Membranes in Skin Grafting," Med. Records NY, 83:478-480.
Sakuragawa et al., 1992, "Amniotic Tissue Transplantation: Clinical and Biochemical Evaluations for Some Lysosomal Storage Diseases," Brain Dev., 14(1):7-11.
Salisbury et al., 1980, "Comparison of the Bacterial Clearing Effects of Different Biologic Dressings on Granulating Wounds Following Thermal Injury," Plast. Reconstr. Surg., 66(4):596-598.

Sawhney, 1989, "Amniotic Membrane as a Biological Dressing in the Management of Burns," Burns, 15(5):339-342.
Schiff et al., 2003, "Towards a Sutureless Vasovasostomy: Use of Biomaterials and Surgical Sealants in a Rodent Vasovasostomy Model," Fertility and Sterility, 80(Suppl. 3): S92, Abstract O-240.
Schmedlen et al., 2002, "Photocrosslinkable Polyvinyl Alcohol Hydrogels that can be Modified with Cell Adhesion Peptides for use in Tissue Engineering," Biomaterials, 23:4325-4332.
Shieh et al., 1997,"Development and Clinical Evaluation of a Root Coverage Procedure Using a Collagen Barrier Membrane," J. Periodontol., 68(8):770-778.
Shimazaki et al., 1997, "Amniotic Membrane Transplantation for Ocular Surface Reconstruction in Patients With Chemical and Thermal Burns," Opthamology, 104(12):2068-2076.
Shimazaki et al., 2000, "Association of Preoperative Tear Function With Surgical Outcome in Severe Stevens-Johnson Syndrome," Ophthalmology, 107(8):1518-1523.
Shimazaki et al., 2002, "Transplantation of Human Limbal Epithelium Cultivated on Amniotic Membrane for the Treatment of Severe Ocular Surface Disorders," Opthamology, 109(7):1285-1290.
Shun et al., 1983, "Human Amnion in the Treatment of Chronic Ulceration of the Legs," Med. J. Aust., 2:279-283.
Silverton et al., 1979, "The Use of Amniotic Membrane in Acute Massive Full-Thickness Loss of the Abdominal Wall From Clostridial Myonecrosis," Ann. Plast. Surg., 3(6):558-566.
Singh et al., 2003, "Properties of Air Dried Radiation Processed Amniotic Membranes Under Different Storage Conditions," Cell and Tissue Banking, 4:95-100.
Skelhorne et al., 2002, "Hydrogel Adhesives for Wound-Care Applications," Med. Device Tech., 13(9):19-20 & 22-23.
Solomon et al., 2002, "Amniotic Membrane Grafts for Nontraumatic Corneal Perforations, Descemetoceles, and Deep Ulcers," Opthamology, 109(4):694-703.
Sorsby et al., 1946, "Amniotic Membrane Grafts in Caustic Burns of the Eye," Br. J. Opthamlol., 30:337-345.
Spira et al., 1994, "Human Amnion Collagen for Soft Tissue Augmentation—Biochemical Characterizations and Animal Observations," J. Biomed. Mat. Res., 28:91-96.
Stern, 1913, "The Grafting of Preserved Amniotic Membrane to Burned and Ulcerated Surfaces, Substituting Skin Grafts: A Preliminary Report," Journal of the American Medical Association, LX(13):973-974.
Subrahmanyam, 1995, "Amniotic Membrane as a Cover for Microskin Grafts," British Journal of Plastic Surgery, 48:477-478.
Szabo et al., 2000, "Evaluation of Seprafilm and Amniotic Membrane as Adhesion Prophylaxis in Mesh Repair of Abdominal Wall Hernia in Rats," European Surgical Research, 32:125-128.
Talmi et al., 1990, "Use of Human Amniotic Membrane as a Biologic Dressing," European Journal of Plastic Surgery, 13:160-162.
Talmi et al., 1991, "Antibacterial Properties of Human Amniotic Membranes," Placenta, 12:285-288.
Tancer et al., 1979, "Vaginal Epithelialization with Human Amnion," Obstet. Gynecol., 54(3):345-349.
Ti et al., 2001, "Amniotic Membrane Transplantation in Entropion Surgery," Opthamology, 108(7):1209-1217.
Trelford et al., 1972, "Amnion Autografts and Allografts as a Cover for Skin Defects in Sheep," J. Med., 3:81-87.
Trelford et al., 1972, "Considerations of the Amnion as an Autograft and as an Allograft in Sheep," J. Med., 3:231-241.
Trelford et al., 1973, "The Feasibility of Making an Artificial Vagina at the Time of Anterior Exenteration," Oncology, 28:398-401.
Trelford et al., 1975, "Amnion Autografts, Permanent Structure," J. Med., 6(3&4):243-247.
Trelford et al., 1973, "Amniotic Membrane AS a Living Surgical Dressing in Human Patients," Oncology, 28:358-364.
Trelford et al., 1975, "Implanted Amniotic Membrane as an Autograft and as an Allograft," J. Med., 6(2):169-180.
Trelford-Sauder et al., 1977, "Replacement of the Peritoneum With Amnion Following Pelvic Exenteration," Surg. Gynecol. Obstet., 145:699-701.
Trelford et al., 1979, "The Amnion in Surgery, Past and Present," Am. J. Obstet. Gynecol., 134(7):833-845.

(56) References Cited

OTHER PUBLICATIONS

Troensagaard-Hansen et al., 1950, "Amniotic Grafts in Chronic Skin Ulceration," Lancet, 1:859-860.
Tseng et al., 1997, "Amniotic Membrane Transplantation for Conjunctival Surface Reconstruction," Am. J. Ophthalmol., 124(6):765-774.
Tseng et al., 1998, "Amniotic Membrane Transplantation With or Without Limbal Allografts for Corneal Sufrace Reconstruction in Patients With Limabal Stem Cell Deficiency," Archives of Opthamology, 116:431-441.
Tseng, 2001, "Amniotic Membrane Transplantation for Ocular Surface Reconstruction," Biosci. Rep., 21(4):481-489.
Tsubota et al., 1996, "Surgical Reconstruction of the Ocular Surface in Advanced Ocular Cicatricial Pemphigoid and Stevens-Johnson Syndrome," Am. J. Ophthalmol., 122(1):38-52.
Ueta et al., 2002, "Immunosuppressive Properties of Human Amniotic Membrane for Mixed Lymphocyte Reaction," Clinical and Experimental Immunology, 129: 464-470.
Voytik-Harbin et al., 1997, "Identification of Extractable Growth Factors From Small Intestinal Submucosa," J. Cell Biochem., 67:478-491.
Wagshall et al., 2002, "Acellular Dermal Matrix Allograft in the Treatment of Muciogingival Defects in Children: Illustrative Case Report," J. Dentistry for Children, 79:39-43.
Walker et al., 1977, "Use of Fresh Amnion as a Burn Dressing," J. Pediatr. Surg., 12(3):391-395.
Wallace et al., 1988, "Injectable Collagen for Tissue Augmentation," Collagen vol. III Biotechnology, Chapter 5, 117-144.
Wang et al., 1994, "Evaluation of an Absorbable Collagen Membrane in Treating Class II Furcation Defects," J. Periodontol., 65(11):1029-1036.
Wang et al., 1997, "Corneal Haze is Reduced by Amniotic Membrane Matrix in Excimer Laser Photoablation in Rabbits," Investig. Opthalmology and Visual Science Abstract Book Part I, Annual Meeting, Ft. Lauderdale, Florida May 11-16, 1997, 38(4):5405, Abstract 1908-B701.
Wang et al., 1999, "Clinical Comparison of Two Techniques for Treatment of Gingival Recession," J. Dent. Res., 78 (IADR Abstracts):119, Abstract 106.
Ward et al., 1984, "The Long Term Results of the Use of Human Amnion in the Treatment of Leg Ulcers," British Journal of Plastic Surgery, 37: 191-193.
Ward et al., 1989, "The Healing of Chronic Venous Leg Ulcers With Prepared Human Amnion," Br. J. Plast. Surg., 42:463-467.
Wefer et al., 2002, "Homologous Acellular Matrix Graft for Vaginal Repair in Rats: A Pilot Study for a New Reconstructive Approach," World J. Urol., 20:260-263.
Yannas et al., 1980, "Design of an Artificial Skin: Control of Chemical Composition," J. of Biomed. Mat. Res., 14:107-132.
Yarborough et al., 1991, "Collagen Injections. A Case Study in the Erosion of the Medical Profession," Arch. Otolaryngol. Head Neck Surg., 117(1):270-272.
Young et al., 1991, "The Use of an Amniotic Membrane Graft to Prevent Postoperative Adhesions," Fertil. Steril., 55(3): 624-628.
Yukna et al., 1996, "Multi-Center Evaluation of Bioabsorbable Collagen Membrane for Guided Tissue Regeneration in Human Class II Furcations," J. Periodontol., 67(7):650-657.
Zahedi et al., 1998, "A 2-Year Clinical Evaluation of a Diphenylphosphorylazide-Cross-Linked Collagen Membrane for the Treatment of Buccal Gingival Recession," J. Periodontol., 69(9):975-981.
Zeeman et al., 1999, "Crosslinking and Modification of Dermal Sheep Collagen Using 1,4-butanediol diglycidyl ether," J. Biomed. Mater. Res., 46:424-433.
Zimmermann et al., 2000, "Hydrogel-Based Non-Autologous Cell and Tissue Therapy," BioTechniques, 29(3):564-572, 574, 576-581.
International Search Report and Written Opinion for PCT/US2007/021677, dated Sep. 11, 2008.
Office Action issued in U.S. Appl. No. 11/973,902 on Oct. 7, 2010.
Office Action issued in U.S. Appl. No. 11/973,902 on Jun. 23, 2011.
Office Action issued in U.S. Appl. No. 11/973,902 on Sep. 15, 2011.
Office Action issued in U.S. Appl. No. 11/973,902 on Apr. 10, 2012.
Office Action issued in U.S. Appl. No. 11/973,902 on Oct. 5, 2012.
Office Action issued in U.S. Appl. No. 13/212,661 on Jul. 17, 2012.
Office Action issued in U.S. Appl. No. 13/212,661 on Oct. 25, 2012.
Office Action issued in U.S. Appl. No. 13/467,736 on Jun. 25, 2012.
Office Action issued in U.S. Appl. No. 13/467,736 on Oct. 25, 2012.

* cited by examiner

HUMAN PLACENTAL COLLAGEN COMPOSITIONS, AND METHODS OF MAKING AND USING THE SAME

1. PRIOR RELATED APPLICATION

This application is a continuation of U.S. patent application Ser. No. 13/467,736, filed May 9, 2012, which is a continuation of U.S. patent application Ser. No. 13/212,661, filed Aug. 18, 2011, which is a continuation of U.S. patent application Ser. No. 11/973,902, filed Oct. 9, 2007, which claims the benefit under 35 U.S.C. §119(e) of U.S. Provisional Patent Application No. 60/850,131, filed Oct. 6, 2006, each of which is incorporated herein by reference in its entirety.

2. FIELD OF THE INVENTION

The present invention relates to compositions comprising collagen, e.g., human placental collagen, methods of preparing the compositions and methods of their use.

3. BACKGROUND OF THE INVENTION

Collagen is a protein that forms many structures in the body including tendons, bones, teeth and sheets that support skin and internal organs. Collagen is composed of three chains, wound in a triple helix. The structure comes from repeats of three amino acids. In the helices, every third amino acid is glycine, and many of the remaining amino acids are proline or hydroxyproline.

Collagen has been used commercially and clinically for some time. Currently, collagen can be used to replace or augment hard or soft connective tissue, such as skin, tendons, cartilage, bone and interstitium. Solid collagen has been implanted surgically, and injectable collagen formulations are now available for more convenient administration. Currently, several injectable collagen compositions are available commercially including ZYDERM®, ZYPLAST® COSMODERM® and COSMOPLAST®.

Each collagen composition has particular physical properties that can be advantageous or disadvantageous to its use in particular techniques. There thus remains a need in the art for collagen compositions with further physical properties to expand the selection of compositions available to practitioners of skill in the art.

4. SUMMARY OF THE INVENTION

The present invention is based, in part, on the discovery of collagen compositions that are useful, for example, for augmenting or replacing tissue of a mammal. In certain embodiments, the collagen compositions are prepared with substantially high yield of collagen from a source tissue. In certain embodiments, collagen compositions of the invention show reduced contamination, e.g. contamination by cellular and/or other protein contaminants. In certain embodiments of the invention, collagen compositions of the invention show advantageously low toxicity. In certain embodiments of the invention, the collagen compositions provide an advantageous source for the preparation of telopeptide collagen compositions.

In one aspect, provided herein are compositions comprising base-treated, detergent-treated telopeptide collagen. It has been discovered that such compositions can be readily prepared from relatively few steps, even starting with mammalian tissue as a source. Certain compositions provided herein are substantially free of cellular debris, subcellular debris and/or contaminating proteins such as fibronectin, laminin, cytokines and growth factors. Certain compositions provided herein comprise a high collagen content. In certain embodiments, the compositions comprise at least 90% collagen, when compared to the total amount of protein in the composition. In certain other embodiments, the collagen composition substantially lacks laminin and/or fibronectin (e.g., the composition comprises less than 1% laminin and/or fibronectin each by dry weight, or lacks detectable fibronectin and/or laminin).

In another aspect, the invention provides a collagen composition of the invention, e.g., base-treated, detergent-treated telopeptide collagen, comprising a plurality of stem cells. In various embodiments, the stem cells are embryonic stem cells, embryonic germ cells, mesenchymal stem cells, bone marrow-derived stem cells, hematopoietic progenitor cells (e.g., hematopoietic stem cells from peripheral blood, fetal blood, placental blood, umbilical cord blood, placental perfusate, etc.), somatic stem cells, neural stem cells, hepatic stem cells, pancreatic stem cells, endothelial stem cells, cardiac stem cells, muscle stem cells, adipose stem cells, and the like.

In a more specific embodiment, the stem cells are placental stem cells. In a more specific embodiment, said placental stem cells are $CD34^-$ and/or $CD200^+$. The placental stem cells can express CD10, CD73, CD105, CD200, HLA-G, and/or OCT-4, and lack expression of CD34, CD38, or CD45. The placental stem cells can also express HLA-ABC (MHC-1) and HLA-DR. In another specific embodiment, the stem cells that can be combined with the compositions of the invention are $CD200^+$ or $HLA-G^+$. In another specific embodiment, the placental stem cells are $CD73^+$, $CD105^+$, and $CD200^+$. In another specific embodiment, the placental stem cell that is $CD200^+$ and $OCT-4^+$. In another specific embodiment, the placental stem cells are $CD73^+$, $CD105^+$ and $HLA-G^+$. In another specific embodiment, the placental stem cells are $CD73^+$ and $CD105^+$, and, when in a population of placental cells, facilitate formation of one or more embryoid-like bodies under conditions that allow formation of embryoid-like bodies. In another specific embodiment, the placental stem cells are $OCT-4^+$ and, when in a population of placental cells, facilitate formation of one or more embryoid-like bodies in a population of isolated placental cells comprising said stem cell when cultured under conditions that allow formation of embryoid-like bodies.

The composition, comprising stem cells, can be formed into any shape, either prior to or subsequent to combining with stem cells. In one embodiment, said composition is shaped as a sheet, e.g., a dried sheet, having two sides, and said stem cells are present on at least one of said sides. In another embodiment, the composition is formed as a tube, and the stem cells are present on at least the inside or outside face of the tube. In another specific embodiment, the stem cells are adhered to the composition. In a specific embodiment of any of the above embodiments, the stem cells secrete IL-6, IL-8 and/or MCP-1 (monocyte chemotactic protein-1) when contacted with the composition.

In another aspect, the present invention provides processes for preparing base-treated, detergent-treated telopeptide collagen. Although the source of the placental tissue can be any mammal, human placenta is used in certain embodiments. The placental tissue can be from any part of the placenta including the amnion, whether soluble or insoluble or both, the chorion and the umbilical cord, or from the entire placenta. In certain embodiments, the placental collagen is prepared from whole human placenta following removal of the umbilical cord.

In certain embodiments, the processes comprise an osmotic shock of placental tissue. Although not intending to be bound by any particular theory of operation, it is believed that the osmotic shock can burst cells in the tissue thereby facilitating the removal of the cells, cellular components and blood components. The osmotic shock step can yield collagen compositions of the invention with advantageous purity. The osmotic shock can be carried out in any osmotic shock conditions known to those of skill in the art. In particular embodiments, the osmotic shock is carried out by incubation in high salt conditions followed by incubation in a water solution. The incubations can be repeated according to the judgment of those of skill in the art. In certain embodiments, they are repeated two times or more.

Following the osmotic shock, the resulting collagen composition can be treated with detergent. The detergent can be any detergent known to those of skill in the art to be capable of solubilizing the protein and lipid cellular components of the source tissue. In certain embodiments, the detergent is ionic, such as sodium dodecylsulfate or deoxycholate. In certain embodiments, the detergent is nonionic, such as a TWEEN® detergent or a TRITON®-X detergent. In certain embodiments, the detergent is zwitterionic. In certain other embodiments, the detergent is sodium dodecyl sulfate (SDS). In certain embodiments, the collagen composition is contacted with the detergent under conditions apparent to one of skill in the art for solubilizing cellular or subcellular components of the source tissue. The detergent treatment can be repeated according to the judgment of those of skill in the art. In certain embodiments, it is repeated two times or more.

In certain embodiments, the collagen composition can be treated under basic conditions. For instance, in certain embodiments, the collagen composition can be contacted with an alkaline solution, e.g. an ammonium hydroxide, potassium hydroxide or sodium hydroxide solution. In certain embodiments, the collagen composition is incubated at about 0.5 M sodium hydroxide for a time sufficient to yield a composition of the invention. The basic treatment can be repeated according to the judgment of those of skill in the art. In certain embodiments, it is repeated two times or more.

In certain embodiments, the steps of the process are carried out in any order. In certain embodiments, at least one osmotic shock step precedes any detergent treatment or treatment under basic conditions. In certain embodiments, at least one osmotic shock step precedes a detergent treatment which is followed by a basic treatment.

In a further aspect, the present invention provides methods for augmenting or replacing the tissue of a mammal by administering a collagen composition of the invention to a mammal in need thereof. In certain embodiments, the mammal is human. The collagen composition can be administered according to any technique known to those of skill in the art. In certain embodiments, the collagen compositions are administered by injection. In certain embodiments, the rheological properties of the collagen compositions of the invention are advantageous. In certain embodiments, the collagen composition can be used as an extracellular matrix according to the methods described in U.S. Patent Publication No. 2004/0048796, the contents of which are hereby incorporated by reference in their entireties.

In another aspect, the present invention provides kits for administering the collagen compositions of the invention to a mammal in need thereof. The kits typically comprise a collagen composition of the invention in a package convenient for distribution to a practitioner of skill in the art. The kits can further comprise means for administering the collagen composition of the invention to the mammal. The means can be any means for administering a collagen composition known to those of skill in the art such as a syringe, a syringe and needle, a canula, etc. In certain embodiments, the means is pre-filled with a collagen composition of the invention.

In another aspect, the invention provides a method of promoting healing of a wound comprising contacting the wound with a collagen composition of the invention, wherein said contacting results in detectably greater improvement of an aspect of the wound compared to a wound not contacted with the composition. In a specific embodiment, the method additionally comprises contacting said wound with a plurality of stem cells. In a more specific embodiment, said stem cells are contacted with said wound separately from contacting said composition with said wound. In another specific embodiment, said composition comprises said stem cells. In another specific embodiment, said composition is shaped as a sheet having two sides, and said stem cells are present on at least one of said sides. In another specific embodiment, the stem cells are adhered to the composition. In a specific embodiment of any of the above embodiments, the stem cells secrete IL-6, IL-8 and/or MCP-1 (monocyte chemotactic protein-1) when contacted with the composition. In a more specific embodiment, stem cells are placental stem cells. In a more specific embodiment, said placental stem cells are $CD34^-$ and/or $CD200^+$. In another specific embodiment, said wound is a leg ulcer. The leg ulcer can be a venous leg ulcer, arterial leg ulcer, diabetic leg ulcer or decubitus leg ulcer. In another specific embodiment, said composition is used as a wound filler.

In another aspect, the invention provides a method of making a composition, comprising contacting a collagen composition of the invention with a plurality of stem cells. In one embodiment, the method comprises allowing at least some of said plurality of stem cells to adhere to said composition. In another embodiment, the method comprises allowing said stem cells to proliferate on said composition. In a specific embodiment, the method comprises allowing said stem cells to proliferate on said composition to confluency. In certain embodiments, said stem cells produce detectable amounts of IL-6, IL-8 and/or MCP-1 when contacted with said composition. In another specific embodiment, the method comprises decellularizing the composition after said stem cells have deposited a detectable amount of at least one extracellular matrix protein. In more specific embodiments, the extracellular matrix protein is collagen (e.g., Type I, II, III or IV), fibronectin, or elastin.

As described above and in detail in the sections below, the compositions, processes, methods and kits of the invention have utility for administering collagen compositions to mammals in need thereof.

5. BRIEF DESCRIPTION OF THE FIGURES

FIG. 1: Flow chart representation of methods for isolating extracellular matrix (ECM).

Figure 2A:
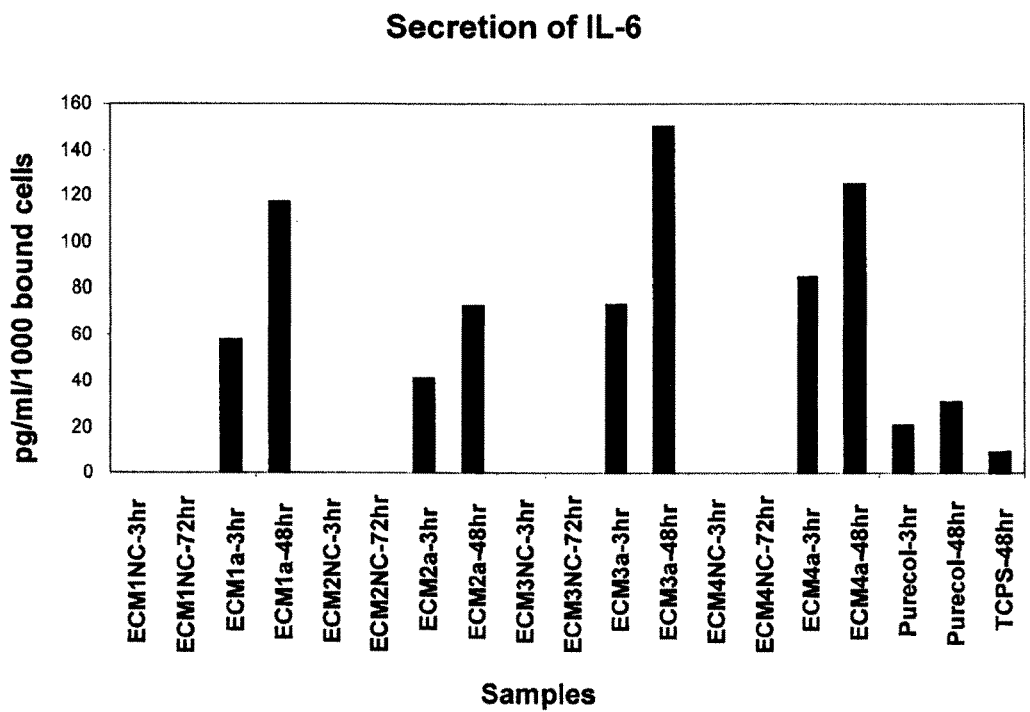

FIG. 2A: Secretion of IL-6 from placental stem cells grown on collagen composition made by different methods. Abscissa: Specific growth conditions by type of composition and time of growth of the cells on the composition. Ordinate: picograms per milliliter per 1000 ECM-bound cells. NC=no cells. Purecol=purified collagen. TCPS=tissue culture polystyrene.

Figure 2B:
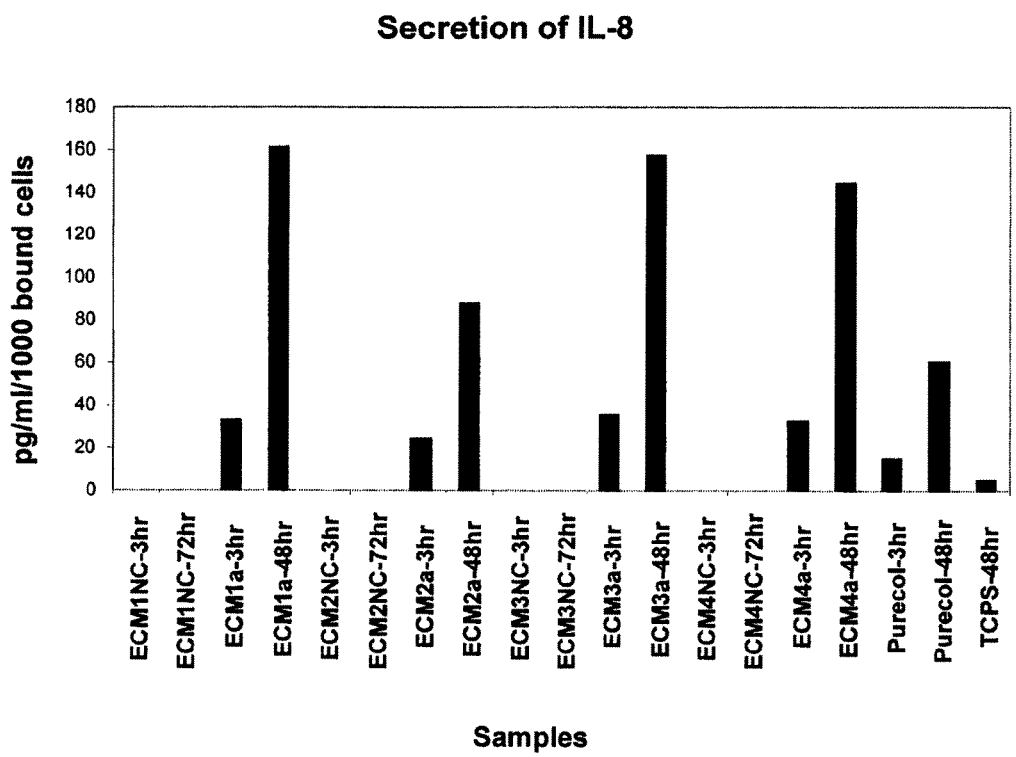

FIG. 2B: Secretion of IL-8 from placental stem cells grown on collagen composition made by different methods. Abscissa: Specific growth conditions by type of composition and time of growth of the cells on the composition. Ordinate: picograms per milliliter per 1000 ECM-bound cells. NC=no cells. Purecol=purified collagen. TCPS=tissue culture polystyrene.

Figure 2C:
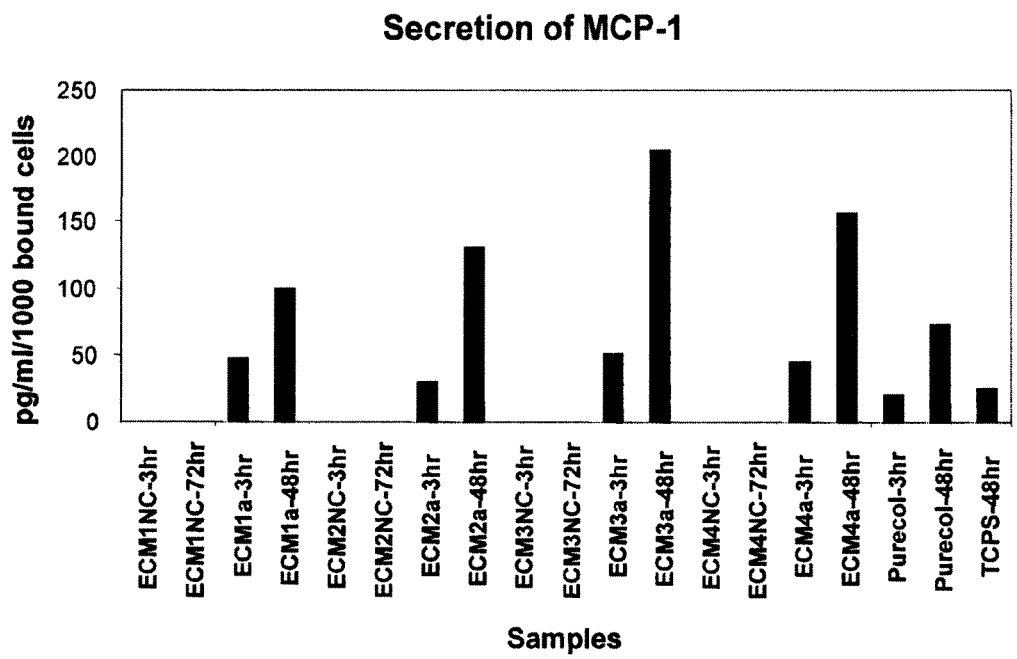

FIG. 2C: Secretion of MCP-1 from placental stem cells grown on collagen composition made by different methods. Abscissa: Specific growth conditions by type of composition and time of growth of the cells on the composition. Ordinate: picograms per milliliter per 1000 ECM-bound cells. NC=no cells. Purecol=purified collagen. TCPS=tissue culture polystyrene.

6. DETAILED DESCRIPTION OF THE INVENTION

6.1 Definitions

As used herein, the following terms shall have the following meanings:

The term "collagen" refers to any collagen known to those of skill in the art.

The term "telopeptide collagen" refers to a form of collagen, as recognized by those of skill in the art, that comprises one or more telopeptide regions.

The term "atelopeptide collagen" refers to a form of collagen, as recognized by those of skill in the art, that lacks one or more telopeptide regions. In certain embodiments, the telopeptide region can be removed by protease digestion as discussed in detail below.

"Biocompatibility" or "biocompatible" as used herein refers to the property of being biologically compatible by not producing a toxic, injurious, or immunological response or rejection in living tissue. Bodily response to unknown materials is a principal concern when using artificial materials in the body and hence the biocompatibility of a material is an important design consideration in such materials.

"Non-pyrogenic" as used herein refers to a material has been tested and found to contain less than or equal to 0.5 EU/mL of a pyrogen, e.g., endotoxin. One EU is approximately 0.1 to 0.2 ng of endotoxin per milliliter and varies according to the reference consulted.

The term "subject" refers to animals such as mammals, including, but not limited to, primates (e.g., humans), cows, sheep, goats, horses, dogs, cats, rabbits, rats, mice and the like. In certain embodiments, the subject is a human.

6.2 Embodiments of the Invention

The present invention is directed to collagen compositions, processes for preparing collagen compositions, kits comprising the collagen compositions and methods of their use.

6.2.1. Collagen Compositions of the Invention

In one embodiment, the present invention provides collagen compositions useful, for example, for augmenting or replacing tissue of a mammal. In certain embodiments, collagen compositions of the invention have advantageous durability, injectability and rheological properties. In certain other embodiments, the invention provides collagen compositions that possess space-filling properties and, e.g., facilitate and support growth of vasculature in a tissue contacted by the composition. In certain other embodiments, the composition of the invention is air-dried or freeze dried, and molded into a useful configuration. In certain other embodiments, the composition of the invention is insoluble in water.

In this aspect of the invention, the collagen can be any collagen known to those of skill in the art. In certain embodiments, the collagen is mammalian collagen. In particular embodiments, the collagen is human, bovine, ovine, sheep, rat or kangaroo collagen. In certain non-mammalian embodiments, the collagen is fish collagen. Although the collagen can be from any of these sources, human collagen is a particular example.

The collagen can be from any portion of the source. Useful sources include bovine skin, calf skin, rat tail, kangaroo tail and fish skin. In particular embodiments, the collagen is placental collagen, for instance bovine placental collagen, ovine placental collagen or human placental collagen. One example is human placental collagen.

The collagen can be any type of collagen known to those of skill in the art or a mixture of such collagens. In certain embodiments, the collagen is in the form of a collagen composition that comprises one or more types of collagen. Particular collagens include type I collagen, type II collagen, type III collagen and type IV collagen. In certain embodiments, the collagen composition of the invention comprises particular amounts of these collagens. A particular composition comprises a substantial amount of type I collagen while also being enriched in type IV collagen. In certain embodiments, a collagen composition of the invention comprises between 1 and 15% type IV collagen, between 2 and 13% type IV collagen, between 3 and 12% type IV collagen or between 4 and 11% type IV collagen. At the same time, the collagen composition can comprise at least 75%, at least 80%, at least 85%, at least 90%, at least 95%, or at least 99% type I collagen. For example, the composition can comprise between 70 and 95% type I collagen, between 74 and 92% type I collagen or between 80 and 90% type I collagen. The same collagen compositions of the invention can comprise an amount of type III collagen, for instance up to 1%, up to 2%, up to 3%, up to 4%, up to 5%, up to 6% or up to 7% type III collagen. In certain embodiments, the collagen compositions of the invention comprise between 2 and 15% type IV collagen, between 70 and 95% type I collagen and up to 6% type III collagen.

In certain embodiments, the collagen composition comprises one or more extracellular matrix proteins or components in addition to collagen. In specific embodiments, the collagen composition comprises fibronectin, laminin, elastin, and/or glygosaminoglycans. In another specific embodiment, the collagen composition comprises no detectable fibronectin, or no detectable laminin. In another specific embodiment, the collagen composition comprises detectable amounts of fibronectin and laminin. In another specific embodiment, the collagen composition comprises about 5% or more elastin by dry weight. In another specific embodiment, the collagen composition comprises about 10% or more elastin by dry weight. In another specific embodiment, the collagen composition comprises no more than about 5% elastin by dry weight.

These collagen compositions of the invention can be obtained by any process apparent to one of skill in the art. Particular processes are described in detail in the sections below.

In certain embodiments, the collagen compositions of this aspect of the invention are cross-linked. In certain embodiments, the collagen compositions can be cross-linked with a cross-linker such as glutaraldehyde according to methods known to those of skill in the art. Such methods are described extensively, for example, in U.S. Pat. Nos. 4,852, 640, 5,428,022, 5,660,692 and 5,008,116, and in McPherson et al., 1986, *J. Biomedical Materials Res.* 20:79-92, the contents of which are hereby incorporated by reference in their entirety.

Further exemplary cross-linkers and methods of their use for cross-linking collagen are described in U.S. Pat. Nos. 5,880,242 and 6,117,979 and in Zeeman et al., 2000, *J Biomed Mater Res.* 51(4):541-8, van Wachem et al., 2000, *J Biomed Mater Res.* 53(1):18-27, van Wachem et al., 1999, *J Biomed Mater Res.* 47(2):270-7, Zeeman et al., 1999, *J Biomed Mater Res.* 46(3):424-33, Zeeman et al., 1999, *Biomaterials* 20(10):921-31, the contents of which are hereby incorporated by reference in their entireties.

In further embodiments the collagen compositions of the invention are cross-linked with 1,4-butanediol diglycidyl ether. In further embodiments the collagen compositions of the invention are cross-linked with genipin. Genipin is a non-toxic, naturally occurring crosslinking agent. It can be obtained from its parent compound, geniposide, which may be isolated from the fruits of *Gardenia jasminoides*. Genipin may be obtained commercially from Challenge Bioproducts Co., Ltd., 7 Alley 25, Lane 63, TzuChiang St. 404 Taichung Taiwan R.O.C., Tel 886-4-3600852. The use of genipin as a cross-linking reagent is described extensively in U.S. Patent Application Publication No. 20030049301, the contents of which are hereby incorporated by reference in their entirety.

In further embodiments, the collagen composition can be cross-linked with other cross-linkers known to those of skill in the art. In further embodiments, the collagen composition can be cross-linked with any enzyme-mediated crosslinking technique known to those of skill in the art. For instance, the collagen composition of the invention can be cross-linked by transglutaminase according to methods known to those of skill in the art. Transglutaminase catalyzes the formation of the amide crosslink between the glutamine and lysine residues of collagen. Such methods are described, for example, in Orban et al., 2004, *J. Biomedical Materials Res.* 68(4): 756-62, the contents of which are hereby incorporated by reference in their entirety.

The collagen compositions of the invention can be cross-linked with a single cross-linker or with a mixture of cross-linkers. In certain embodiments, the collagen composition of the invention comprises base-treated, detergent treated human placental collagen cross-linked with glutaraldehyde.

6.3 Processes for Preparation of Collagen Compositions of the Invention

In another aspect, the present invention provides processes for preparing the collagen compositions of the invention. The processes are useful, for example, for preparing the collagen compositions of the invention described above.

In certain embodiments, the collagen compositions of the invention are prepared from human placenta according to the methods described herein. Initial steps of preparation of collagen compositions from human placenta are described in detail in U.S. Pat. Nos. 5,428,022, 5,660,692 and 5,008,116, and in U.S. Patent Application Publication Nos. 20040048796 and 20030187515, the contents of which are hereby incorporated by reference in their entireties.

The placental tissue can be from any part of the placenta including the amnion, whether soluble or insoluble or both, the chorion, the umbilical cord or from the entire placenta. In certain embodiments, the collagen composition is prepared from whole human placenta without the umbilical cord.

The placental sac is composed of two layers intimately connected by loose connective tissue. They are known as the amniotic and chorionic layers. The amniotic layer is the most internal of the two layers and comes into contact with the amniotic fluid that surrounds the fetus and together they form the amniotic sac. The amniotic layer is avascular and lined by simple columnar epithelium overlying a basal membrane and it measures 30-60 microns in thickness. The chorionic membrane is the outer layer of the sac and it is heavily cellularized. The vascular tree originates in the placenta and extends to the placental membranes through the chorionic layer. The chorionic layer is separated from the amniotic layer by loose connective tissue and combined, the two layers measure 120-180 microns. The placental membranes have a collagen matrix that is heavily laden with mucopolysaccharides and they are believed to serve primarily as a protective sac for the developing fetus. The membranes also maintain a barrier for infectious and immunologic agents present in the maternal circulation. Placental membranes have both active and passive transports. Most small molecules and proteins can travel freely through them but large proteins such as IgM cannot cross through the basal layer.

In a particular embodiment, the placenta for use in the methods of the invention is taken as soon as possible after delivery of a newborn. In yet another particular embodiment, the placenta is taken immediately following the cesarean section delivery of a normal healthy infant. Advantageously, the placenta can be collected under aseptic conditions. In some embodiments, the placenta is stored for 48 hours from the time of delivery prior to any further treatment. In other embodiments, the placenta is stored for up to 5 days from the time of delivery prior to any further treatment.

Advantageously, the placenta, umbilical cord, and umbilical cord blood can be transported from the delivery or birthing room to another location, e.g., a laboratory, for further processing. The placenta can be transported in a sterile, transport device such as a sterile bag or a container, which is optionally thermally insulated. In some embodiments, the placenta is stored at room temperature until further treatment. In other embodiments, the placenta is refrigerated until further treatment, i.e., stored at a temperature of about 2° to 8° C. In yet other embodiments, the placenta is stored under sterile conditions for up to 5 days before further treatment. In a particular embodiment, the placenta is handled and processed under aseptic conditions, as known to one skilled in the art. The laboratory can be equipped with an HEPA filtration system (as defined by clean room classification, having a class 1000 or better). In a particular embodiment, the HEPA filtration system is turned on at least 1 hour prior to using the laboratory room for carrying out the methods of the invention.

In certain embodiments, the placenta is exsanguinated, i.e., completely drained of the cord blood remaining after birth. In some embodiments, the placenta is 70% exsanguinated, 80% exsanguinated, 90% exsanguinated, 95% exsanguinated or 99% exsanguinated.

The invention encompasses screening the expectant mother prior to the time of birth, using standard techniques known to one skilled in the art, for communicable diseases including but not limited to, HIV, HBV, HCV, HTLV, syphilis, CMV, and other viral pathogens known to contaminate placental tissue. Advantageously, the methods can be used to screen for a communicable disease follow the regulations as set forth by the Federal Drug Administration. The expectant mother may be screened (e.g., a blood sample is taken for diagnostic purposes) within one month of birth, particularly within two weeks of birth, within one week of birth, or at the time of birth. Only tissues collected from donors whose mothers tested negative or non-reactive to the above-mentioned pathogens are used to produce a collagen composition of the invention. Advantageously, a thorough paternal and medical and social history of the donor of the placental membrane can be obtained, including for example, a detailed family history.

In certain embodiments, the donor is screened using standard serological and bacteriological tests known to one skilled in the art. Any assay or diagnostic test that identifies the pathogen(s) is within the scope of the method of the invention, but particular assays are ones that combine high accuracy with capacity for high throughput. In a specific embodiment, the invention encompasses screening the donor using standard techniques known to one skilled in the art for antigens and/or antibodies. A non-limiting example of antigens and antibodies include: antibody screen (ATY); alanine amino transferase screening (ALT); Hepatitis Core Antibody (nucleic acid and ELISA); Hepatitis B Surface Antigen; Hepatitis C Virus Antibody; HIV-1 and HIV-2; HTLV-1 and HTLV-2; Syphilis test (RPR); CMV antibody test; and Hepatitis C and HIV test. The assays used may be nucleic acid based assays or ELISA based assays as known to one skilled in the art.

The invention encompasses further testing the blood from the umbilical cord of the newborn using standard techniques known to one skilled in the art (See, e.g., Cotorruelo et al., 2002, *Clin. Lab.* 48(5 6):271 81; Maine et al., 2001, *Expert Rev. Mol. Diagn.*, 1(1):19 29; Nielsen et al., 1987, *J. Clin. Microbiol.* 25(8):1406 10; all of which are incorporated herein by reference in their entirety). In one embodiment, the blood from the umbilical cord of the newborn is tested for bacterial pathogens (including but not limited to gram positive and gram negative bacteria) and fungi using standard techniques known to one skilled in the art. In a specific embodiment, the blood type and Rh factor of the blood of the umbilical cord of the newborn is determined using standard techniques known to those skilled in the art. In another embodiment, CBC with differential is obtained from the blood from the umbilical cord of the newborn using standard methods known to one skilled in the art. In yet another embodiment, an aerobic bacterial culture is taken from the blood from the umbilical cord of the newborn, using standard methods known to one skilled in the art. Only tissues collected from donors that have a CBC within a normal limit (e.g., no gross abnormality or deviation from the normal level), test negative for serology and bacteriology, and test negative or non-reactive for infectious disease and contamination are used to produce a collagen composition of the invention.

Once the human placental tissue is obtained, it can be treated according to the following steps in order to prepare a collagen composition of the invention. Although the following steps are presented in sequential order, one of skill in the art will recognize that the order of several steps can be interchanged without exceeding the scope of the invention. Furthermore, several steps are indicated as optional depending on the nature of the desired collagen composition of the invention. It is assumed that techniques readily apparent to those of skill in the art such as buffer exchange, precipitation, centrifugation, resuspension, dilution and concentration of protein compositions need not be explained in detail. An exemplary preparation is described in the examples below.

Any portion of the placenta, or the entire placenta, can be used in the processes of the present invention. In certain embodiments, collagen compositions are prepared from whole placenta. However, in certain embodiments, collagen compositions can be obtained from chorionic or amnionic portions of the placenta.

In these embodiments, the invention encompasses processing the placental membrane so that the umbilical cord is separated from the placental disc, and separation of the amniotic membrane from the chorionic membrane. In a particular embodiment, the amniotic membrane is separated from the chorionic membrane prior to cutting the placental membrane. The separation of the amniotic membrane from the chorionic membrane can be done starting from the edge of the placental membrane. In another embodiment, the amniotic membrane is separated from the chorionic membrane using blunt dissection, e.g., with gloved fingers. Following separation of the amniotic membrane from the chorionic membrane and placental disc, the umbilical cord stump is cut, e.g., with scissors, and detached from the placental disc. In certain embodiments, when separation of the amniotic and chorionic membranes is not possible without tearing the tissue, the invention encompasses cutting the amniotic and chorionic membranes from the placental disc as one piece and then peeling them apart.

The amniotic membrane, chorionic membrane or whole placenta can be stored prior to use in the processes of the invention. Storage techniques will be apparent to one of skill in the art. Exemplary storage techniques are described in U.S. Patent Application Publication Nos. 20040048796 and 20030187515, the contents of which are hereby incorporated by reference in their entireties.

In some processes of the invention, the placental tissue is decellularized. The placental tissue can be decellularized according to any technique known to those of skill in the art such as those described in detail in U.S. Patent Application Publication Nos. 20040048796 and 20030187515, the contents of which are hereby incorporated by reference in their entireties.

In certain embodiments, the placental tissue is subjected to an osmotic shock. The osmotic shock step can yield collagen compositions of the invention with advantageous purity. Although not intending to be bound by any particular theory of operation, it is believed that the osmotic shock can burst cells in the tissue and thereby facilitating the removal of the cells, cellular components and blood components. The osmotic shock can be in addition to any clarification step or it can be the sole clarification step according to the judgment of one of skill in the art.

The osmotic shock can be carried out in any osmotic shock conditions known to those of skill in the art. Such conditions include incubating the tissue in solutions of high osmotic potential, or of low osmotic potential or of alternating high and low osmotic potential. The high osmotic potential solution can be any high osmotic potential solution known to those of skill in the art such as a solution comprising one or more of NaCl (e.g., 0.2-1.0 M), KCl (e.g., 0.2-1.0 or 2.0 M), ammonium sulfate, a monosaccharide, a disaccharide (e.g., 20% sucrose), a hydrophilic polymer (e.g., polyethylene glycol), glycerol, etc. In certain embodiments, the high osmotic potential solution is a sodium chloride solution. In some embodiments, the sodium chloride solution is at least 0.25 M, 0.5M, 0.75M, 1.0M, 1.25M, 1.5M, 1.75M, 2M, or 2.5M NaCl. In some embodiments, the sodium chloride solution is about 0.25-5M, about 0.5-4M, about 0.75-3M, or about 1.0-2.0M NaCl.

The low osmotic potential solution can be any low osmotic potential solution known to those of skill in the art, such as water, for example water deionized according to any method known to those of skill. In some embodiments, the osmotic shock solution comprises water with an osmotic shock potential less than that of 50 mM NaCl.

In certain embodiments, the osmotic shock is in a sodium chloride solution followed by a water solution. In some embodiments, the sodium chloride solution is at least 0.5 M NaCl. In certain embodiments, the sodium chloride solution is at least 0.75M NaCl. In some embodiments, the sodium chloride solution is at least 1.0M NaCl. In some embodiments, the sodium chloride solution is at least 1.5M NaCl. In some embodiments, the sodium chloride solution is at least 2.0M NaCl. In certain embodiments, one 0.5 M NaCl treatment is followed by a water wash. In certain embodiments, two 0.5 M NaCl treatments are followed by a water wash. In certain embodiments, one 2M NaCl treatment is followed by a water wash. These sequences can be repeated according to the judgment of one of skill in the art.

In certain embodiments, the collagen composition resulting from the osmotic shock can be incubated with a detergent. Although not intending to be bound by any particular theory of operation, it is believed that a detergent can disrupt cells, cellular membranes, subcellular membranes and cellular debris that might be present in the composition. The detergent can be any detergent known to those of skill in the art to be capable of disrupting cellular or subcellular membranes. In certain embodiments, the detergent is ionic. For instance, in certain embodiments, the detergent is deoxycholate or sodium dodecylsulfate. In the working examples below, an exemplary detergent treatment is with deoxycholic acid. In certain embodiments, the detergent is zwitterionic. In certain embodiments, the detergent is nonionic. For instance, in certain embodiments, the detergent can be a TWEEN® detergent, such as TWEEN®-20, or a triton X detergent, such as triton X 100. The collagen composition should be contacted with the detergent under conditions judged by one of skill in the art to be suitable for removing unwanted components from the composition. Exemplary conditions are provided in the working examples below.

The detergent treatment can be carried out at any temperature according to the judgment of those of skill in the art. In certain embodiments, the detergent treatment is carried out at about 0-30° C., about 5-25° C., about 5-20° C., or about 5°-15° C. In certain embodiments, the detergent treatment is carried out at about 0° C., about 5° C., about 10° C., about 15° C., about 20° C., about 25° C., or about 30° C. In particular embodiments, the detergent treatment is carried out at about 5-15° C.

The detergent treatment can be carried out for a suitable time according to the judgment of those of skill in the art. In certain embodiments, the detergent treatment can be carried out for about 1-24 hours, about 2-20 hours, about 5-15 hours, about 8-12 hours, or about 2-5 hours.

In certain embodiments, the collagen composition resulting from the detergent treatment can be incubated in basic conditions. Although not intending to be bound by any particular theory of operation, it is believed that a basic treatment can remove viral particles that might contaminate the collagen composition. In certain embodiments, the basic wash acts to remove endotoxins. The basic conditions can be any basic conditions known to those of skill in the art. In particular, any base at any pH known to remove viral particles can be used. Particular bases for the basic treatment include biocompatible bases, volatile bases and bases known to those of skill in the art to be easily and safely removed from the collagen composition. The base can be any organic or inorganic bases known to those of skill in the art at a concentration of, for example, 0.2-1.0M. In certain embodiments, the base is selected from the group consisting of ammonium hydroxide, potassium hydroxide and sodium hydroxide. In certain embodiments, the base treatment is carried out in sodium hydroxide solution. The sodium hydroxide solution can be 0.1M NaOH, 0.25M NaOH, 0.5M NaOH, or 1M NaOH. In particular embodiments, the basic treatment is carried out in 0.1M or 0.5M NaOH.

The basic treatment can be carried out at any temperature according to the judgment of those of skill in the art. In certain embodiments, the basic treatment is carried out at about 0-30° C., about 5-25° C., about 5-20° C., or about 5°-15° C. In certain embodiments, the basic treatment is carried out at about 0° C., about 5° C., about 10° C., about 15° C., about 20° C., about 25° C., or about 30° C. In particular embodiments, the basic treatment is carried out at about 5-15° C.

The basic treatment can be carried out for a suitable time according to the judgment of those of skill in the art. In certain embodiments, the basic treatment can be carried out for about 1-24 hours, about 2-20 hours, about 5-15 hours, about 8-12 hours, or about 2-5 hours.

Variations of the detergent and NaOH wash steps can be used to generate a number of variations of the final ECM material. For example, in certain embodiments, the collagen-containing tissue can be treated with about 0.1 M, 0.2 M, 0.3 M, 0.4 M, or about 0.5 M NaOH over about 3, 4, 5, 6, 7, 8, 9, 10, 11, 12, 13, 14, 15, 16, 17, 18, 19, 20, 21, 22, 23, or about 24 hours.

In certain other embodiments, the collagen composition of the invention is produced without treatment by a base. Where the process is applied to placental tissue, omission of a base treatment step typically results in a collagen composition comprising relatively higher amounts of elastin, fibronectin and/or laminin than the collagen composition produced with inclusion of the basic treatment.

In certain embodiments, the collagen composition can be dried. Drying facilitates storage and packaging of the collagen composition. Drying also makes cellular components more susceptible to removal from the composition. Further, after any of the above steps, the collagen composition can be dried prior to the succeeding step. Drying can be carried out according to any technique for drying apparent to those of skill in the art. Useful drying techniques are described in U.S. Patent Publication No. 2004/0048796, the contents of which are hereby incorporated by reference in their entirety. Exemplary drying techniques include lyophilization, vacuum drying, heat (e.g., below about 50° C.) freeze drying, as demonstrated in the working examples below.

In certain embodiments, any of the above steps can be carried out under sterile conditions. In particular embodiments, the basic treatment, and all subsequent steps, are carried out under sterile conditions. In further embodiments, any collagen composition prepared according to the methods described herein can be further sterilized according to techniques apparent to one of skill in the art.

In certain embodiments, the present invention provides processes that comprise the osmotic shock, freeze dry, detergent treatment, water wash, freeze dry, basic treatment, water wash and freeze dry steps described above. In certain embodiments, these steps are carried out in order. In certain embodiments, the detergent is 1% deoxycholate. In certain embodiments, the basic treatment is 0.5 N NaOH for four hours. In certain embodiments, the first water wash is repeated (two total washes). In certain embodiments, the second water wash is repeated twice (three total washes). In certain embodiments, the detergent is 1% deoxycholate, the basic treatment is 0.5 N NaOH for four hours, the first water wash is repeated (two total washes) and the second water wash is repeated twice (three total washes). In certain embodiments, such a process can provide a composition comprising about 0.59% glycosaminoglycans, about 3.5% elastin, little or no fibronectin and little or no laminin.

In certain embodiments, the present invention provides processes that comprise the osmotic shock, basic treatment and water wash steps described above. In certain embodiments, these steps are carried out in order. In certain embodiments, the basic treatment is 0.5 N NaOH for four hours. In certain embodiments, such a process can provide a composition comprising about 0.28% to about 0.38% glycosaminoglycans, about 3.2% to about 4.7% elastin, little or no fibronectin and little or no laminin.

In certain embodiments, the present invention provides processes that comprise the osmotic shock, detergent treatment and water wash steps described above. In certain embodiments, these steps are carried out in order. In certain embodiments, the detergent is 1% deoxycholate. In certain embodiments, such a process can provide a composition comprising about 0.4% glycosaminoglycans, about 12% elastin, about 0.6% fibronectin and about 0.16% laminin.

6.3.1. Optional Further Treatment

In certain embodiments, a collagen composition of the invention can be used as a source for an atelopeptide collagen composition. The atelopeptide collagen composition can be used for any purpose apparent to those of skill in the art for atelopeptide collagen.

In such embodiments, the collagen composition can be contacted with an enzyme capable or partially or completely removing telopeptides from the collagen. The enzyme can be any proteolytic enzyme known to those of skill in the art that is capable of removing telopeptides from the collagen. In certain embodiments, the enzyme is pepsin or papain. Generally, the enzyme is contacted with the collagen composition under conditions suitable for removal of telopeptide known to those of skill in the art.

Methods of treating collagen compositions with enzymes to remove telopeptides are described in detail in U.S. Pat. Nos. 4,511,653, 4,582,640, 5,436,135 and 6,548,077, the contents of which are hereby incorporated by reference in their entireties. Generally, the enzyme is contacted with the collagen composition under conditions suitable for removal of telopeptide known to those of skill in the art. Such conditions include, for example, contacting the enzyme with the collagen composition in suitable pH, at suitable enzyme concentration, in a suitable volume of a solution, at suitable temperature and for a suitable time.

The collagen composition can be contacted with the enzyme under low pH conditions according to the judgment of those of skill in the art. In certain embodiments, the collagen position is contacted with pepsin at pH about 1-3 or about 2-3.

In certain embodiments, the enzyme is contacted with the collagen composition at elevated temperature. Although not intending to be bound by any particular theory of operation, it is believed that the elevated temperature can improve the yield of type I collagen in the final collagen composition. In certain embodiments, the collagen composition is contacted with pepsin at about 15-40° C., about 20-35° C., about 25-30° C., about 20-30° C., or about 23-27° C. In particular embodiments, the collagen composition is contacted with pepsin at about 23-27° C. for a time sufficient to remove telopeptide.

The collagen composition is contacted with the enzyme for a time sufficient to remove telopeptide according to the judgment of those of skill in the art. In certain embodiments, the collagen is contacted with pepsin for at least 5, 10, 15, 20, 25 or 30 hours. In certain embodiments, the is contacted with pepsin for about 5-30 hours, about 10-25 hours or about 20-25 hours. In certain embodiments, the is contacted with pepsin for about 8, 16, 24 or 32 hours.

The collagen composition is contacted with the enzyme in an amount suitable to remove telopeptide according to the judgment of those of skill in the art. In some embodiments, about 0.1 g, 0.5 g, 1.0 g, 2.0 g or 5.0 g pepsin/kg of frozen placenta is contacted with the collagen composition. In other embodiments, about 0.1 g, 0.5 g, 1.0 g, 2.0 g or 5.0 g pepsin/placenta is contacted with the collagen composition. In certain embodiments, the collagen composition is contacted with about 0.1-10.0 g/L, about 0.5-5/L, about 1-2.5 g/L, or about 0.5-1.5 g/L pepsin. In some embodiments, the collagen composition is contacted with about 0.1 g/L, about 0.2 g/L, about 0.5 g/L, about 1.0 g/L, about 2.0 g/L, 5 g/L or 10 g/L pepsin. In particular embodiments, the collagen composition is contacted with about 0.5-1.0 g/L pepsin in acetic acid solution with pH about 2-3, at about 23° C.-27° C. for about 16-24 hours.

The collagen composition is contacted with the enzyme in a suitable solution volume:placenta to remove telopeptide according to the judgment of those of skill in the art. It is observed that a high volume ratio to placenta can maximize the effect by pepsin. In certain embodiments, about 1, 2, 4, or 8 volumes of acetic acid solution per placenta is used. In particular embodiments, about 2 volumes of acetic acid solution per placenta is used.

If desired, the collagen compositions of the invention can be further processed by fibrillation. The fibrillation can be carried out by any technique for fibrillating collagen known to those of skill in the art. Fibrillation of collagen compositions is described extensively in U.S. Pat. Nos. 4,511,653, 4,582,640 and 5,436,135, the contents of which are hereby incorporated by reference in their entireties. If necessary, the collagen composition can be concentrated according to standard techniques prior to fibrillation.

Where desired, the collagen compositions of the invention can be cross-linked. In certain embodiments, the collagen composition is fibrillated prior to cross-linking. The cross-linking can be with any cross-linker known to those of skill in the art, for instance, the cross-linkers discussed in the section above. In certain embodiments, the cross-linker can be glutaraldehyde, and the cross-linking can be carried out according to methods of glutaraldehyde cross-linking of collagen known to those of skill in the art. In other embodiments, the cross-linker can be 1,4-butanediol diglycidyl ether or genipin. In particular embodiments, the cross-linker is 1,4-butanediol diglycidyl ether.

In some embodiments, a covalent bond between a cross-linker and a collagen can be reduced, for example to improve stability. The reduction can be accomplished by contacting the collagen composition of the invention with any reducing agent known to those of skill in the art. In certain embodiments, the reducing agent is sodium borohydride, sodium bisulfite, β-mercaptoethanol, mercaptoacetic acid, mercaptoethylamine, benzyl mercaptan, thiocresol, dithiothreitol or a phosphine such as tributylphosphine. Sodium borohydride is a useful example. In certain embodiments, the collagen is cross-linked prior to reduction with the reducing agent. Reduction of collagen compositions and cross-linked collagen compositions is described extensively in U.S. Pat. Nos. 4,185,011, 4,597,762, 5,412,076 and 5,763,579, the contents of which are hereby incorporated by reference in their entirety.

In certain embodiments, the collagen composition can be further processed by mechanical shearing according to methods known to those of skill in the art. Exemplary shearing techniques are described in U.S. Pat. No. 4,642,117, the contents of which are hereby incorporated by reference in their entirety. In certain embodiments, the collagen composition is sheared with a tissue homogenizer known to those of skill in the art.

In certain embodiments, steps can be taken to limit protease activity in the collagen compositions of the invention. Additives such as metal ion chelators, for example 1,10-phenanthroline and ethylenediaminetetraacetic acid (EDTA), create an environment unfavorable to many proteolytic enzymes. Providing sub-optimal conditions for proteases such as collagenase may assist in protecting the collagen compositions from degradation. Suboptimal conditions for proteases may be achieved by formulating the compositions to eliminate or limit the amount of calcium and zinc ions available in solution. Many proteases are active in the presence of calcium and zinc ions and lose much of their activity in calcium and zinc ion free environments. Advantageously, a collagen composition will be prepared selecting conditions of pH, reduced availability of calcium and zinc ions, presence of metal ion chelators and the use of proteolytic inhibitors specific for collagenase. For example a collagen composition may include a buffered solution of water, pH 5.5 to 8, or pH 7 to 8, free from calcium and zinc ions and including a metal ion chelator such as EDTA. Additionally, control of temperature and time parameters during the treatment of a collagen composition may also be employed to limit the activity of proteases.

6.4 Characterization of the Collagen Composition

6.4.1. Biochemical Characterization

Biochemical based assays known in the art and exemplified herein may be used to determine the biochemical compositions of the collagen compositions of the invention. The invention encompasses biochemical based assays for determining the total protein content of a sample such as for examples absorbance based assays and colorimetric based assays. Absorbance based assays include but are not limited to assays that measure absorbance at 280 nm (see, e.g., Layne, E, Spectrophotometric and Turbidimetric Methods for Measuring Proteins, Methods in Enzymology 3: 447-455, (1957); Stoscheck, C M, Quantitation of Protein, Methods in Enzymology 182: 50-69, (1990); which are incorporated herein by reference in their entireties), 205 nm, and assays based on the extinction coefficient of the sample (see, e.g., Scopes, R K, Analytical Biochemistry 59: 277, (1974); Stoscheck, C M. Quantitation of Protein, Methods in Enzymology 182: 50-69, (1990); which are incorporated herein by reference in their entireties). The invention encompasses methods for determining the total content of specific protein in the collagen compositions of the invention including but not limited to collagen (e.g., collagen type I, type III, type IV), laminin, elastin, fibronectin, and glycosaminoglycan.

Colorimetric based assays included but are not limited to modified Lowry assay, biuret assay, Bradford assay, Bicinchoninic Acid (Smith) assay (see, Stoscheck, C M, Quantitation of Protein, Methods in Enzymology 182: 50-69 (1990)).

In a specific embodiment, the measuring the total protein content of a collagen composition of the invention using a Bradford dye-binding assay (Bradford, M., Analytical Biochemistry, 72, 248 (1976), which is incorporated herein by reference in its entirety). An exemplary Bradford assay for use in the methods of the invention may comprise the following: the assay can be carried out using the (Bradford dye-binding assay available through BIO-RAD, Hercules, Calif., USA. The protein assay is based on the change in color of the dye Coomassie Brilliant Blue R-250 in response to different concentrations of protein. The assay involves developing a standard calibration curve by measuring absorbance (at 595 nanometers) of a series of human collagen standards of known concentrations. The concentration of collagen in a test sample, for example, sample of the amniotic membrane, is determined by referencing to the standard curve. The assay is developed in a standard format that allows measurement of collagen concentration in the range of 0.2-1.4 mg/mL and as a microassay that measures protein concentration up to 25 µg. For the standard assay, collagen dissolved in 100 mM citric acid (pH 2.4) is aliquoted into 1.5 mL microcentrifuge tubes at concentrations of 0.1-1 mg/mL at a total volume of 0.1 mL. To each tube, 1 mL of the Coomassie blue dye is added. Samples are vortexed and allowed to stand at room temperature for 10 minutes. Absorbance is measured at 595 nanometers (nm). For the micro-assay, collagen dissolved in 100 mM citric acid (pH 2.4) is aliquoted into wells of a 96-well plate at a total volume of 0.1 mL (2.5-30 µg/mL). To each well, 10 µL of dye reagent is added. Samples are vortexed, incubated at room temperature for ten minutes before measuring absorbance in a plate reader at 595 nm. For a collagen composition of the invention, test samples can be assayed in triplicate. Protein concentrations are determined by referencing to the standard curve. Protein concentration is calculated as a percentage of the total dry weight of the membrane. Within a margin of error of about 10%, the protein content in each of the membrane is essentially 95% or more of the total dry weight of the membrane. Water content may be low and within the experimental error (approximately 10%).

Estimation of the total collagen content of the collagen compositions of the invention may be characterized using methods known to one skilled in the art and exemplified herein. In a specific embodiment the collagen content of a collagen composition of the invention is measured using a quantitative dye-based assay kit (SIRCOL) manufactured by Biocolor Ltd, UK. The assay utilizes Sirius Red (or Direct Red 80) as a specific collagen binding dye. Dye bound to collagen displays a concentration dependent increase in absorbance at 540 nm in a UV-Vis spectrophotometer. The assay involves developing a standard calibration curve by measuring absorbances of a series of bovine collagen standards of known concentrations. The concentration of collagen in a test sample, for example, amniotic membrane sample, is determined by referencing to the standard curve. In an exemplary assay, collagen (1 mg/mL) is aliquoted into 1.5 mL microcentrifuge tubes at concentrations from 5-100 µg/100 µL. Sample volumes are adjusted to a 100 µL with water. To each sample 1 mL of SIRCOL dye reagent is added at room temperature. Sample tubes are capped and allowed to incubate at room temperature with mechanical shaking for 30 mm. The samples are then centrifuged at 12,000×g for 15 minutes and liquid drained using a pipetter. The reddish precipitate at the bottom of each tube is dissolved in 1 mL of 0.5M NaOH (sodium hydroxide). UV absorbance for the samples is measured at 540 nm using a Beckman DU-7400

UV-VIS spectrophotometer. The standard calibration curve is plotted using the concentration of collagen in each sample versus the absorbance (OD) at 540 nm. To determine experimental error the assay is repeated (n=10) at a single low concentration of collagen standard (10 μg/100 μL). The membrane sample is assayed using the same protocol, the sample being added in a total volume of 100 μL.

In yet other embodiments, to determine collagen types of the collagen compositions of the invention using standard methods known in the art and exemplified herein, e.g., ELISA assay, may be employed. An exemplary assay for determining the types of collagen, e.g., collagen Types I, III and IV, in a collagen composition of the invention comprises using a sandwich ELISA assay provided, for example, as a kit by Anthrogen-CIA Collagen-I from Chondrex, Inc., Redmond, Wash., USA. For the Type III and Type IV studies, the primary (Capture Antibody) and secondary antibodies (Detection Antibody) and collagen standards may be obtained from Rockland Immunochemicals, Gilbertsville, Pa. The detection antibody is a biotinylated human collagen Type-I, III or IV, which binds streptavidin peroxidase. The enzymatic reaction with a chromogenic substrate and urea and $H_2O_2$ gives a yellow color, which is detected via UV-Vis spectroscopy at 490 nm. To quantitate the amount of Collagen-type, a standard calibration curve is developed with a sample of a series of human collagen standards of known concentrations. The concentration of Collagen in a test sample of amniotic membrane is determined by referencing to the standard curve. Assay protocols are developed as per the recommendations of the ELISA kit. To develop a standard calibration curve, 10-12 wells in a 96-well tray are coated with the capture antibody (anti-human type-I collagen antibody, unconjugated) by adding 100 μL of a 100×-diluted Capture Antibody provided with the kit. After overnight incubation, the wells are washed with three times with a wash buffer to remove unbound antibody. Human Collagen Type I is then added to the wells in increasing concentration from 0-5 μg/mL in a 100 μL volume. After a two hour incubation at room temperature, the wells are washed with the wash buffer three times to remove unbound collagen. The biotinylated Collagen-I antibody is then added to the antibody-collagen complex in the wells in a 100 μL volume and allowed to bind at room temperature for two hours. Unbound anti-body is washed out with three washes with the wash buffer. The detection enzyme streptavidin peroxidase is then bound to the antibody-collagen-antibody complex by addition of a 200×-diluted sample of the enzyme provided with the kit and allowing it to incubate at room temperature for one hour. The 96-well plate is washed repeatedly (six times) to remove any unbound enzyme. The chromogenic substrate+urea/$H_2O_2$ is added to each of the wells in a 100 μL, volume. The reaction is allowed to proceed for 30 minutes at room temperature. The reaction is terminated by addition of 50 μL it of 2.5 N sulfuric acid. Absorbance is measured at 490 nm.

In yet other embodiments, the invention encompasses assays for determining the total elastin content of the collagen compositions of the invention using methods known in the art and exemplified herein. An exemplary assay for measuring the elastin content of a collagen composition of the invention may comprise a quantitative dye-based assay kit (FASTIN) manufactured by Biocolor Ltd, UK. The assay utilizes 5,10,15,20-tetraphenyl-21,23-porphrine (TPPS) as a specific elastin binding dye (see, e.g., Winkleman, J. (1962), Cancer Research, 22, 589-596, which is incorporated herein by reference in its entirety). Dye bound to elastin displays a concentration dependent increase in absorbance at 513 nm in a UV-Vis spectrophotometer. The assay involves developing a standard calibration curve by measuring absorbances of a series of bovine elastin standards of known concentrations. The concentration of elastin in a test sample, for example, sample of the amniotic membrane, is determined by referencing to the standard curve. Elastin (1 mg/mL) is aliquoted into 1.5 mL microcentrifuge tubes at concentrations from 5-100 μg/100 μL. Sample volumes are adjusted to 100 μL with water. To each sample 1 mL of Elastin precipitation Reagent (trichloroacetic acid+arginine) is added at 4° C. and stored overnight at the same temperature. Following the overnight precipitation step, the samples are centrifuged at 12,000×g for 15 minutes and liquid is drained using a pipetter. To each sample, 1 mL of the FASTIN dye reagent (TPPS) is added with a 100 μL of 90% saturated ammonium sulfate. Sample tubes are capped and allowed to incubate at room temperature with mechanical shaking for 1 hr. The ammonium sulfate serves to precipitate the elastin-dye complex. After the 1 hr mixing step, the samples are centrifuged at 12,000×g for 15 minutes and liquid is drained using a pipetter. The brown precipitate at the bottom of each tube is dissolved into 1 mL of FASTIN dissociation reagent which is a solution of guanidine HCL in I-propanol. UV absorbance for the samples is measured at 513 nm using a Beckman DU-7400 UV-VIS spectrophotometer. The standard calibration curve is plotted using the concentration of elastin in each sample versus the absorbance (OD) at 513 nm. To determine experimental error in the assay, the assay is repeated (n=10) at a single low concentration of elastin standard (10 μg/100 μL). The membrane sample is assayed using the same protocol, the sample being added in a total volume of 100 μL. Each sample is assayed in triplicate.

In yet other embodiments, the invention encompasses assays for determining the total glycosaminoglycan (GAGs) content of the collagen compositions of the invention using methods known in the art and exemplified herein. The presence of GAGs in a collagen composition of the invention may be measured using a quantitative dye-based assay kit (BLYSCAN) manufactured by Biocolor Ltd, UK. The assay utilizes 1,9-dimethyl-methylene blue as a specific GAG binding dye. Dye bound to GAG displays a concentration dependent increase in absorbance at 656 nm in a UV-Vis spectrophotometer. The assay involves developing a standard calibration curve by measuring absorbances of a series of bovine GAG standards of known concentrations. The concentration of GAG in a test sample of amniotic membrane is determined by referencing to the standard curve. Bovine GAG (0.1 mg/mL) is aliquoted into 1.5 mL microcentrifuge tubes at concentrations from 0.5-5 μg/100 μL. Sample volumes are adjusted to a 100 μL with water. To each sample 1 mL of the 1,9-dimethyl-methylene dye reagent is added at room temperature. Sample tubes are capped and allowed to incubate at room temperature with mechanical shaking for 30 minutes. The samples are then centrifuged at 12,000×g for 15 minutes and liquid drained using a pipetter. The reddish precipitate at the bottom of each tube was dissolved in 1 mL of a dye dissociation reagent. UV absorbance for the samples is measured at 656 nm using a Beckman DU-7400 UV-VIS spectrophotometer. The standard calibration curve is plotted using the concentration of GAG in each sample versus the absorbance (OD) at 540 nm. To determine experimental error in the assay, the assay is repeated (n=8) at a single low concentration of GAG standard (1 μg/100 μL). The membrane sample is assayed using the same protocol, the sample being added in a total volume of 100 μL. Each sample is assayed in triplicate.

In yet other embodiments, the invention encompasses assays for determining the total laminin content of the collagen compositions of the invention using methods known in the art and exemplified herein. An exemplary assay for determining the total laminin content in a collagen composition of the invention may comprise the following: a sandwich ELISA assay provided as a kit from Takara Bio Inc., Shiga, Japan (Cat # MKIO7 may be used. The kit includes a 96-well plate pre-coated with the primary (Capture Antibody), which is a murine monoclonal antibody to human laminin. The secondary antibodies (Detection antibody) and human laminin standards are provided with the kit. The detection antibody is a conjugated human laminin antibody with peroxidase. The enzymatic reaction with a chromogenic substrate tetramethylbenzidine and $H_2O_2$ gives a blue color, which is detected via UV-Vis spectroscopy at 450 nm. To quantitate the amount of laminin, a standard calibration curve is developed with a sample of a series of human laminin standards of known concentrations (provided with kit). The concentration of laminin in a test sample of amniotic membrane is determined by referencing to the standard curve. Assay protocols are developed as per the recommendations of the Elisa kit. To develop a standard calibration curve, the human laminin standard is added in increasing concentrations of 5 ng/mL to 160 ng/mL in a final volume of 100 µL to individual wells of an antibody pre-coated 96-well tray provided with the kit. After an hour incubation at room temperature, the wells are washed with the wash buffer 3 times (PBS containing 0.05% TWEEN®) to remove unbound laminin. The peroxidase-conjugated laminin antibody is then added to the antibody-laminin complex in the wells in a 100 µL volume and allowed to bind at room temperature for 1 hour. The 96-well plate is washed repeatedly (4×) to remove any unbound enzyme/antibody conjugate. The chromogenic substrate+H202 is added to each of the wells in a 100 µL volume. The reaction is allowed to proceed for 30 minutes at room temperature. The reaction is terminated by addition of 100 µL of 2.5N sulfuric acid. Absorbance is measured at 450 nm. Samples of solubilized membrane are tested at a concentration of 1000 ng/mL. Each membrane sample is tested in triplicate. Laminin concentration is presented as a concentration of total membrane weight as shown below.

In yet other embodiments, the invention encompasses assays for determining the total fibronectin content of the collagen compositions of the invention using methods known in the art and exemplified herein. An exemplary assay for determining the total fibronectin content of a collagen composition of the invention may comprise the following: a sandwich ELISA assay provided as a kit from Takara Blo Inc., Shiga, Japan (Cat # MK1 15) may be used. The kit includes a 96-well plate pre-coated with the primary (Capture Antibody), a murine monoclonal antibody to human fibronectin. The secondary antibodies (Detection antibody) and human fibronectin standards are provided with the kit. The detection antibody is a conjugated human fibronectin antibody with horseradish peroxidase. The enzymatic reaction with a chromogenic substrate tetramethylbenzidine and H202 gives a blue color, which is detected via UV-Vis spectroscopy at 450 nm. To quantitate the amount of fibronectin, a standard calibration curve is developed with a sample of a series of human fibronectin standards of known concentrations (provided with kit). The concentration of fibronectin in a test sample is determined by referencing to the standard curve. Assay protocols are developed as per the recommendations of the ELISA kit. To develop a standard calibration curve, the human fibronectin standard is added in increasing concentrations of 12.5 ng/mL to 400 ng/mL in a final volume of 100 µL to individual wells of an antibody pre-coated 96-well tray provided with the kit. After a 1 hr incubation at room temperature, the wells are washed with the wash buffer 3 times (PBS containing 0.05% TWEEN®) to remove unbound fibronectin. The peroxidase-conjugated fibronectin antibody is then added to the antibody-fibronectin complex in the wells in a 100 µL volume and allowed to bind at room temperature for 1 hour. The 96-well plate is washed repeatedly (4×) to remove any unbound enzyme/antibody conjugate. The chromogenic substrate+H202 is added to each of the wells in a 100 µL volume. The reaction is allowed to proceed for 30 minutes at room temperature. The reaction is terminated by addition of 100 µL of 2.5N sulfuric acid. Absorbance is measured at 450 nm. Samples of solubilized membrane are tested at a concentration of 1000 µg/mL. Each membrane sample is tested in triplicate.

6.4.2. Biocompatibility Studies

The collagen composition of the invention are of biological origin and contain significant amounts of collagen. However, unlike collagen derived from animal sources (bovine and porcine), human collagen is non-immunogenic. Because non-immunogenic human tissue is inherently biocompatible with other human tissue, it is not necessary to perform several of the standard biocompatibility tests (e.g., dermal irritation and sensitization, acute systemic toxicity). The invention encompasses assays for determining the biocompatibility of the collagen composition of the invention. Biocompatibility as used herein refers to the property of being biologically compatible by not producing a toxic, injurious, or immunological response or rejection in living tissue. Bodily response to unknown materials is a principal concern when using artificial materials in the body and hence the biocompatibility of a material is an important design consideration in such materials. The biocompatibility assays encompassed within the invention include but are not limited to cytotoxicity assays, rabbit eye irritation tests, hemolysis assays and pyrogencity assays. Biocompatibility assays of the invention are cell-based or cell-free based assay.

In yet another specific embodiment, the cytotoxicity of the collagen composition of the invention is determined using an ISO MEM Elution test (Example 6.4.2.2). The purpose of this study is to evaluate the ability of collagen composition to elicit a cytotoxic response in cultured mouse fibroblast cells. In an exemplary assay, Eagle's Minimal Essential medium (E-MEM) supplemented with 5% Fetal Bovine Serum (FBS) is used to extract test samples. The medium is also supplemented with one or more of the following: L-glutamine, HEPES, gentamicin, penicillin, vancomycin, and amphotericin B (fungizone). Cultures of L-929 cells (mouse fibroblasts) are grown and used as monolayers in disposable tissue culture labware at 37±1° C. in a humidified atmosphere of 5±1% carbon dioxide in air. Test samples are extracted intact using a ratio equivalent of 120 $cm^2$ sample and 20 ml-E-MEM plus 5% FBS. Test samples are extracted in E-MEM plus 5% FBS at 37±1° C. in 5±1% carbon dioxide for 24-25 hours. After the extraction period, the maintenance culture medium is removed from test culture wells and replaced with 1 ml of the test media/extract and control media/extracts and positive control media spiked with cadmium chloride. Positive, intermediate and negative controls are run in parallel with the test samples. The test media/extract and control media/extract and positive control media spiked with cadmium chloride are plated in triplicate and incubated 72±4 hours at 37±1° C. In a humidified atmosphere of 5±1% carbon dioxide in air.

Cultures are evaluated for cytotoxic effects by microscopic observation at 24, 48 and 72±4 hour incubation periods. Criteria for evaluating cytotoxicity will include morphological changes in cells, such as granulation, crenation or rounding, and loss of viable cells from the monolayer by lysis or detachment. The validity of the test requires that negative control cultures maintain a healthy normal appearance throughout the duration of the test. Degrees of toxicity are scored, as follows:

0 None: Discrete intracytoplasmic granules; no cell lysis.

1 Slight: Not more than 20% of the cells are round, loosely attached, and without intracytoplasmic granules; occasional lysed cells are present.

2 Mild: Not more than 50% of the cells are round and devoid of intra-cytoplasmic granules; no extensive cell lysis and empty areas between cells.

3 Moderate: Not more than 70% of the cell layers contain rounded cells and/or are lysed.

4 Severe: Nearly complete destruction of the cell layers.

According to the USP, test articles scoring "0", "1" or "2" will be considered non-toxic. Test articles scoring "3" or "4" will be considered toxic. The positive control sample must have a score of "3" or "4" and the negative control sample must have a score of "0" for a valid test.

The ocular surface of the rabbit is known to be more sensitive than human skin, therefore rabbit eye irritation studies are used to assess the biocompatibility of a collagen composition of the invention. In an exemplary assay, samples are screened for primary ocular irritation. The amniotic membrane is cleaned using an aqueous solution of 0.05% deoxycholic acid monohydrate sodium salt (D-Cell). The test can be conducted in accordance with the guidelines of the Federal Hazardous Substances Act (FHSA) Regulations, 16 CFR 1500. In an exemplary assay, control eyes are judged clinically normal for rabbits by gross examination with an auxiliary light source. To detect any pre-existing corneal injury the eyes are treated with fluorescein stain, flushed with 0.9% USP physiological saline solution (PSS), and observed with ultraviolet light in a darkened room. A sample is instilled into the lower conjunctival sac of one eye of each rabbit according to standard techniques. The opposite eye of each rabbit remains untreated and serves as the comparative control. Animals are returned to their cages following treatment. At 24, 48, and 72 hours after dosing the test eye of each rabbit is examined with an auxiliary light source and appropriate magnification compared to the untreated control eye, and graded for ocular irritation. To detect or confirm corneal injury the test eyes are treated with fluorescein stain, flushed with PSS, and examined in darkened conditions with an ultraviolet lamp at 24 hours. Reactions are scored in accordance with the FHSA-modified Draize scoring criteria. One of three animals exhibiting a significant positive reaction is a borderline finding. Two of three animals exhibiting a significant positive reaction is a significant positive response and the test article is considered an irritant.

The invention encompasses determining the hemolytic properties of a collagen composition of the invention using methods known in the art and exemplified herein (See Example 6.4.2.4). Hemolysis describes the hemolytic properties of a test sample that will contact blood. It is regarded as an especially significant screening test to perform because it measures red blood cell membrane fragility in contact with materials and devices. In an exemplary assay, the procedure involves exposing the test material to a blood cell suspension and then determining the amount of hemoglobin released. The test is run under static conditions with direct contact of the test sample with human blood. The amount of hemoglobin released by the red blood cells is measured spectrophotometrically at 540 nm (following conversion to cyanomethemoglobin) concurrently with the negative and positive controls. The hemolytic index for the samples and controls is calculated as follows:

Hemolytic Index=Hemoglobin Released (mg/mL)×100 Hemoglobin Present (mg/mL)

Where: Hemoglobin Released (mg/ml)=(Constant+X Coefficient)×Optical Density×16. Hemoglobin Present (mg/mL)=Diluted Blood 10±1 mg/mL The invention encompasses methods for determining the pyrogenicity of the collagen composition of the invention using methods known in the art and exemplified herein (See Example 6.4.2.5). In one embodiment, the pyrogenicity of the collagen composition of the invention is determined by measuring the presence of bacterial endotoxin in the collagen composition of the invention using for example the *Limulus Amebocyte* Lysate (LAL) test. This test is an in vitro assay for detection and quantification of bacterial endotoxin. In an exemplary test, ninety-eight samples of collagen composition (n=1 per lot), each measuring 1×2 cm, are tested individually for extraction. The extractions are performed by washing each sample in 30 mL of extraction fluid for 40 to 60 minutes at 37 to 40° C. with intermittent swirling on an orbital shaker. The pH of each sample extract is between 6 and 8 as verified with pH paper. Pyrogen levels are measured by a Kinetic Turbidimetric Colorimetric Test with a test sensitivity of 0.05 Endotoxin Units (EU) per mL. Total endotoxin level per sample is calculated by multiplying the detected endotoxin value (EU/mL) by 30 mL (extraction volume per device) and again by twenty-four (to simulate a 6×8 cm-sized device).

6.4.3. Microbiological Studies

The invention encompasses methods known in the art and exemplified herein to determine the presence of microbiological organisms including but not limited to *Escherichia coli, Klebsiella pneumoniae, Staphylococcus aureus, Enterococcus faecalis, Candida albicans, Proteus vulgaris, Staphylococcus viridans*, and *Pseudomonas aeruginosa* in a collagen composition of the invention. Such methods may be used at any step of the preparation of the collagen composition. An exemplary process for microbiology studies during processing comprises the following: Testing of microbiologically "spiked' samples of unprocessed amniotic membrane and equipment used during the processing. Samples are immersed for five minutes in saline spiked with eight microorganisms as follows to deliberately contaminate the sample:

1. *Escherichia coli*
2. *Klebsiella pneumoniae*
3. *Staphylococcus aureus*
4. *Enterococcus faecalis*
5. *Candida albicans*
6. *Proteus vulgaris*
7. *Staphylococcus viridans*
8. *Pseudomonas aeruginosa*

Advantageously, the decellularization and rinsing methods of the invention can reduce the number of microorganisms on the collagen composition of the invention.

The invention encompasses methods known in the art and exemplified herein to determine the bioburden of the collagen compositions of the invention. As used herein, "bioburden" is a measure of the contaminating organisms found on a given amount of material before it undergoes an industrial sterilization process. In an exemplary method, the minimum E-beam radiation dose that would achieve sterility with a Sterilization Assurance Level of 10-6 is determined. Membranes are extracted by immersion and manual shaking using PEPTONE-TWEEN® Solution. Plating method is membrane filtration using soybean-casein digest agar. For aerobic conditions plates are incubated 4 days at 30-35° C. then enumerated. For fungi, plates are incubated four days at 20-25° C. then enumerated. For spore-forming bacteria, the extract portion is heat shocked, filtered and plated as for aerobic bacteria. Plates are incubated 4 days at 30-35° C., then enumerated for anaerobic bacteria, plates were incubated under anaerobic conditions for 4 days at 30-35° C. then enumerated. Microorganisms utilized are *Clostridium sporogenes, Pseudomonas aeruginosa,* and *Bacillus atrophaeus.*

In particular embodiments, the collagen compositions of the invention have less than 2 colony forming units (cfu) for aerobes and fungi, less than 1, or zero cfu for aerobes and fungi. In yet other embodiments, the collagen compositions of the invention have less than 5.1 Colony Forming Units (cfu), less than 2, or less than 1 cfu for anaerobes and spores.

In particular embodiments, the collagen composition of the invention is not bacteriostatic or fungistatic as determined using methods exemplified herein and known to one skilled in the art (See Example 6.4.3.2). As used herein bacteriostatic refers to an agent that inhibits bacterial growth or reproduction but does not kill bacteria. As used herein fungistatic refers to an agent that prevents the growth of a fungus by the presence of a non-fungicidal chemical or physical agency.

6.4.4. Storage and Handling of the Collagen Composition

The invention encompasses storing the collagen composition of the invention at room temperature (e.g., 25° C.). In certain embodiments, the collagen composition of the invention can be stored at a temperature of at least 0° C., at least 4° C., at least 10° C., at least 15° C., at least 20° C., at least 25° C., at least 30° C., at least 35° C. or at least 40° C. In some embodiments, the collagen composition of the invention is not refrigerated. In some embodiments, the collagen composition of the invention may be refrigerated at a temperature of about 2 to 8° C. In other embodiments, the collagen composition of the invention can be stored at any of the above-identified temperatures for an extended period of time. In a particular embodiment, the collagen composition of the invention is stored under sterile and non-oxidizing conditions. In certain embodiments, the collagen composition produced according to the methods of the invention can be stored at any of the specified temperatures for 12 months or more with no alteration in biochemical or structural integrity (e.g., no degradation), without any alteration of the biochemical or biophysical properties of the collagen composition. In certain embodiments, the collagen composition produced according to the methods of the invention can be stored for several years with no alteration in biochemical or structural integrity (e.g., no degradation), without any alteration of the biochemical or biophysical properties of the collagen composition. In certain embodiments, it is expected that the collagen composition of the invention prepared in accordance with the methods of the invention will last indefinitely. The collagen composition may be stored in any container suitable for long-term storage. Advantageously, the collagen composition of the invention can be stored in a sterile double peel-pouch package.

6.4.5. Sterilization

The collagen compositions of the invention can be sterilized according to techniques known to those of skill in the art for sterilizing such compositions.

In certain embodiments, the collagen composition is filtered through a filter that allows passage of endotoxins and retains the collagen composition. Any filter of a size, for example 30 kDa, known to those of skill in the art for filtration of endotoxins can be used. In certain embodiments, the collagen composition is contacted with the filter under conditions that allow endotoxins to pass through the filter while retaining a collagen composition. The conditions can be any conditions for filtration known to those of skill in the art, for instance, centrifugation or pumping. The filter should be of a size that retains collagen while allowing endotoxins to pass the filter. In certain embodiments, the filter is between 5 kDa and 100 kDa. In particular embodiments, the filter is about 5 kDa, about 10 kDa, about 15 kDa, about 20 kDa, about 30 kDa, about 40 kDa, about 50 kDa, about 60 kDa, about 70 kDa, about 80 kDa, about 90 kDa or about 100 kDa. The filter can be of any material known to those of skill in the art to be compatible with a collagen composition such as cellulose, polyethersulfone and others apparent to those of skill. The filtration can be repeated as many times as desired by one of skill in the art. Endotoxin can be detected according to standard techniques to monitor clearance.

In certain embodiments, the collagen composition can be filtered to generate collagen compositions free of, or reduced in, viral particles. Advantageously, in these embodiments of the invention, the filter retains a collagen composition while allowing viral particles to pass through. Any filter known to those of skill in the art to be useful for clearing viruses can be used. For instance, a 1000 kDa filter can be used for clearance, or reduction, of parvovirus, hepatitis A virus and HIV. A 750 kDa filter can be used for clearance, or reduction, of parvovirus and hepatitis A virus. A 500 kDa filter can be used for clearance, or reduction, of parvovirus.

Accordingly, the present invention provides methods of producing collagen compositions free of, or reduced in viral particles, comprising the step of contacting a collagen composition with a filter of a size that allows one or more viral particles to pass through the filter while retaining the collagen composition. In certain embodiments, the collagen composition is contacted with the filter under conditions that allow one or more viral particles to pass through the filter while retaining a collagen composition. The conditions can be any conditions for filtration known to those of skill in the art, for instance, centrifugation or pumping. The filter should be of a size that retains collagen while allowing one or more viral particles to pass the filter. In certain embodiments, the filter is between 500 kDa and 1000 kDa. In particular embodiments, the filter is about 500 kDa, about 750 kDa or about 1000 kDa. The filter can be of any material known to those of skill in the art to be compatible with a collagen composition such as cellulose, polyethersulfone and others apparent to those of skill. The filtration can be repeated as many times as desired by one of skill in the art. Viral particles can be detected according to standard techniques to monitor filtration.

Sterilization of a collagen composition of the invention can also be carried out by electron beam irradiation using methods known to one skilled in the art, e.g., Gorham, D. Byrom (ed.), 1991, *Biomaterials*, Stockton Press, New York, 55-122. Any dose of radiation sufficient to kill at least 99.9% of bacteria or other potentially contaminating organisms is within the scope of the invention. In a particular embodiment, a dose of at least 18-25 kGy is used to achieve the terminal sterilization of a collagen composition of the invention.

6.5 Formulations of the Collagen Compositions

In certain embodiments, the present invention provides collagen compositions. The collagen can be any collagen of the invention, for instance collagen prepared by one of the methods herein. Advantageously, the collagen can be formulated in water or phosphate buffered saline. In particular embodiments, the collagen is formulated in phosphate buffered saline.

The collagen can be at any concentration useful to those of skill in the art. In certain embodiments, the formulations of the invention comprise 0.1-100 mg/ml, 1-100 mg/ml, 1-75 mg/ml, 1-50 mg/ml, 1-40 mg/ml, 10-40 mg/ml or 20-40 mg/ml collagen. In certain embodiments, the formulations of the invention comprise about 5 mg/ml, 10 mg/ml, 15 mg/ml, 20 mg/ml, 25 mg/ml, 30 mg/ml, 35 mg/ml, 40 mg/ml, 45 mg/ml or 50 mg/ml collagen. In a particular embodiment, the present invention provides formulations comprising about 35 mg/ml collagen.

In certain embodiments of the invention, a collagen composition can be dried and shaped into a shape useful for one of skill in the art. The shape can be any useful shape including sheets, tubes, plugs, spheres and the like. In certain embodiments, the collagen composition is shaped to fit a site of a wound or injury. The shaped collagen composition can be used for any purpose apparent to those of skill in the art. Exemplary methods of using shaped collagen compositions are provided below.

The composition of the invention, as extracted from the placenta, is typically a white paste. This past can be shaped according to any methods known in the art for shaping such materials. For example, the composition can be forced into a mold, or formed around a mold, to produce specific shapes, and heat-dried, vacuum-dried or freeze-dried. The composition can also be spread thin and dried on, e.g., a gel dryer, e.g., using vacuum.

In certain embodiments, the compositions of the present invention may be combined with pharmaceutically or cosmetically acceptable carriers and administered as compositions in vitro or in vivo. Forms of administration include, but are not limited to, injections, solutions, creams, gels, implants, pumps, ointments, emulsions, suspensions, microspheres, particles, microparticles, nanoparticles, liposomes, pastes, patches, tablets, transdermal delivery devices, sprays, aerosols, or other means familiar to one of ordinary skill in the art. Such pharmaceutically or cosmetically acceptable carriers are commonly known to one of ordinary skill in the art. Pharmaceutical formulations of the present invention can be prepared by procedures known in the art using well known and readily available ingredients. For example, the compounds can be formulated with common excipients, diluents, or carriers, and formed into tablets, capsules, suspensions, powders, and the like. Examples of excipients, diluents, and carriers that are suitable for such formulations include the following: fillers and extenders (e.g., starch, sugars, mannitol, and silicic derivatives); binding agents (e.g., carboxymethyl cellulose and other cellulose derivatives, alginates, gelatin, and polyvinyl-pyrrolidone); moisturizing agents (e.g., glycerol); disintegrating agents (e.g., calcium carbonate and sodium bicarbonate); agents for retarding dissolution (e.g., paraffin); resorption accelerators (e.g., quaternary ammonium compounds); surface active agents (e.g., cetyl alcohol, glycerol monostearate); adsorptive carriers (e.g., kaolin and bentonite); emulsifiers; preservatives; sweeteners; stabilizers; coloring agents; perfuming agents; flavoring agents; lubricants (e.g., talc, calcium and magnesium stearate); solid polyethyl glycols; and mixtures thereof.

The terms "pharmaceutically or cosmetically acceptable carrier" or "pharmaceutically or cosmetically acceptable vehicle" are used herein to mean, without limitations, any liquid, solid or semi-solid, including, but not limited to, water or saline, a gel, cream, salve, solvent, diluent, fluid ointment base, ointment, paste, implant, liposome, micelle, giant micelle, and the like, which is suitable for use in contact with living animal or human tissue without causing adverse physiological or cosmetic responses, and which does not interact with the other components of the composition in a deleterious manner. Other pharmaceutically or cosmetically acceptable carriers or vehicles known to one of skill in the art may be employed to make compositions for delivering the molecules of the present invention.

The formulations can be so constituted that they release the active ingredient only or preferably in a particular location, possibly over a period of time. Such combinations provide yet a further mechanism for controlling release kinetics. The coatings, envelopes, and protective matrices may be made, for example, from polymeric substances or waxes.

Methods of in vivo administration of the compositions of the present invention, or of formulations comprising such compositions and other materials such as carriers of the present invention that are particularly suitable for various forms include, but are not limited to, oral administration (e.g. buccal or sublingual administration), anal administration, rectal administration, administration as a suppository, topical application, aerosol application, inhalation, intraperitoneal administration, intravenous administration, transdermal administration, intradermal administration, subdermal administration, intramuscular administration, intrauterine administration, vaginal administration, administration into a body cavity, surgical administration at the location of a tumor or internal injury, administration into the lumen or parenchyma of an organ, and parenteral administration. Techniques useful in the various forms of administrations above include but are not limited to, topical application, ingestion, surgical administration, injections, sprays, transdermal delivery devices, osmotic pumps, electrodepositing directly on a desired site, or other means familiar to one of ordinary skill in the art. Sites of application can be external, such as on the epidermis, or internal, for example a gastric ulcer, a surgical field, or elsewhere.

The collagen compositions of the present invention can be applied in the form of creams, gels, solutions, suspensions, liposomes, particles, or other means known to one of skill in the art of formulation and delivery of therapeutic and cosmetic compounds. Ultrafine particle sizes of collagen materials can be used for inhalation delivery of therapeutics. Some examples of appropriate formulations for subcutaneous administration include but are not limited to implants, depot, needles, capsules, and osmotic pumps. Some examples of appropriate formulations for vaginal administration include but are not limited to creams and rings. Some examples of appropriate formulations for oral administration include but are not limited to: pills, liquids, syrups, and suspensions. Some examples of appropriate formulations for transdermal administration include but are not limited to gels, creams, pastes, patches, sprays, and gels. Some examples of appropriate delivery mechanisms for subcutaneous administration include but are not limited to implants, depots, needles, capsules, and osmotic pumps. Formulations suitable for parenteral administration include but are not limited to aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. Extemporaneous injection solutions and suspensions may be prepared from sterile powders, granules and tablets commonly used by one of ordinary skill in the art.

Embodiments in which the compositions of the invention are combined with, for example, one or more "pharmaceutically or cosmetically acceptable carriers" or excipients may conveniently be presented in unit dosage form and may be prepared by conventional pharmaceutical techniques. Such techniques include the step of bringing into association the compositions containing the active ingredient and the pharmaceutical carrier(s) or excipient(s). In general, the formulations are prepared by uniformly and intimately bringing into association the active ingredient with liquid carriers. Particular unit dosage formulations are those containing a dose or unit, or an appropriate fraction thereof, of the administered ingredient. It should be understood that in addition to the ingredients particularly mentioned above, formulations comprising the compositions of the present invention may include other agents commonly used by one of ordinary skill in the art. The volume of administration will vary depending on the route of administration. For example, intramuscular injections may range in volume from about 0.1 ml to 1.0 ml.

The compositions of the present invention may be administered to persons or animals to provide substances in any dose range that will produce desired physiological or pharmacological results. Dosage will depend upon the substance or substances administered, the therapeutic endpoint desired, the desired effective concentration at the site of action or in a body fluid, and the type of administration. Information regarding appropriate doses of substances are known to persons of ordinary skill in the art and may be found in references such as L. S. Goodman and A. Gilman, eds, The Pharmacological Basis of Therapeutics, Macmillan Publishing, New York, and Katzung, Basic & Clinical Pharmacology, Appleton & Lang, Norwalk, Conn., ($6^{th}$ Ed. 1995). A clinician skilled in the art of the desired therapy may chose specific dosages and dose ranges, and frequency of administration, as required by the circumstances and the substances to be administered.

The collagen composition may comprise one or more compounds or substances that are not collagen. For example, the collagen composition may be impregnated, either during production or during preparation for surgery, with a biomolecule. Such biomolecules include but are not limited to, antibiotics (such as Clindamycin, Minocycline, Doxycycline, Gentamycin), hormones, growth factors, anti-tumor agents, anti-fungal agents, anti-viral agents, pain medications, anti-histamines, anti-inflammatory agents, anti-infectives including but not limited to silver (such as silver salts, including but not limited to silver nitrate and silver sulfadiazine), elemental silver, antibiotics, bactericidal enzymes (such as lysozome), wound healing agents (such as cytokines including but not limited to PDGF, TGF; thymosin), hyaluronic acid as a wound healing agent, wound sealants (such as fibrin with or without thrombin), cellular attractant and scaffolding reagents (such as fibronectin) and the like. In a specific example, the collagen composition may be impregnated with at least one growth factor, for example, fibroblast growth factor, epithelial growth factor, etc. The collagen composition may also be impregnated with small organic molecules such as specific inhibitors of particular biochemical processes e.g., membrane receptor inhibitors, kinase inhibitors, growth inhibitors, anticancer drugs, antibiotics, etc.

In yet other embodiments, the collagen composition of the invention may be combined with a hydrogel. Any hydrogel composition known to one skilled in the art is encompassed within the invention, e.g., any of the hydrogel compositions disclosed in the following reviews: Graham, 1998, Med. Device Technol. 9(1): 18-22; Peppas et al., 2000, Eur. J. Pharm. Biopharm. 50(1): 27-46; Nguyen et al., 2002, Biomaterials, 23(22): 4307-14; Henincl et al., 2002, Adv. Drug Deliv. Rev 54(1): 13-36; Skelhorne et al., 2002, Med. Device. Technol. 13(9): 19-23; Schmedlen et al., 2002, Biomaterials 23: 4325-32; all of which are incorporated herein by reference in their entirety. In a specific embodiment, the hydrogel composition is applied on the collagen composition, i.e., discharged on the surface of the collagen composition. The hydrogel composition for example, may be sprayed onto the collagen composition, saturated on the surface of the collagen composition, soaked with the collagen composition, bathed with the collagen composition or coated onto the surface of the collage collagen composition.

The hydrogels useful in the methods and compositions of the invention can be made from any water-interactive, or water soluble polymer known in the art, including but not limited to, polyvinylalcohol (PVA), polyhydroxyehthyl methacrylate, polyethylene glycol, polyvinyl pyrrolidone, hyaluronic acid, dextran or derivatives and analogs thereof.

In some embodiments, the collagen composition of the invention is further impregnated with one or more biomolecules prior to being combined with a hydrogel. In other embodiments, the hydrogel composition is further impregnated with one or more biomolecules prior to being combined with a collagen composition of the invention. Such biomolecules include but are not limited to, antibiotics (such as Clindamycin, Minocycline, Doxycycline, Gentamycin), hormones, growth factors, anti-tumor agents, anti-fungal agents, anti-viral agents, pain medications, anti-histamines, anti-inflammatory agents, anti-infectives including but not limited to silver (such as silver salts, including but not limited to silver nitrate and silver sulfadiazine), elemental silver, antibiotics, bactericidal enzymes (such as lysozome), wound healing agents (such as cytokines including but not limited to PDGF, TGF; thymosin), hyaluronic acid as a wound healing agent, wound sealants (such as fibrin with or without thrombin), cellular attractant and scaffolding reagents (such as fibronectin) and the like. In a specific example, the collagen composition or the hydrogel composition may be impregnated with at least one growth factor, for example, fibroblast growth factor, epithelial growth factor, etc. Advantageously, the biomolecule can be a therapeutic agent.

In some embodiments, the hydrogel composition is combined with a laminate comprising the collagen composition of the invention.

The hydrogel/collagen composition has utility in the medical field including but not limited to, treatment of wounds, burns, and skin conditions (e.g., to treat scarring), cosmetic uses (e.g., cosmetic surgery), and any use as an implant. In some embodiments, the hydrogel/collagen composition is applied topically to a subject, i.e., on the surface of the skin, for example, for the treatment of a wound. In other embodiments, the hydrogel/collagen composition may be used in the interior of a subject, for example as an implant, to become a permanent or semi-permanent structure in the body. In some embodiments, the hydrogel compositions in formulated to be non-biodegradable. In yet other embodiments, the hydrogel composition is formulated to be biodegradable. In a specific embodiment, the hydrogel composition is formulated to degrade within days. In another specific embodiment, the hydrogel composition is formulated to degrade within months.

In some embodiments, the collagen composition of the invention is populated with cells, so that the cells are uniform and confluent. Cells that can be used to populate a collagen composition of the invention include but are not limited to, stem cells, human stem cells, human differentiated adult cells, totipotent stem cells, pluripotent stem cells, multipotent stem cells, tissue specific stem cells, embryonic like stem cells, committed progenitor cells, fibroblastoid cells. In other embodiments, the invention encompasses populating the collagen composition of the invention with specific classes of progenitor cells including but not limited to chondrocytes, hepatocytes, hematopoietic cells, pancreatic parenchymal cells, neuroblasts, and muscle progenitor cells.

6.6 Stem Cells

In certain embodiments, the collagen compositions of the present invention comprise a plurality of stem cells. The stem cells can be any stem cells suitable for a given purpose, and can be totipotent or pluripotent stem cells, or can be progenitor cells. Preferably, the composition comprises placental stem cells such as those described in U.S. Application Publication Nos. 2003/0032179 and 2003/0180269, and in U.S. Pat. No. 7,045,148. However, the composition can comprise stem or progenitor cells, preferably mammalian stem or progenitor cells, from any tissue source, e.g., embryonic stem cells, embryonic germ cells, mesenchymal stem cells, bone marrow-derived stem cells, hematopoietic progenitor cells (e.g., hematopoietic stem cells from peripheral blood, fetal blood, placental blood, umbilical cord blood, placental perfusate, etc.), somatic stem cells, neural stem cells, hepatic stem cells, pancreatic stem cells, endothelial stem cells, cardiac stem cells, muscle stem cells, adipose stem cells, and the like. The composition can comprise any combination of types of stem cells. In preferred embodiments, the stem cells are human stem cells, e.g., human placental stem cells.

Generally, the composition of the invention is contacted with a plurality of stem or progenitor cells for a time sufficient for a plurality of said stem or progenitor cells to attach to the composition. In preferred embodiments, the composition of the invention is shaped into a useful configuration, e.g., sheet, plug, tube, or other configuration, prior to contacting with the stem or progenitor cells. Contacting the stem or progenitor cells with the composition of the invention can be effected by any method known in the art, and comprise, e.g., dispensing medium comprising the stem or progenitor cells onto the surface of the composition; immersing a part or a whole of the composition in a suspension of the stem or progenitor cells; culturing a plurality of the stem or progenitor cells on the surface of the composition for a time sufficient for the plurality to proliferate for at least one cell division; and the like. The stem cells, preferably placental stem cells, can be present on the composition of the invention, e.g., a shaped form of the composition, on the entirety or a portion of the composition surface, e.g., can be present randomly on the surface, confluently, etc.

The number of stem or progenitor cells contacted with the composition of the invention in any embodiment may vary, but may be at least $1 \times 10^6$, $3 \times 10^6$, $1 \times 10^7$, $3 \times 10^7$, $1 \times 10^8$, $3 \times 10^8$, $1 \times 10^9$, $3 \times 10^9$, $1 \times 10^{10}$, $3 \times 10^{10}$, $1 \times 10^{11}$, $3 \times 10^{11}$, or $1 \times 10^{12}$; or may be no more than $1 \times 10^6$, $3 \times 10^6$, $1 \times 10^7$, $3 \times 10^7$, $1 \times 10^8$, $3 \times 10^8$, $1 \times 10^9$, $3 \times 10^9$, $1 \times 10^{10}$, $3 \times 10^{10}$, $1 \times 10^{11}$, $3 \times 10^{11}$, or $1 \times 10^{12}$ stem or progenitor cells.

In certain other embodiments, the composition of the invention comprises one or more types of extracellular matrix protein deposited by a stem cell. In one embodiment, for example, a collagen composition of the invention is made to comprise extracellular matrix proteins by contacting a collagen composition of the invention with a plurality of stem cells; culturing the stem cells on the composition for a time sufficient for the stem cells to deposit a detectable amount of at least one type of extracellular matrix protein; and decellularizing the composition to produce a collagen composition comprising at least one type of extracellular matrix protein. In one embodiment, therefore, the composition of the invention comprises a decellularized extracellular matrix, wherein the decellularized extracellular matrix is deposited or produced by stem cells. In various embodiments, the extracellular matrix protein is collagen (Type I, II, III, and/or IV), elastin or fibronectin. In another embodiment, the extracellular matrix protein is produced by a plurality of stem cells that are proliferating and not differentiating. In another embodiment, the extracellular matrix is produced by a plurality of stem cells that are differentiating, or by a plurality of cells that have differentiated from a plurality of stem cells. In a specific embodiment of the above embodiments, the stem cells are placental stem cells, e.g., CD34$^-$ placental stem cells or CD200$^+$ placental stem cells.

6.6.1. Placental Stem Cells

In a preferred embodiment, the composition comprises a plurality of CD34$^-$ placental stem cells. CD34$^-$ placental stem cells are stem cells, obtainable from placental tissue, that adhere to a tissue culture substrate and have the capacity to differentiate into non-placental cell types. Placental stem cells can be either fetal or maternal in origin (that is, can have the genotype of either the mother or fetus). Populations of placental stem cells, or populations of cells comprising placental stem cells, can comprise placental stem cells that are solely fetal or maternal in origin, or can comprise a mixed population of placental stem cells of both fetal and maternal origin. The placental stem cells, and populations of cells comprising the placental stem cells, can be identified and selected by the morphological, marker, and culture characteristic discussed below.

The placental stem cells, when cultured in primary cultures or in cell culture, adhere to the tissue culture substrate, e.g., tissue culture container surface (e.g., tissue culture plastic). Placental stem cells in culture assume a generally fibroblastoid, stellate appearance, with a number of cyotplasmic processes extending from the central cell body. The placental stem cells are, however, morphologically differentiable from fibroblasts cultured under the same conditions, as the placental stem cells exhibit a greater number of such processes than do fibroblasts. Morphologically, placental stem cells are also distinguishable from hematopoietic stem cells, which generally assume a more rounded, or cobblestone, morphology in culture.

The placental stem cells generally express the markers CD10, CD73, CD105, CD200, HLA-G, and/or OCT-4, and do not express CD34, CD38, or CD45. Placental stem cells can also express HLA-ABC (MHC-1) and HLA-DR. Thus, in one embodiment, the stem cells that can be combined with the compositions of the invention are CD200$^+$ or HLA-G$^+$. In another embodiment, the placental stem cells are CD73$^+$, CD105$^+$, and CD200$^+$. In another embodiment, the placental stem cell that is CD200$^+$ and OCT-4$^+$. In another embodiment, the placental stem cells are CD73$^+$, CD105$^+$ and HLA-G$^+$. In another embodiment, the placental stem cells are CD73$^+$ and CD105$^+$, and, when in a population of placental cells, facilitate formation of one or more embryoid-like bodies under conditions that allow formation of embryoid-like bodies. In another embodiment, the placental stem cells are OCT-4$^+$ and, when in a population of placental cells, facilitate formation of one or more embryoid-like bodies in a population of isolated placental cells comprising said stem cell when cultured under conditions that allow formation of embryoid-like bodies.

The placental stem cells can be obtained by perfusion. For example, the invention provides an isolated population of placental stem cells that is produced according to a method comprising perfusing a mammalian placenta that has been drained of cord blood and perfused to remove residual blood; perfusing said placenta with a perfusion solution; and collecting said perfusion solution, wherein said perfusion solution after perfusion comprises a population of placental cells that comprises placental stem cells; and isolating a plurality of said placental stem cells from said population of cells. In a specific embodiment, the perfusion solution is passed through both the umbilical vein and umbilical arteries and collected after it exudes from the placenta. Populations of placental stem cells produced by this method typically comprise a mixture of fetal and maternal cells. In another specific embodiment, the perfusion solution is passed through the umbilical vein and collected from the umbilical arteries, or passed through the umbilical arteries and collected from the umbilical vein. Populations of placental stem cells produced by this method typically are substantially exclusively fetal in origin; that is, e.g., greater than 90%, 95%, 99%, or 99.5% of the placental stem cells in the population are fetal in origin.

In various embodiments, the placental stem cells, contained within a population of cells obtained from perfusion of a placenta, are at least 50%, 60%, 70%, 80%, 90%, 95%, 99% or at least 99.5% of said population of placental cells. In another specific embodiment, the placental stem cells collected by perfusion comprise fetal and maternal cells. In another specific embodiment, the placental stem cells collected by perfusion are at least 50%, 60%, 70%, 80%, 90%, 95%, 99% or at least 99.5% fetal cells.

Placental stem cells can also be collected from a mammalian placenta by physical disruption, e.g., enzymatic digestion, of the organ or a portion thereof. For example, the placenta, or a portion thereof, may be, e.g., crushed, sheared, minced, diced, chopped, macerated or the like, while in contact with the stem cell collection composition of the invention, and the tissue subsequently digested with one or more enzymes. The placenta, or a portion thereof, may also be physically disrupted and digested with one or more enzymes, and the resulting material then immersed in, or mixed into, the stem cell collection composition of the invention. Any method of physical disruption can be used, provided that the method of disruption leaves a plurality, more preferably a majority, and more preferably at least 60%, 70%, 80%, 90%, 95%, 98%, or 99% of the cells in said organ viable, as determined by, e.g., trypan blue exclusion.

The placenta can be dissected into components prior to physical disruption and/or enzymatic digestion and stem cell recovery. For example, placental stem cells can be obtained from the amniotic membrane, chorion, umbilical cord, placental cotyledons, or any combination thereof. Preferably, placental stem cells are obtained from placental tissue comprising amnion and chorion. Typically, placental stem cells can be obtained by disruption of a small block of placental tissue, e.g., a block of placental tissue that is about 1, 2, 3, 4, 5, 6, 7, 8, 9, 10, 20, 30, 40, 50, 60, 70, 80, 90, 100, 200, 300, 400, 500, 600, 700, 800, 900 or about 1000 cubic millimeters in volume.

A preferred stem cell collection composition comprises one or more tissue-disruptive enzyme(s). Enzymatic digestion preferably uses a combination of enzymes, e.g., a combination of a matrix metalloprotease and a neutral protease, for example, a combination of collagenase and dispase. In one embodiment, enzymatic digestion of placental tissue uses a combination of a matrix metalloprotease, a neutral protease, and a mucolytic enzyme for digestion of hyaluronic acid, such as a combination of collagenase, dispase, and hyaluronidase or a combination of LIBERASE (Boehringer Mannheim Corp., Indianapolis, Ind.) and hyaluronidase. Other enzymes that can be used to disrupt placenta tissue include papain, deoxyribonucleases, serine proteases, such as trypsin, chymotrypsin, or elastase. Serine proteases may be inhibited by alpha 2 microglobulin in serum and therefore the medium used for digestion is usually serum-free. EDTA and DNase are commonly used in enzyme digestion procedures to increase the efficiency of cell recovery. The digestate is preferably diluted so as to avoid trapping stem cells within the viscous digest.

Any combination of tissue digestion enzymes can be used. Typical concentrations for tissue digestion enzymes include, e.g., 50-200 U/mL for collagenase I and collagenase IV, 1-10 U/mL for dispase, and 10-100 U/mL for elastase. Proteases can be used in combination, that is, two or more proteases in the same digestion reaction, or can be used sequentially in order to liberate placental stem cells. For example, in one embodiment, a placenta, or part thereof, is digested first with an appropriate amount of collagenase I at 2 mg/ml for 30 minutes, followed by digestion with trypsin, 0.25%, for 10 minutes, at 37° C. Serine proteases are preferably used consecutively following use of other enzymes.

In another embodiment, the tissue can further be disrupted by the addition of a chelator, e.g., ethylene glycol bis(2-aminoethyl ether)-N,N,N',N'-tetraacetic acid (EGTA) or ethylenediaminetetraacetic acid (EDTA) to the stem cell collection composition comprising the stem cells, or to a solution in which the tissue is disrupted and/or digested prior to isolation of the stem cells with the stem cell collection composition.

Where an entire placenta, or portion of a placenta comprising both fetal and maternal cells (for example, where the portion of the placenta comprises the chorion or cotyledons), the placental stem cells collected will comprise a mix of placental stem cells derived from both fetal and maternal sources. Where a portion of the placenta that comprises no, or a negligible number of, maternal cells (for example, amnion), the placental stem cells collected will comprise almost exclusively fetal placental stem cells.

6.6.1.1 Isolation and Characterization of Placental Stem Cells

Stem cells from mammalian placenta, whether obtained by perfusion or enyzmatic digestion, can initially be purified from (i.e., be isolated from) other cells by, e.g., Ficoll gradient centrifugation. Such centrifugation can follow any standard protocol for centrifugation speed, etc. In one embodiment, for example, cells collected from the placenta are recovered from perfusate by centrifugation at 5000×g for 15 minutes at room temperature, which separates cells from, e.g., contaminating debris and platelets. In another embodiment, placental perfusate is concentrated to about 200 ml, gently layered over Ficoll, and centrifuged at about 1100×g for 20 minutes at 22° C., and the low-density interface layer of cells is collected for further processing.

Cell pellets can be resuspended in fresh stem cell collection composition, or a medium suitable for stem cell maintenance, e.g., IMDM serum-free medium containing 2 U/ml heparin and 2 mM EDTA (GibcoBRL, NY). The total mononuclear cell fraction can be isolated, e.g., using Lymphoprep (Nycomed Pharma, Oslo, Norway) according to the manufacturer's recommended procedure.

As used herein, "isolating" placental stem cells means to remove at least 20%, 30%, 40%, 50%, 60%, 70%, 80%, 90%, 95% or 99% of the cells with which the stem cells are normally associated in the intact mammalian placenta. A stem cell from an organ is "isolated" when it is present in a population of cells that comprises fewer than 50% of the cells with which the stem cell is normally associated in the intact organ.

Placental cells obtained by perfusion or digestion can, for example, be further, or initially, isolated by differential trypsinization using, e.g., a solution of 0.05% trypsin with 0.2% EDTA (Sigma, St. Louis Mo.). Differential trypsinization is possible because placental stem cells typically detach from plastic surfaces within about five minutes whereas other adherent populations typically require more than 20-30 minutes incubation. The detached placental stem cells can be harvested following trypsinization and trypsin neutralization, using, e.g., Trypsin Neutralizing Solution (TNS, Cambrex). In one embodiment of isolation of adherent cells, aliquots of, for example, about 5–10×10$^6$ cells are placed in each of several T-75 flasks, preferably fibronectin-coated T75 flasks. In such an embodiment, the cells can be cultured with commercially available Mesenchymal Stem Cell Growth Medium (MSCGM) (Cambrex), and placed in a tissue culture incubator (37° C., 5% $CO_2$). After 10 to 15 days, non-adherent cells are removed from the flasks by washing with PBS. The PBS is then replaced by MSCGM. Flasks are preferably examined daily for the presence of various adherent cell types and in particular, for identification and expansion of clusters of fibroblastoid cells.

The number and type of cells collected from a mammalian placenta can be monitored, for example, by measuring changes in morphology and cell surface markers using standard cell detection techniques such as flow cytometry, cell sorting, immunocytochemistry (e.g., staining with tissue specific or cell-marker specific antibodies) fluorescence activated cell sorting (FACS), magnetic activated cell sorting (MACS), by examination of the morphology of cells using light or confocal microscopy, and/or by measuring changes in gene expression using techniques well known in the art, such as PCR and gene expression profiling. These techniques can be used, too, to identify cells that are positive for one or more particular markers. For example, using antibodies to CD34, one can determine, using the techniques above, whether a cell comprises a detectable amount of CD34; if so, the cell is CD34$^+$. Likewise, if a cell produces enough OCT-4 RNA to be detectable by RT-PCR, or significantly more OCT-4 RNA than an adult cell, the cell is OCT-4$^+$. Antibodies to cell surface markers (e.g., CD markers such as CD34) and the sequence of stem cell-specific genes, such as OCT-4, are well-known in the art.

Placental stem cells, particularly cells that have been isolated by Ficoll separation, differential adherence, or a combination of both, may be sorted using a fluorescence activated cell sorter (FACS). Fluorescence activated cell sorting (FACS) is a well-known method for separating particles, including cells, based on the fluorescent properties of the particles (Kamarch, 1987, *Methods Enzymol*, 151: 150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one sorting scheme, stem cells from placenta are sorted on the basis of expression of the markers CD34, CD38, CD44, CD45, CD73, CD105, OCT-4 and/or HLA-G. This can be accomplished in connection with procedures to select stem cells on the basis of their adherence properties in culture. For example, an adherence selection stem can be accomplished before or after sorting on the basis of marker expression. In one embodiment, for example, cells are sorted first on the basis of their expression of CD34; CD34$^-$ cells are retained, and cells that are CD200$^+$HLA-G$^+$, are separated from all other CD34$^-$ cells. In another embodiment, cells from placenta are based on their expression of markers CD200 and/or HLA-G; for example, cells displaying either of these markers are isolated for further use. Cells that express, e.g., CD200 and/or HLA-G can, in a specific embodiment, be further sorted based on their expression of CD73 and/or CD105, or epitopes recognized by antibodies SH2, SH3 or SH4, or lack of expression of CD34, CD38 or CD45. For example, in one embodiment, placental cells are sorted by expression, or lack thereof, of CD200, HLA-G, CD73, CD105, CD34, CD38 and CD45, and placental cells that are CD200$^+$, HLA-G$^+$, CD73$^+$, CD105$^+$, CD34$^-$, CD38$^-$ and CD45$^-$ are isolated from other placental cells for further use.

In another embodiment, magnetic beads can be used to separate cells. The cells may be sorted using a magnetic activated cell sorting (MACS) technique, a method for separating particles based on their ability to bind magnetic beads (0.5-100 μm diameter). A variety of useful modifications can be performed on the magnetic microspheres, including covalent addition of antibody that specifically recognizes a particular cell surface molecule or hapten. The beads are then mixed with the cells to allow binding. Cells are then passed through a magnetic field to separate out cells having the specific cell surface marker. In one embodiment, these cells can then isolated and re-mixed with magnetic beads coupled to an antibody against additional cell surface markers. The cells are again passed through a magnetic field, isolating cells that bound both the antibodies. Such cells can then be diluted into separate dishes, such as microtiter dishes for clonal isolation.

Placental stem cells can also be characterized and/or sorted based on cell morphology and growth characteristics. For example, placental stem cells can be characterized as having, and/or selected on the basis of, e.g., a fibroblastoid appearance in culture. Placental stem cells can also be characterized as having, and/or be selected, on the basis of their ability to form embryoid-like bodies. In one embodiment, for example, placental cells that are fibroblastoid in shape, express CD73 and CD105, and produce one or more embryoid-like bodies in culture are isolated from other placental cells. In another embodiment, OCT-4$^+$ placental cells that produce one or more embryoid-like bodies in culture are isolated from other placental cells.

In another embodiment, placental stem cells can be identified and characterized by a colony forming unit assay.

Colony forming unit assays are commonly known in the art, such as MESENCULT™ medium (Stem Cell Technologies, Inc., Vancouver British Columbia)

Placental stem cells can be assessed for viability, proliferation potential, and longevity using standard techniques known in the art, such as trypan blue exclusion assay, fluorescein diacetate uptake assay, propidium iodide uptake assay (to assess viability); and thymidine uptake assay, MTT cell proliferation assay (to assess proliferation). Longevity may be determined by methods well known in the art, such as by determining the maximum number of population doubling in an extended culture.

Placental stem cells can also be separated from other placental cells using other techniques known in the art, e.g., selective growth of desired cells (positive selection), selective destruction of unwanted cells (negative selection); separation based upon differential cell agglutinability in the mixed population as, for example, with soybean agglutinin; freeze-thaw procedures; filtration; conventional and zonal centrifugation; centrifugal elutriation (counter-streaming centrifugation); unit gravity separation; countercurrent distribution; electrophoresis; and the like.

6.6.1.2 Culture of Placental Stem Cells

Placental stem cells can be isolated as described above and immediately contacted with a composition of the invention. Placental stem cells can also be cultured, e.g., in cell culture, for a number of generations prior to contacting with the composition of the invention. For example, isolated placental stem cells, or placental stem cell population, or cells or placental tissue from which placental stem cells grow out, can be used to initiate, or seed, cell cultures. Cells are generally transferred to sterile tissue culture vessels either uncoated or coated with extracellular matrix or ligands such as laminin, collagen (e.g., native or denatured), gelatin, fibronectin, ornithine, vitronectin, and extracellular membrane protein (e.g., MATRIGEL® (BD Discovery Labware, Bedford, Mass.)).

In preferred embodiments, the placental stem cells are cultured on a collagen composition of the present invention. In certain embodiments, the collagen composition comprises detectable amounts of fibronectin and laminin. In other embodiments, the collagen composition comprises no detectable amount of fibronectin or laminin. In other embodiments, the collagen composition comprises at least about 5%, or at least about 10%, elastin by dry weight. In another embodiment, the collagen composition comprises no more than about 5% elastin by dry weight.

In certain embodiments, placental stem cells are cultured for the production of specific cytokines that are collectable from the culture medium. In specific embodiments, the cytokine is IL-6, IL-8, and/or monocyte chemotactic protein-1 (MCP-1). In certain other embodiments, the placental stem cells are cultured for the production of fibronectin. In a specific embodiment, the placental stem cells are cultured on a composition of the invention which comprises less than about 5% fibronectin.

As noted above, the placental collagen compositions of the invention can be shaped into any shape that is useful, e.g., medically useful. These compositions, once shaped and dried, are stable in aqueous solution, e.g., tissue culture medium or buffer. Thus, stem cells, such as placental stem cells, can be cultured directly on the shaped compositions. Such culturing can be done in cell culture dishes or other liquid containers, e.g., flasks, suitable for cell culture.

Placental stem cells can be cultured in any medium, and under any conditions, recognized in the art as acceptable for the culture of stem cells. Preferably, the culture medium comprises serum. Placental stem cells can be cultured in, for example, DMEM-LG (Dulbecco's Modified Essential Medium, low glucose)/MCDB 201 (chick fibroblast basal medium) containing ITS (insulin-transferrin-selenium), LA+BSA (linoleic acid-bovine serum albumin), dextrose, L-ascorbic acid, PDGF, EGF, IGF-1, and penicillin/streptomycin; DMEM-HG (high glucose) comprising 10% fetal bovine serum (FBS); DMEM-HG comprising 15% FBS; IMDM (Iscove's modified Dulbecco's medium) comprising 10% FBS, 10% horse serum, and hydrocortisone; M199 comprising 10% FBS, EGF, and heparin; ÿ-MEM (minimal essential medium) comprising 10% FBS, GLUTAMAX™ and gentamicin; DMEM comprising 10% FBS, GLUTAMAX™ and gentamicin, etc. A preferred medium is DMEM-LG/MCDB-201 comprising 2% FBS, ITS, LA+BSA, dextrose, L-ascorbic acid, PDGF, EGF, and penicillin/streptomycin.

Other media in that can be used to culture placental stem cells include DMEM (high or low glucose), Eagle's basal medium, Ham's F10 medium (F10), Ham's F-12 medium (F12), Iscove's modified Dulbecco's medium, Mesenchymal Stem Cell Growth Medium (MSCGM), Liebovitz's L-15 medium, MCDB, DMEM/F12, RPMI 1640, advanced DMEM (Gibco), DMEM/MCDB201 (Sigma), and CELL-GRO FREE.

The culture medium can be supplemented with one or more components including, for example, serum (e.g., fetal bovine serum (FBS), preferably about 2-15% (v/v); equine (horse) serum (ES); human serum (HS)); beta-mercaptoethanol (BME), preferably about 0.001% (v/v); one or more growth factors, for example, platelet-derived growth factor (PDGF), epidermal growth factor (EGF), basic fibroblast growth factor (bFGF), insulin-like growth factor-1 (IGF-1), leukemia inhibitory factor (LIF), vascular endothelial growth factor (VEGF), and erythropoietin (EPO); amino acids, including L-valine; and one or more antibiotic and/or antimycotic agents to control microbial contamination, such as, for example, penicillin G, streptomycin sulfate, amphotericin B, gentamicin, and nystatin, either alone or in combination.

Placental stem cells can be cultured in standard tissue culture conditions, e.g., in tissue culture dishes or multiwell plates. Placental stem cells can also be cultured using a hanging drop method. In this method, placental stem cells are suspended at about $1 \times 10^4$ cells per mL in about 5 mL of medium, and one or more drops of the medium are placed on the inside of the lid of a tissue culture container, e.g., a 100 mL Petri dish. The drops can be, e.g., single drops, or multiple drops from, e.g., a multichannel pipetter. The lid is carefully inverted and placed on top of the bottom of the dish, which contains a volume of liquid, e.g., sterile PBS sufficient to maintain the moisture content in the dish atmosphere, and the stem cells are cultured.

Once an isolated placental stem cell, or isolated population of stem cells (e.g., a stem cell or population of stem cells separated from at least 50% of the placental cells with which the stem cell or population of stem cells is normally associated in vivo), the stem cell or population of stem cells can be proliferated and expanded in vitro. For example, a population of placental stem cells can be cultured in tissue culture containers, e.g., dishes, flasks, multiwell plates, or the like, for a sufficient time for the stem cells to proliferate to 70-90% confluence, that is, until the stem cells and their progeny occupy 70-90% of the culturing surface area of the tissue culture container.

Placental stem cells can be seeded in culture vessels at a density that allows cell growth. For example, the cells may be seeded at low density (e.g., about 1,000 to about 5,000 cells/cm$^2$) to high density (e.g., about 50,000 or more cells/cm$^2$). In a preferred embodiment, the cells are cultured at about 0 to about 5 percent by volume $CO_2$ in air. In some preferred embodiments, the cells are cultured at about 2 to about 25 percent $O_2$ in air, preferably about 5 to about 20 percent $O_2$ in air. The cells preferably are cultured at about 25° C. to about 40° C., preferably 37° C. The cells are preferably cultured in an incubator. The culture medium can be static or agitated, for example, using a bioreactor. Placental stem cells preferably are grown under low oxidative stress (e.g., with addition of glutathione, ascorbic acid, catalase, tocopherol, N-acetylcysteine, or the like).

Once 70%-90% confluence is obtained, the cells may be passed. For example, the cells can be enzymatically treated, e.g., trypsinized, using techniques well-known in the art, to separate them from the tissue culture surface. After removing the cells by pipetting and counting the cells, about 20,000-100,000 stem cells, preferably about 50,000 stem cells, are passaged to a new culture container containing fresh culture medium. Typically, the new medium is the same type of medium from which the stem cells were removed. Placental stem cells that have been passaged at least 1, 2, 3, 4, 5, 6, 7, 8, 9, 10, 12, 14, 16, 18, or 20 times, or more, can be used in combination with the collagen compositions of the invention.

6.6.2. Non-Stem Cells

The composition of the invention, comprising stem cells, can, in certain embodiments, also comprise one or more types of non-stem cells. As used herein, "non-stem cell" indicates a terminally-differentiated cell. For example, in one embodiment, the composition of the invention comprises a plurality of stem cells and a plurality of fibroblasts. Non-stem cells that can be included with the compositions of the invention include, without limitation, fibroblasts or fibroblast-like cells; endothelial cells, epithelial cells, muscle cells, cardiac cells, pancreatic cells; and the like. In certain other embodiments, the composition comprises at least two types of stem cells and at least two types of non-stem cells.

6.7 Methods of Using the Collagen Compositions

In a further aspect, the present invention provides methods of using the collagen compositions of the invention therapeutically, prophylactically or cosmetically.

The collagen compositions of the present invention have a broad array of potential uses. Uses include, but are not limited to, manufacture of engineered tissue and organs, including structures such as patches or plugs of tissues or matrix material, prosthetics, and other implants, tissue scaffolding, repair or dressing of wounds, hemostatic devices, devices for use in tissue repair and support such as sutures, surgical and orthopedic screws, and surgical and orthopedic plates, natural coatings or components for synthetic implants, cosmetic implants and supports, repair or structural support for organs or tissues, substance delivery, bioengineering platforms, platforms for testing the effect of substances upon cells, cell culture, and numerous other uses. This discussion of possible uses is not intended to be exhaustive and many other embodiments exist. Furthermore, although many specific examples are provided below regarding combination of collagen with other materials and/or specific substances, many other combinations of materials and substances may be used.

In applications in which the collagen composition is to be used for the treatment or filling of a wound, it may be advantageous for the composition to stimulate the production of fibronectin by stem cells in surrounding tissues. In such an embodiment, the wound can be contacted with a composition of the invention that comprises no detectable amount of fibronectin.

The ability to combine cells in a collagen material provides the ability to use the compositions of the present invention to build tissue, organs, or organ-like tissue. Cells included in such tissues or organs can include cells that serve a function of delivering a substance, seeded cells that will provide the beginnings of replacement tissue, or both. Many types of cells can be used to create tissue or organs. Stem cells, committed stem cells, and/or differentiated cells are used in various embodiments. Examples of stem cells used in these embodiments include, but are not limited to, embryonic stem cells, bone marrow stem cells and umbilical cord stem cells used to make organs or organ-like tissue such as livers or kidneys. In some embodiments the shape of the composition helps send signals to the cells to grow and reproduce in a specific type of desired way. Other substances, for example differentiation inducers, can be added to the matrix to promote specific types of cell growth. Further, different mixtures of cell types are incorporated into the composition in some embodiments. The ability to use collagen materials and matrices to bioengineer tissue or organs creates a wide variety of bioengineered tissue replacement applications. Examples of bioengineered components include, but are not limited to, bone, dental structures, joints, cartilage, skeletal muscle, smooth muscle, cardiac muscle, tendons, menisci, ligaments, blood vessels, stents, heart valves, corneas, ear drums, nerve guides, tissue or organ patches or sealants, a filler for missing tissues, sheets for cosmetic repairs, skin (sheets with cells added to make a skin equivalent), soft tissue structures of the throat such as trachea, epiglottis, and vocal cords, other cartilaginous structures such as nasal cartilage, tarsal plates, tracheal rings, thyroid cartilage, and arytenoid cartilage, connective tissue, vascular grafts and components thereof, and sheets for topical applications, and repair to or replacement of organs such as livers, kidneys, and pancreas. In some embodiments, such matrices are combined with drug and substance delivery matrices of the present invention in ways that will improve the function of the implant. For example, antibiotics, anti-inflammatory agents, local anesthetics or combinations thereof, can be added to the matrix of a bioengineered organ to speed the healing process and reduce discomfort.

6.7.1. Cosmetic Applications

Human skin is a composite material of the epidermis and the dermis. The outermost layer of the epidermal layer of the skin is the stratum corneum. Beneath the stratum corneum layer is the epidermis. Below the epidermis, is the outermost layer of the dermis called the papillary dermis, followed by the reticular dermis and the subcutaneous layer.

The skin serves many functions including protection, absorption, pigmentogenesis, sensory perception, secretion, excretion, thermoregulation, and regulation of immunological processes. These skin functions are negatively affected, for example, by aging, excessive sun exposure, smoking, trauma, and/or environmental factors, which cause structural changes in the skin and can result in impairment of the barrier function of the skin and a decreased turnover of epidermal cells. Damaged collagen and elastin lose the ability to contract properly, which results in skin wrinkling and surface roughness. Wrinkles are modifications of the skin that are typically associated with cutaneous aging and develop preferentially on sun-exposed skin. As aging progresses, the face, as well as other areas of the body begin to show the effects of gravity, sun exposure and years of, e.g., facial muscle movement, such as smiling, chewing and squinting. As the skin ages or becomes unhealthy, it acquires wrinkles, sags, and stretch marks, it roughens, and it has a decrease ability to synthesize Vitamin D. Aged skin also becomes thinner and has a flattened dermoepidermal interface because of the alterations in collagen, elastin, and glycosaminoglycans. Typically, aging skin can be characterized by decreased thickness, elasticity, and adherence to underlying tissue.

Damage to the skin due to aging, environmental factors, exposure to the sun and other elements, such as weight loss, child bearing, disease (e.g., acne and cancer) and surgery often results in skin contour deficiencies and other skin anomalies. In order to correct contour deficiencies and other anomalies of the skin, people often resort to cosmetic surgery, such as face lifts and skin tucks. Cosmetic surgery, however, is generally expensive, invasive, and has the potential of leaving scars in the areas of operation and may affect normal biological and physiological functions. Thus, there remains a need for alternative therapies.

The invention provides methods for skin augmentation in a patient. In one embodiment, a method for skin augmentation in a patient comprises injecting or otherwise administering a collagen composition of the invention to an area of the face or body of a patient in need of augmenting, wherein the area of the face or body of the patient is augmented as compared to the area prior to administration of the collagen. "Skin augmentation" in the context of the present invention refers to any change of the natural state of a patient's (e.g., a human's) skin and related areas due to external acts or effects. Non-limiting areas of the skin that may be changed by skin augmentation include the epidermis, dermis, subcutaneous layer, fat, arrector pill muscle, hair shaft, sweat pore, sebaceous gland, or a combination thereof.

In some embodiments, methods of the invention comprise injecting or otherwise administrating a collagen composition of the invention to a patient for the treatment of crow's feet, nasolabial folds ("smile lines"), marionette lines, glabellar folds ("frown lines"), or a combination thereof. A collagen composition of the invention can help fill in lines, creases, and other wrinkles and restore a smoother, more youthful-looking appearance. A collagen composition of the invention can be used alone or in conjunction with one or more additional injectable compositions, a resurfacing procedure, such as a laser treatment, or a recontouring procedure, such as a facelift.

In one embodiment, a collagen composition of the invention may also be used to augment creased or sunken areas of the face and/or to add or increase the fullness to areas of the face and body of a patient. The areas of the face an/or body requiring augmentation may be the result of, e.g., aging, trauma, disease, sickness, environmental factors, weight loss, child birth or a combination thereof. Non-limiting examples of an area of the face or body of a patient where a collagen composition of the invention may be injected or otherwise administered include the undereye, temple, upper malar, sub malar, chin, lip, jawline, forehead, glabella, outer brow, cheek, area between upper lip and nose, nose (such as the bridge of the nose), neck, buttocks, hips, sternum, or any other part of the face or body, or a combination thereof.

A collagen composition of the invention may be used to treat skin deficiencies including, but not limited to, wrinkles, depressions or other creases (e.g., frown lines, worry lines, crow's feet, marionette lines), stretch marks, internal and external scars (such as scars resulting from injury, wounds, accidents, bites, or surgery), or combinations thereof. In some embodiments, a collagen composition of the invention may be used for the correction of, for example, "hollow" eyes, visible vessels resulting in dark circles, as well as visible tear troughs. A collagen composition of the invention may also be used, for example, for correction of the undereye after aggressive removal of undereye fat pads from lower blepharoplasty or correction of the lower cheek after aggressive buccal fat extraction or natural loss. In one embodiment, a collagen composition of the invention may be used to correct the results of rhinoplasty, skin graft or other surgically-induced irregularities, such as indentations resulting from liposuction. In other embodiments, a collagen composition of the invention may be used for the correction of facial or body scars (e.g., wound, chicken pox, or acne scars). In some embodiments, a collagen composition of the invention is injected or otherwise administered into a patient for facial reshaping. Facial reshaping using the methods of the invention may be completed in a patient with neck laxity, or having a gaunt face, long face, bottom-heavy face, asymmetrical face, a chubby face, or having a face with localized fat atrophy, a midface retrusion, sunken eyes, and/or any combinations thereof.

In one embodiment, the methods of the invention comprise injecting or otherwise administering a collagen composition of the invention to a patient for the treatment a skin deficiency, such as skin deficiency caused by a disease or illness, such as cancer or acne. The deficiency can be the direct or indirect result of the disease or illness. For example, a skin deficiency can by caused by a disease or illness or can be caused by a treatment of a disease or illness.

6.7.2. Non-Cosmetic Applications 6.7.2.1 Void Filling

The invention provides methods for sealing, filling and/or otherwise treating a void within the body of a patient. In some embodiments, the methods of the invention comprise injecting or otherwise administering a collagen composition of the invention to a patient to fill a void within the body of the patient. For example, a collagen composition can be administered to the patient in the area where the void is located. The term "void" is intended to encompass any undesirable hollow space created by aging, disease, surgery, congenital abnormalities, or a combination thereof. For example, a void may be created following the surgical removal of a tumor or other mass from the body of a patient. Non-limiting examples of voids which may be filled with a collagen composition of the invention include a fissure, fistula, divercula, aneurysm, cyst, lesion, or any other undesirable hollow space in any organ or tissue of the patient's body.

In some embodiments, a collagen composition of the invention may be used to fill, seal and/or otherwise treat, in whole or in part, a crevice, fissure, or fistula within a tissue, organ, or other structure of the body (e.g., a blood vessel), or junctures between adjacent tissues, organs or structures, to prevent the leakage of biological fluids, such as blood, urine, or other biological fluids. For example, a collagen composition of the invention can be injected, implanted, threaded into, or otherwise administered into fistula between viscera, or into the opening or orifice from a viscus to the exterior of the patient's body. A collagen composition of the invention can be used to fill a void or other defect formed by these pathological states and stimulate fibroblast infiltration, healing, and ingrowth of tissue.

In one embodiment, a method of the invention is used to fill, seal, and/or otherwise treat a fistula in a patient in need of treatment, said method comprising injecting or otherwise administering to the patient a collagen composition of the invention. A collagen composition of the invention can be administered to the patient by injection through a needle into one of the fistular orifices and filling most or all of the branches of the orifice. Alternatively, strings or rods of the collagens can be threaded into the fistulae lesions through an orifice, or the collagen can be introduced into the patient with a catheter. Various types of fistulae can be filled, sealed and/or otherwise treated by a collagen composition or method of the invention, such as anal, arteriovenous, bladder, carotid-cavernous, external, gastric, intestinal, parietal, salivary, vaginal, and anorectal fistulae, or a combination thereof.

In one embodiment, a method of the invention is used to fill, seal and/or otherwise treat a diverticulum in a patient in need of treatment, said method comprising injecting or otherwise administering to the patient a collagen composition of the invention. Diverticulae are abnormal physiological structures that are pouches or sac openings from a tubular or saccular organ, such as the intestine, the bladder, and the like, and can be filled or augmented using a collagen composition of the invention.

In another embodiment, a method of the invention is used to fill, seal and/or otherwise treat a cyst in a patient in need of treatment, said method comprising injecting or otherwise administering to the patient a collagen composition of the invention. Cysts are abnormal sacs having a membrane lining that contain gas, fluid, or semi-solid material along. In some embodiments, the cyst is a pseudocyst, which has an accumulation of, e.g., fluid but does not comprise an epithelial or other membranous lining. Additional non-limiting examples of cysts that can be filled, sealed and/or otherwise treated by the invention include sebaceous, dermoid, bone, or serous cysts, or a combination thereof.

In another embodiment, a method of the invention comprises injecting or otherwise administering a collagen composition of the invention to fill in whole, or in part, any voids created as a result of surgical, chemical or biological removal of unnecessary or undesirable growths, fluids, cells, or tissues from a patient. A collagen composition can be locally injected or otherwise administered at the site of the void so as to augment the remaining and surrounding tissue, aid in the healing process, and minimize the risk of infection. This augmentation is especially useful for void sites created after tumor excision, such as after breast cancer surgery, surgery for removal of tumorous connective tissue, bone tissues or cartilage tissue, and the like.

The present invention further provides method of causing augmentation by injecting or otherwise administering a collagen composition of the invention not directly into the body, but extracorporeally into organs, components of organs, or tissues prior to the inclusion of said tissues, organs or components of organs into the body.

6.7.2.2 Tissue Bulking

In one embodiment, the methods of the invention comprise administering a collagen composition of the invention to a patient for tissue bulking. "Tissue bulking" in the context of the present invention refers to any change of the natural state of a patient's (e.g., a human's) non-dermal soft tissues due to external acts or effects. The tissues encompassed by the invention include, but not limited to, muscle tissues, connective tissues, fats, and, nerve tissues. The tissues encompassed by the present invention may be part of many organs or body parts including, but not limited to, the sphincter, the bladder sphincter and urethra.

6.7.2.3 Urinary Incontinence

Urinary incontinence (including stress urinary incontinence) is the sudden leakage of urine that occurs with activities that result in an increase in intra-abdominal pressure, such as coughing, sneezing, laughing or exercise. During these activities, intra-abdominal pressure rises transiently above urethral resistance, thus resulting in a sudden, usually small, amount of urinary leakage. Stress incontinence is generally a bladder storage problem in which the strength of the urethral sphincter is diminished, and the sphincter is not able to prevent urine flow when there is increased pressure from the abdomen. Urinary incontinence may occur as a result of weakened pelvic muscles that support the bladder and urethra, or because of malfunction of the urethral sphincter. For example, prior trauma to the urethral area, neurological injury, and some medications may weaken the urethra. Urinary incontinence is most commonly seen in women after menopause, pelvic surgery, or childbearing, e.g., after multiple pregnancies and vaginal childbirths, or who have pelvic prolapse (protrusion of the bladder, urethra, or rectal wall into the vaginal space), with cystocele, cystourethrocele, or rectocele), and is usually related to a loss of anterior vaginal support. In men, urinary incontinence may be observed after prostatic surgery, most commonly radical prostatectomy, in which there may be injury to the external urethral sphincter.

The invention encompasses a method for managing or treating urinary incontinence, or a symptom or condition resulting therefrom, comprising injecting or otherwise administering a collagen composition of the invention to a patient in need thereof, wherein the patient's sphincter tissue is augmented and continence is improved or restored in the patient. The collagen composition can be injected or otherwise administered periurethrally to increase tissue bulk around the urethra for the management and/or treatment of urinary incontinence. Improvement in stress incontinence can achieved by increasing the tissue bulk and thereby increasing resistance to the outflow of urine.

In some embodiments, a collagen composition of the invention is injected or otherwise administered to a patient in the area around the urethra, for example, to close a hole in the urethra through which urine leaks out or to build up the thickness of the wall of the urethra so it seals tightly when urine is being held back, In another embodiment, a collagen composition of the invention is injected or otherwise administered to a patient around the urethra just outside the muscle of the urethra at the bladder outlet. Injecting the bulking material can be done through the skin, through the urethra, or, in women, through the vagina.

When needles are used for injection of the collagen compositions of the invention, needle placement can be guided by the use of a cystoscope inserted into the urethra. Urethral bulking procedures can be performed under local anesthesia, but some patients may require a general, regional or spinal anesthesia. A local anesthetic can be used so the patient can stand up after an injection, and it can be determined whether continence has been achieved. If continence has not been restored, one or more subsequent injection(s) can be administered to the patient. The procedure may need to be repeated after a few months to achieve bladder control. The collagen injection helps control the urine leakage by bulking up the area around the urethra, thus compressing the sphincter.

6.7.2.4 Vesicoureteral Reflux

Vesicoureteral reflux (VUR) (or urinary reflux) is characterized by the retrograde flow of urine from the bladder to the kidneys. Untreated VUR may cause devastating long-term effects on renal function and overall patient health. A patient with VUR has an increased risk of developing a urinary tract infection, renal scarring, pyelonephritis, hypertension, and progressive renal failure.

The invention provides a method for the management or treatment of VUR, or a symptom or condition resulting therefrom, comprising injecting or otherwise administering to a patient in need thereof a collagen composition of the invention, wherein the ureteral wall of the patient is augmented, and the symptoms of VUR are reduced or eliminated. The collagen composition can be injected (e.g., a subtrigonal injection) or otherwise administered, such as under endoscopic guidance, into the detrusor backing under the ureteral orifice using any method known to those in the art.

6.7.2.5 Gastroesophageal Reflux Disease

Gastroesophageal reflux disease (GERD) is a disorder that usually occurs because the lower esophageal sphincter (LES)— the muscular valve where the esophagus joins the stomach-does not close properly, relaxes or weakens, and stomach contents leak back, or reflux, into the esophagus. When the stomach acid, or occasionally bile salts, comes into contact with the esophagus it causes the burning sensation of heartburn that most of us occasionally feel. When refluxed stomach acid touches the lining of the esophagus, it causes a burning sensation in the chest or throat (heartburn), and the fluid may be tasted in the back of the mouth (acid indigestion). Over time, the reflux of stomach acid damages the tissue lining the esophagus, causing inflammation and pain. In adults, long-lasting, untreated GERD can lead to permanent damage of the esophagus and sometimes even cancer. Anyone, including infants, children, and pregnant women, can have GERD.

The invention provides a method for the management or treatment of GERD, or a symptom or condition resulting therefrom, comprising injecting or otherwise administering to a patient in need thereof a collagen composition of the invention, wherein the LES of the patient is augmented, and the symptoms of GERD are reduced or eliminated. In some embodiments, the collagen composition is administered under endoscopic guidance into the esophageal wall at the level of the esophagogastric junction. Intended to impede reflux, the bulking effect results from a combination of the retained material and consequent tissue response. A collagen composition of the invention can be injected through standard or large-bore (e.g., large gauge) injection needles.

6.7.2.6 Vocal Cords and Larynx

The invention provides methods for the management or treatment of a disease, disorder (such as a neurological disorder), or other abnormality that affects the one or both vocal cords (folds) and/or the larynx (voice box). Non-limiting examples of such diseases, disorders or other abnormalities of the larynx an vocal cords are glottic incompetence, unilateral vocal cord paralysis, bilateral vocal cord paralysis, paralytic dysphonia, nonparalytic dysphonia, spasmodic dysphonia or a combination thereof. In other embodiments, the methods of the invention may also be used to manage or treat diseases, disorders or other abnormalities that result in the vocal cords closing improperly, such as an incomplete paralysis of the vocal cord ("paresis"), generally weakened vocal cords, for instance, with old age ("presbylaryngis"), and/or scarring of the vocal cords (e.g., from previous surgery or radiotherapy).

The invention encompasses methods that provide support or bulk to a vocal fold in a patient that lacks the bulk (such as in vocal fold bowing or atrophy) or the mobility (such as in paralysis) the vocal cord once had. In some embodiments, the vocal cords and/or other soft tissues of the larynx can be augmented with a collagen composition of the invention, either alone or in combination with other treatments or medications. In one embodiment, a collagen composition of the invention augments or adds bulk to one (or both) vocal folds so that it can make contact with the other vocal fold.

Any one of a number of procedures well known to those in the art may be used for administration of a collagen composition of the invention to a vocal cord(s) or larynx of a patient. In some embodiments, a curved needle is used to inject a collagen composition of the invention through the mouth of the patient. In other embodiments, a needle (such as a higher gauge, short needle) may be used to inject a collagen composition of the invention directly through the skin and the Adam's apple of the patient. A collagen composition of the invention can be administered to a patient while monitoring the vocal folds of the patient with a laryngoscope on a video monitor.

6.7.2.7 Glottic Incompetence

In one embodiment, the invention provides a method for the management or treatment of glottic incompetence. Percutaneous laryngeal collagen augmentation can occur by injection the collagen of the invention using a needle into the vocal cords of a patient using methods known in the art. In some cases, the patient has hypophonia and/or glottic incompetence that affects the voice function of the larynx, increased muscle rigidity, and decreased ability for movement of the thyroarytenoid muscle. In another embodiment, the hypophonia is a result of Parkinson's Disease. In one embodiment, a method of the invention for the management or treatment of glottic incompetence in a patient in need thereof comprises injecting or otherwise administering a collagen composition of the invention to the vocal cords of a patient, wherein the injection augments the vocal cord and improves glottic closure, such that glottic incompetence is reduced or eliminated in the patient. The patient may or may not have mobile vocal cords prior to administration of a collagen composition of the invention.

6.7.2.8 Dysphonia

Dysphonia is any impairment of the voice or difficulty speaking. Dysphonia may or may not be associated with laryngeal or vocal cord paralysis. The invention provides methods for the management or treatment of dysphonia, such as paralytic dysphonia, non-paralytic dysphonia or spasmodic dysphonia. In one embodiment, a method for managing or treating dystonia in a patient comprises injecting or administering a collagen composition of the invention to the patient in need thereof, wherein dystonia is improved in patient as compared to prior to administration of the collagen composition. In some cases, laryngeal collagen injection permits further medialization of one or both vocal folds by small increments to improve phonation in conjunction with or after medialization thyroplasty.

6.7.2.9 Vocal Cord Paralysis

The vocal cord is essentially a muscle covered with a mucous membrane. When the muscle is no longer connected to a nerve, the muscle atrophies. Therefore, typical paralyzed vocal cords are be small in size and bowed. Additionally, depending on the type of paralysis, the vocal cord may or may not be moving close enough to the middle for the other vocal cord to come touch it. When vocal cords are incapable of meeting, it is difficult for the patient to make a sound (or at least a loud sound). Thus, the invention provides methods to augment or bulk an atrophied vocal cord in a patient with vocal cord paralysis, wherein the ability of the vocal cords to come together is improved.

Unilateral vocal fold paralysis is immobility of one vocal fold, typically because of nerve dysfunction, and often the larynx is unable to completely close. The recurrent laryngeal nerve is the main nerve that accounts for most of the movement of each vocal fold, and can be damaged, e.g., by various diseases, certain surgeries or viral infection. In some embodiments, vocal cord paralysis in a patient is a symptom or result of thyroid cancer, lung cancer, tuberculosis or sarcoid (or anything that causes lymph nodes to enlarge in the chest), stroke, a neurologic diseases (e.g., Charcot-Marie-Tooth, Shy-Drager, and multisystem atrophy).

Bilateral vocal cord paralysis is the immobility (usually close to the midline) of both vocal folds. In some embodiments, bilateral vocal fold paralysis in a patient is a symptom or result of, e.g., stroke or other neurologic condition (such as Arnold-Chiari malformation), thyroid cancer, surgery (such as major brain surgery) or thyroidectomy.

The invention provides methods for use in the management or treatment of vocal cord paralysis. In one embodiment, a method is provided to manage or treat unilateral or bilateral vocal cord paralysis, or a symptom related thereto in a patient, comprising injecting or otherwise administering a collagen composition of the invention to the patient, wherein vocal fold closure is improved in the patient. In one embodiment, a collagen composition of the invention augments or adds bulk to one (or both) paralyzed vocal fold so that it can make contact with the other vocal fold. The injection of a collagen composition of the invention to the patient in need thereof can be through the patient's mouth or directly through the skin and Adam's apple.

6.7.2.10 Drug Delivery

The collagen composition of the invention can be used as a drug delivery vehicle for controlled delivery of a drug, e.g., a therapeutic agent. In some embodiments the collagen composition delivers the one or more therapeutic agents to a subject, e.g. a human. The therapeutic agents encompassed within the scope of the invention are proteins, peptides, polysaccharides, polysaccharide conjugates, genetic based vaccines, live attenuated vaccines, whole cells. A non-limiting example of drugs for use in the methods of the invention is antibiotics, anti-cancer agents, anti-bacterial agents, anti-viral agents; vaccines; anesthetics; analgesics; anti-asthmatic agents; anti-inflammatory agents; anti-depressants; anti-arthritic agents; anti-diabetic agents; anti-psychotics; central nervous system stimulants; hormones; immuno-suppressants; muscle relaxants; prostaglandins.

The collagen composition may be used as a delivery vehicle for controlled delivery of one or more small molecules to a subject, e.g. a human. In some embodiments the collagen composition delivers the one or more small molecules to a subject, e.g. a human. As used herein, the term "small molecule," and analogous terms, include, but are not limited to, peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, organic or inorganic compounds having a molecular weight less than about 100 grams per mole, and salts, esters, and other pharmaceutically acceptable forms of such compounds. Salts, esters, and other pharmaceutically acceptable forms of such compounds are also encompassed.

In certain embodiments, the collagen composition of the invention as a vehicle for drug delivery results in enhanced absorption of the drug; improved pharmacokinetic profile, and systemic distribution of the drug relative to the other drug delivery systems known in the art. By improved pharmacokinetics it is meant that an enhancement of pharmacokinetic profile is achieved as measured, for example, by standard pharmacokinetic parameters such as time to achieve maximal plasma concentration (Tmax); magnitude of maximal plasma concentration (Cmax); time to elicit a detectable blood or plasma concentration (Tlag). By enhanced absorption it is meant that absorption of the drug is improved as measured by such parameters. The measurement of pharmacokinetic parameters are routinely performed in the art.

In some embodiments, the collagen compositions of the invention further comprises one or more biomolecules, e.g., therapeutic agents, including but not limited to, antibiotics, hormones, growth factors, anti-tumor agents, anti-fungal agents, anti-viral agents, pain medications, anti-histamines, anti-inflammatory agents, anti-infectives, wound healing agents, wound sealants, cellular attractants and scaffolding reagents, enzymes, receptor antagonists or agonists, hormones, growth factors, autogenous bone marrow or other cell types, antibiotics, antimicrobial agents, and antibodies, and the like, or combinations thereof. In a specific example, the collagen compositions of the invention may be impregnated with one or more growth factors, for example, fibroblast growth factor, epithelial growth factor, etc. The collagen compositions of the invention may also be impregnated with one or more small molecules, including but not limited to small organic molecules such as specific inhibitors of particular biochemical processes e.g., membrane receptor inhibitors, hormones, kinase inhibitors, growth inhibitors, anti-cancer drugs, antibiotics, etc.

In some embodiments, the collagen compositions of the invention is impregnated with a biomolecule, during production or prior to injection depending on its intended use. In some embodiments, the collagen compositions of the invention comprise a one or more interferons (α-IFN, β-IFN, γ-IFN), colony stimulating factors (CSF), granulocyte colony stimulating factors (GCSF), granulocyte-macrophage colony stimulating factors (GM-CSF), tumor necrosis factors (TNF), nerve growth factors (NGF), platelet derived growth factors (PDGF), lymphotoxins, epidermal growth factors (EGF), fibroblast growth factors (FGF), vascular endothelial cell growth factors, erythropoietin, transforming growth factors (TGF), oncostatin M, interleukins (IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, etc.), members of the families thereof, or combinations thereof. In some embodiments, the collagen composition of the invention comprises biologically active analogs, fragments, or derivatives of such growth factor or other biomolecule.

Particular active agents for use in methods of the present invention include growth factors, such as transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are useful. Members of the TGF supergene family include the beta transforming growth factors (for example, TGF-β1, TGF-β2, TGF-β3); bone morphogenetic proteins (for example, BMP-1, BMP-2, BMP-3, BMP-4, BMP-5, BMP-6, BMP-7, BMP-8, BMP-9); heparin-binding growth factors (for example, fibroblast growth factor (FGF), epidermal growth factor (EGF), platelet-derived growth factor (PDGF), insulin-like growth factor (IGF)); inhibins (for example, inhibin A, inhibin B); growth differentiating factors (for example, GDF-1); and activins (for example, activin A, activin B, activin AB).

6.7.2.11 Wounds And Burns

The collagen composition of the invention is expected to have an enhanced clinical utility as a wound dressing, for augmenting or replacing hard and/or soft tissue repair, as compared to other biomaterials known in the art, e.g., those described in U.S. Pat. Nos. 3,157,524; 4,320,201; 3,800,792; 4,837,285; 5,116,620, due in part to its physical properties. The collagen composition of the invention because it retains collagen's native quaternary structure provides improved tissue in-growth through cell migration into the interstices of the collagen matrix. The collagen composition of the invention allows cells to attach and grow into the collagen matrix, and to synthesize their own macromolecules. The cells thereby produce a new matrix which allows for the growth of new tissue. Such cell development is not observed on other known forms of collagen such as fibers, fleeces and soluble collagen.

In some embodiments, the invention encompasses treating a wound by placing the collagen composition of the invention directly over the skin of the subject, i.e., on the stratum corneum, on the site of the wound, so that the wound is covered, for example, using an adhesive tape. In other embodiments, the invention encompasses treating a wound using the collagen composition of the invention as an implant, e.g., as a subcutaneous implant.

The invention encompasses enhancing the rate of wound healing by the addition of a macromolecule capable of promoting tissue ingrowth to the collagen composition of the invention. Such macromolecules include but are not limited to hyaluronic acid, fibronectin, laminin, and proteoglycans (See, e.g., Doillon et al. (1987) Biomaterials 8:195 200; and Doillon and Silver (1986) Biomaterials 7:3 8).

In some embodiments, the collagen composition of the invention is used for the management of wounds including but not limited to partial and full-thickness wounds, pressure ulcers, pressure ulcers, venous ulcers, diabetic ulcers, chronic vascular ulcers, tunneled/undermined wounds, surgical wounds (e.g., donor sites/grafts, post-Moh-s surgery, post-laser surgery, podiatric, wound dehiscence), trauma wounds (e.g., abrasions, lacerations, second degree burns, and skin tears) and draining wounds. In certain embodiments, the collagen composition of the invention is intended for one-time use.

The invention further encompasses incorporating pharmacologically active agents including but not limited to platelet-derived growth factor, insulin-like growth factor, epidermal growth factor, transforming growth factor beta, angiogenesis factor, antibiotics, antifungal agents, spermicidal agents, hormones, enzymes, enzyme inhibitors in the collagen composition of the invention as described herein in section 4.4.2.7 for delivery to the skin, and any biomolecule described above. In certain embodiments, the pharmacologically active agents are provided in a physiologically effective amount.

In some embodiments, the collagen composition is further populated by living cells, including but not limited to allogenic stem cells, stem cells, and autologous adult cells, prior to being applied to the site of the wound.

The collagen composition of the invention is particularly useful for the treatment of wound infections, e.g., wound infections followed by a breakdown of surgical or traumatic wounds. In a particular embodiment, the collagen composition is impregnated with a therapeutically effective amount of an agent useful in the treatment of a wound infection, including but not limited to, an antibiotic, anti-microbial agent, and an anti-bacterial agent. The collagen composition of the invention has clinical and therapeutic utility in the treatment of wound infections from any microorganism known in the art, e.g., microorganisms that infect wounds originating from within the human body, which is a known reservoir for pathogenic organisms, or from environmental origin. A non-limiting example of the microorganisms, the growth of which in wounds may be reduced or prevented by the methods and compositions of the invention are *S. aureus, St. epidermis*, beta haemolytic *Streptococci, E. coli, Klebsiella* and *Pseudomonas* species, and among the anaerobic bacteria, the *Clostridium welchii* or *tartium*, which are the cause of gas gangrene, mainly in deep traumatic wounds.

In other embodiments, the collagen composition of the invention is used for wound treatment, including but not limited to epidermal wounds, skin wounds, chronic wounds, acute wounds, external wounds, internal wounds (e.g., the collagen composition may be wrapped around an anastosmosis site during surgery to prevent leakage of blood from suture lines, and to prevent the body from forming adhesions to the suture material), congenital wounds (e.g., dystrophic epidermolysis bullosa). In particular, the collagen composition has enhanced utility in the treatment of pressure ulcers (e.g., decubitus ulcers). Pressure ulcers occur frequently with patients subject to prolonged bedrest, e.g., quadriplegics and paraplegics who suffer skin loss due to the effects of localized pressure. The resulting pressure sores exhibit dermal erosion and loss of the epidermis and skin appendages. In yet other more specific embodiments, the collagen composition of the invention is used for the management of wounds including but not limited to partial and full-thickness wounds, pressure ulcers, venous ulcers, diabetic ulcers, chronic vascular ulcers, tunneled/undermined wounds, surgical wounds (e.g., donor sites/grafts, post-Moh's surgery, post-laser surgery, podiatric, wound dehiscence), trauma wound (e.g., abrasions, lacerations, second-degree burns, and skin tears) and draining wounds.

The collagen composition of the invention may also be used in the treatment of burns, including but not limited to first-degree burns, second-degree burns (partial thickness burns), third degree burns (full thickness burns), infection of burn wounds, infection of excised and unexcised burn wounds, infection of grafted wound, infection of donor site, loss of epithelium from a previously grafted or healed burn wound or skin graft donor site, and burn wound impetigo.

6.7.2.12 Dental

The collagen composition of the invention has particular utility in dentistry, e.g., periodontal surgery, guided tissue regeneration for regeneration of periodontal tissue, guided bone regeneration, and root coverage. The invention encompasses the use of the collagen composition of the invention to promote regeneration of periodontal intrabony defects, including but not limited to matched bilateral periodontol defects, interdental intrabony defects, deep 3-wall intrabony defects, 2-wall intrabony defects, and intrabony defects 2 and 3. The collagen composition of the invention is expected to have an enhanced therapeutic utility and enhanced clinical parameters for the treatment of periodontal intrabony defects relative to other techniques known in the art, e.g., use of cross-linked collagen membranes such as those disclosed in Quteish et al., 1992, J. Clin. Periodontol. 19(7): 476-84; Chung et al., 1990, J. Periodontol. 61(12): 732-6; Mattson et al., 1995, J. Periodontol. 66(7): 635-45; Benque et al., 1997, J. Clin. Periodontol. 24(8): 544-9; Mattson et al., 1999, J. Periodontol. 70(5): 510-7). Examples of clinical parameters that are improved using the collagen composition of the invention include but are not limited to plaque and gingival index scorings, probing pocket depth, probing attachment depth, and classification of furcation involvement and bony defect, which are known to one skilled in the art.

The invention also encompasses use of the collagen composition of the invention in treating class II furcation defects including but not limited to bilateral defects, paired buccal Class II mandibular molar furcation defects, and bilateral mandibular furcation defect. The utility of the collagen composition of the invention in treating class II furcation defects can be explained in part by its ability to regenerate lost periodontium in furcation defects. The collagen composition of the invention is expected to have an enhanced therapeutic and clinical utility relative to the collagen membranes used in the art for the treatment of class II furcation defects, such as those disclosed in Paul et al., 1992, Int. J. Periodontics Restorative Dent. 12: 123-31; Wang et al., 1994, J. Periodontol. 65: 1029-36; Blumenthal, 1993, J. Periodontol. 64: 925-33; Black et al., 1994, J. Periodontol. 54: 598-604; Yukna et al., 1995, J. Periodontol. 67: 650-7).

The invention further encompasses use of the collagen composition of the invention in root coverage procedures. The utility of the collagen composition of the invention in root coverage can be explained in part due to its ability to replace lost, damaged or disease gingival tissue based on the principles of guided tissue regeneration. The collagen composition of the invention is expected to have an enhanced clinical utility in root coverage as compared to collagen membranes in the art traditionally used for root coverage such as those disclosed in Shieh et al., 1997 J. Periodontol., 68: 770-8; Zahedi et al., 1998 J. Periodontol. 69: 975-81; Ozcan et al., 1997 J. Marmara Univ. Dent. Fa. 2: 588-98; Wang et al., 1997 J. Dent. Res. 78 (Spec Issue): 119 (Abstr. 106), for reasons cited supra.

The invention further encompasses use of the collagen composition in a subject with a periodontal disease including but not limited to, periodontitis and gingivitis. The collagen composition of the invention also has clinical utility as an adjunct to scaling and root planning procedures. The invention encompasses treating a subject with a periodontal disease using a collagen composition of the invention. An exemplary method for treating a periodontal disease in a subject with using a collagen composition of the invention comprises inserting a collagen composition, which can be impregnated with an antibiotic such as chlorhexidine gluconate, into one or more periodontal pockets in the subject, e.g., greater than or equal to 5 mm. Advantageously, the collagen composition can be biodegradable.

The collagen composition of the invention for use in dentistry may be impregnated with one or more biomolecules depending on the type of dental disorder being treated. Any biomolecule known in the art for the treatment of dental disorders is encompassed in the methods and compositions of the invention. In a specific embodiment, the collagen composition used in the treatment of a dental disorder associated with an infection may be impregnated with one or more antibiotics, including but not limited to doxocyclin, tetracycline, chlorhexidine gluconate, and minocycline.

6.7.2.13 Other Uses

The collagen composition of the present invention may also be used as a post-operative adhesion barrier in the ovaries or uterine horns. The collagen composition may also be used as an adhesion barrier in the brain (e.g., in the prevention of meningio-cerebral adhesion). Here, the collagen composition may be used for restoring the subdural space that separates the pachymeninx and leptomeninx. Generally, the collagen composition may be used as a wrapping on injured internal organs, for example, the spleen, or as a sheet adhered to the lung to control post-operative leakage. The collagen composition may also be used to support surgical treatment of tympanic membrane grafts (in tympanic perforations), or as a lining in mastoid cavities. The collagen composition may also be used as a lining tissue in neovaginoplasty. In cardiovascular surgery, the collagen composition may be used as a pericardial closure material. The collagen composition may also be used in the completion of anastomosis in vasovasostomy.

6.73. Uses of the Composition Comprising Stem Cells

In the context of any of the uses described above, whether cosmetic or non-cosmetic, the composition can comprise one or more types of stem cells, preferably placental stem cells, as described above in Section 5.6, above. Placental stem cells, when contacted with a composition of the invention, secrete cytokines that promote wound healing, e.g., IL-6, IL-8 and MCP-1 (monocyte chemotactic protein-1). In embodiments in which the composition of the invention comprises no, or negligible amounts of, fibronectin, the placental stem cells secrete extracellular matrix proteins, including fibronectin, when allowed to attach to the composition. Thus, the composition, in combination with placental stem cells attached to the composition, can act to create a surface or conduit that stimulates, and allows for, cell migration, e.g., into or along a part of an individual receiving the combination.

The composition and stem cells can be administered to an individual together. For example, in one embodiment, the composition can comprise stem cells that have been contacted with the composition immediately prior (e.g., within 10-20 minutes) of administering the composition to the individual. In another embodiment, the stem cells can be contacted with the composition at a time prior to administration sufficient to allow the stem cells to attach to the composition, typically at least 1 hour prior to administration. In a more specific embodiment, the time prior to administration is a time sufficient for the stem cells to attach and proliferate, typically at least 24 hours to 48 hours, or more, prior to administration. In another more specific embodiment, the time is a time sufficient for the stem cells to attach to, and proliferate on, the composition of the invention, and to deposit a detectable amount of an extracellular matrix protein, e.g., fibronectin.

The composition and stem cells can be administered to the individual separately, as well. For instance, in one embodiment, the composition can be administered to an individual, e.g., at the site of a wound or tissue needing repair, and the stem cells can be subsequently administered. In another embodiment, the stem cells are contacted with the site of a wound or tissue needing repair, and the wound or tissue needing repair is subsequently contacted with a composition of the invention.

In one embodiment, therefore, the invention provides a method of promoting the healing of a wound, comprising contacting the wound with a composition of the invention comprising stem cells, e.g., placental stem cells, wherein the stem cells secrete IL-6, IL-8 or MCP-1, or a any combination thereof, or secrete fibronectin, into at least a portion of the wound. Where the stem cells are to secrete fibronectin, it is preferred that the collagen composition of the invention comprise an undetectable amount of fibronectin. In a specific embodiment, the composition is shaped or formed approximately to the shape of the wound. In certain embodiments, the wound is a non-healing wound. In specific embodiments, the wound is a leg ulcer, e.g., a venous leg ulcer, arterial leg ulcer, diabetic leg ulcer or decubitus (pressure) ulcer. Where the wound is a leg ulcer, the composition is preferably formed into a sheet large enough to cover at least a portion of the ulcer, and the sheet comprises placental stem cells on at least the face of the sheet that is to contact the ulcer. In various embodiments, the wound is an accidental wound, or is a wound caused by, or adjunct to, a surgical procedure. The surgical procedure can be any surgical procedure for which the collagen composition of the invention is useful, as discussed above, and can be cosmetic surgery or non-cosmetic surgery.

In another embodiment, the invention promotes the improvement or healing of a defect in a part of the body of an individual. Such a defect can be a naturally-occurring, e.g., genetic, defect such as a fistula, defective heart valve, perforation of the abdominal wall, and the like.

6.8 Kits Comprising the Collagen Compositions

In another aspect the present invention provides kits comprising the collagen compositions of the invention. For example, the present invention provides kits for augmenting or replacing tissue of a mammal. The kits comprise one or more collagen compositions of the invention in a package for distribution to a practitioner of skill in the art. The kits can comprise a label or labeling with instructions on using the collagen composition for augmenting or replacing tissue of a mammal according to the methods of the invention. In certain embodiments, the kits can comprise components useful for carrying out the methods such as means for administering a collagen composition such as one or more syringes, canulas, catheters, etc. In certain embodiments, the kits can comprise components useful for the safe disposal of means for administering the collagen composition (e.g. a 'sharps' container for used syringes). In certain embodiments, the kits can comprise composition in pre-filled syringes, unit-dose or unit-of-use packages.

In certain other embodiments, kits of the invention can comprise a collagen composition of the invention and one or more other components for the culture of a population of stem cells. For example, the kit can comprise a collagen composition of the invention in one or more configurations suitable for the culture of stem cells, e.g., placental stem cells, e.g., a collagen composition in the form of a sheet, tube, mesh, and the like. The kit can comprise one or more items to be used for the culture of stem cells, e.g., culture dishes that are able to contain the collagen composition of the invention during cell culture; plasticware, syringes, pipet tips, cell culture media, one or more cytokines or growth factors, disposables, and the like.

In other embodiments, the kit can comprise one or more components that facilitate the collection of stem cells from placental tissue. In various specific embodiments, the kit comprises components that facilitate perfusion of a placenta to collect stem cells, e.g., perfusion solution; one or more trays large enough to contain a placenta, glassware or plasticware for collection of perfusion solution; one or more bags for collection of perfusion solution, needs and/or canulae for canalizing umbilical vessels; and the like. In other specific embodiments, the kit comprises one or more components that facilitate enzymatic digestion of placental tissue to isolate placental stem cells, e.g., one or more tissue-digesting enzymes (e.g., trypsin, chymotrypsin, or the like); plasticware suitable for cell culture (e.g., culture dishes, multiwell culture plates, and the like).

In certain embodiments, the kit comprises instructions for the use of the collagen composition of the invention in at least one medical context, e.g., wound healing. In other embodiments, the kit comprises instructions for the culture of one or more populations of stem cells on a collagen composition of the invention.

7. EXAMPLES

In the sections below, those of skill in the art will recognize that the phrase "at approximately 23° C." can refer to room temperature.

7.1 Example 1: Isolation of Collagen from Placentas

This example illustrates isolation of collagen from placentas.

Frozen placentas are obtained according to the methods described herein. The placentas are thawed by wrapping in a Nalgene tray with water for 1-4 hrs. They are then removed from plastic wrap and placed in water for further thawing.

Thawed placentas are placed on the stainless steel tray of a meat grinder. The umbilical cord fragment is cut from each placenta, and each placenta is sliced into about 4 strips at approximately 23° C. The strips are ground with the meat grinder at approximately 23° C.

Osmotic Shock: The resulting ground placentas are added to a Nalgene tank with 0.5 M NaCl (5 liters/placenta) and mixed using a motorized mixer at 75-100 rpm (24 hrs at 4-6° C.).

After 24 hrs, the mixer is stopped, allowing tissue to settle to the bottom of the mixer at approximately 23° C. Tissue and fluid are pumped out using a peristaltic pump with #36 TYGON® tubing and filtered through a #40 sieve at approximately 23° C., and isolated tissue is placed back into the mixing tank.

Fresh 0.5 M NaCl (5 L/placenta) is added to the mixture and mixed for 24 hrs at 4-6° C. (motorized mixer, 75-100 rpm). After 24 hrs, the tissue is isolated using the method described above.

Tissue is washed with water (5 L/placenta) and mixed for 24 hrs at 4-6° C. (motorized mixer, 75-100 rpm). After 24 hrs, the tissue is isolated using the method described above.

The tissue is further washed again with 0.5 M NaCl, again with 0.5 M NaCl and then water according to the above four paragraphs.

Freeze-drying: The resulting sample is shelled in 200-400 g amounts in a freeze-dryer vessel and frozen at −70° C. for 1-2 hrs. The frozen sample is freeze-dried for 24-48 his in a freeze-drier and then removed. The freeze-dried sample is mixed to a smooth powder in a blender and then transferred to a clean mixing tank.

Detergent treatment: A 1% deoxycholic acid solution (1 L/placenta) is added to the mixing tank with the blended, freeze-dried sample. The sample and 1% deoxycholic acid solution are mixed for 24 hrs at 4-6° C. (motorized mixer, 75-100 rpm). After 24 hrs, the mixer is stopped, and tissue is isolated with a #40 sieve as described above.

The detergent treatment is repeated for 24 hrs at 4-6° C. (motorized mixer, 75-100 rpm). After 24 hrs, the mixer is stopped, and tissue is isolated with a #40 sieve as described above.

Water wash: Tissue is washed with water (5 L/placenta) and mixed for 24 hrs at 4-6° C. (motorized mixer, 75-100 rpm). After 24 hrs, the tissue is isolated using the method described above.

Tissue is again washed with water (5 L/placenta) and mixed for 24 hrs at 4-6° C. (motorized mixer, 100-150 rpm). After 24 hrs, the tissue is isolated using the method described above.

Tissue is again washed with water (5 L/placenta) and mixed for 24 hrs at 4-6° C. (motorized mixer, 150 rpm). After 24 hrs, the tissue is isolated using the method described above.

Optionally, tissue is washed with water (5 L/placenta) a fourth time and mixed for 24 hrs at 4-6° C. (motorized mixer, 150 rpm). After 24 hrs, the tissue is isolated using the method described above.

Freeze-drying: The resulting sample is added to a blender in 200 g amounts. 200 mL deionized water is added to the sample, and the sample is mixed to a smooth paste with the blender. Blended samples are pooled and rinsed with water (1 L/placenta).

Sample in 200-400 g amounts is added to a freeze-dryer vessel. Samples are shelled and frozen at −70° C. Shelled samples are freeze dried for 24-48 hrs.

Sterile basic treatment: Freeze-dried samples are pooled. Sodium hydroxide solution (0.5 M, 1 L) is added to an autoclaved, sterile flask. Low endotoxin water (1 L) is added to the pooled, freeze-dried samples. The samples and sodium hydroxide solution are mixed on a shaker at 250 rpm for 4 hrs at approximately 23° C.

Sterile water wash: The sample is recovered by filtration through a sterile #70 filter and rinsed with 1 L endotoxin free water. Endotoxin free water (1 L) is added, and sample is mixed on a shaker at 250 rpm for 18-24 hrs at approximately 23° C.

The sample is recovered by filtration through a sterile #70 filter. Endotoxin free water (1 L) is added, and sample is mixed on a shaker at 250 rpm for 18-24 hrs at approximately 23° C.

The sample is recovered by filtration through a sterile #70 filter and rinsed with 1 L endotoxin free water. Endotoxin free water (1 L) is added, and sample is mixed on a shaker at 250 rpm for 18-24 hrs at approximately 23° C.

If the pH is greater than 9, the sample is washed again with endotoxin-free water and mixed on a shaker at about 250 RPM for about 18-24 hours.

If the pH is less than or equal to 9, the sample is ready for formulation.

The yield can be 10 g/placenta or more.

The resulting sample can be freeze-dried for storage. For use, the sample can be suspended in phosphate-buffered saline at 300-1000 mg/mL in a blender for use as a paste in, for example, a syringe. The sample can also be molded in phosphate buffered saline at 500-1000 mg/mL and shaped for use as for example, sheets, tubes, plugs, or the like.

7.2 Example 2: Preparation of Telopeptide Collagen Samples 7.5 g of telopeptide collagen was prepared according to the osmotic shock, freeze-drying, detergent treatment, water wash, freeze-drying, basic treatment, water wash and freeze-drying steps of Example 1.

11.8 g of telopeptide collagen was prepared according to the osmotic shock, freeze-drying, detergent treatment, water wash, basic treatment, water wash and freeze-drying steps of Example 1.

12.0 g of telopeptide collagen was prepared according to the osmotic shock, freeze-drying, detergent treatment, water wash, basic treatment, water wash and freeze-drying steps of Example 1.

11.8 g of telopeptide collagen was prepared according to the osmotic shock, detergent treatment, water wash, basic treatment, water wash and freeze-drying steps of Example 1.

7.3 Example 3: Biochemical Analysis

A collagen sample was prepared according to Examples 1 and 2. Biochemical analysis by standard techniques showed by dry weight 80.40% collagen, 11.00% water and less than 0.01% fibronectin, laminin and glygosoaminoglycans. Elastin content was not determined.

Amino acid analysis of samples prepared according to Examples 1 and 2 showed 34-35% glycine, about 11% hydroxyproline and 10-11% proline.

Immunoanalysis of samples prepared according to Examples 1 and 2 showed 74-92% type I collagen, 4-6% type III collagen and 2-15% type IV collagen.

7.4 Example 4: Alternate Methods of Making ECM, and Culture of Stem Cells on the ECM This Example demonstrates alternate methods of making the collagen composition of the invention, and provides an analysis of the composition of the materials made by those methods.

Materials and Methods

Isolation of Extracellular Matrix (ECM):

The ECM was isolated as follows. Briefly, a frozen human placenta was thawed in 0.5M sodium chloride, ground in a meat grinder and washed repeatedly in 0.5M sodium chloride and water in a incubator shaker at 23° C., followed by a detergent such as 1% SDS or 0.5% deoxycholic acid. Blood-free placental tissue was treated with 0.1-0.5N sodium hydroxide for times varying between 3 hours and 24 hours to solubilize the cotyledonous tissue, following by rinsing with phosphate-buffered saline (PBS) to neutralize the pH. The material produced as such was a stable paste and was stored at 4° C.

Biochemical Analysis:

To determine the biochemical composition of the isolated ECM, a 1 gram sample was freeze-dried and dry weight determined. The ECM was solubilized by either dissolving in 100 mM HCl at 70° C. or by pepsin treatment (1 mg/gm) of the ECM in 10 mM HCl at 23° C. for 18 hrs. The tissue dissolved in 100 mM HCl was used to determine content of fibronectin, laminin, GAGs and elastin. The pepsin-solubilized tissue was used to determine collagen content.

Fibronectin and laminin concentrations were determined using a sandwich ELISA. Elastin and glycosaminoglycan (GAG) content were determined using a dye based assay. For Determination of collagen I content was performed using a sandwich ELISA (Chondrex). Collagen III and IV content were determined using in-house ELISAs using primary antibodies for Type II and Type IV collagen and HRP-conjugated secondary antibodies.

Preparation of ECM Constructs:

To prepare sheets of the ECM material, a layer of hydrated ECM paste was sandwiched between two medical grade TYVEK® sheets. This construct was loaded into a gel drier and vacuum was applied overnight at 23° C. until the ECM film was dry. Sheets were cut to an appropriate size for cell culture studies. To prepare 3D structures of the ECM, the ECM paste was filled into various molds and freeze-dried. To study the stability of the ECM sheets and 3D molds in media or water. The constructs were incubated at 37° C. up to 1 week, in water, saline or cell culture media.

Cell Culture:

Placental stem cells were subcultured in 60% low-glucose DMEM (Invitrogen, Carlsbad, Calif.), 40% MCDB-201 (Sigma, St. Louis, Mo.), 2% fetal bovine serum (Hyclone, Logan, Utah), 1× insulin-transferrin-selenium supplement (Invitrogen), 0.02% linoleic acid/bovine serum albumin (Sigma), 10 ng/mL epidermal growth factor (Sigma), 10 ng/mL platelet-derived growth factor (R&D Systems, Minneapolis, Minn.), 0.05M dexamethasone (Sigma), 0.1 m M ascorbic acid 2-phosphate (Sigma), and 100 U penicillin/ 1000 U streptomycin (Invitrogen). Placental stem cells (30,000 per well) were seeded onto ECM films that had been positioned into 24 multi-well cluster plates. Placental stem cells were also seeded at equivalent density on Labtek chamber slides (Nalgene Nunc International, Rochester, N.Y.) pre-coated with collagen (Inamed, Fremont, Calif.). Cells were incubated at 37° C. for 3 and 48 hours and processed for immunofluorescence microscopy.

Immunofluorescence Microscopy:

After 3 or 48 hr incubation with ECM films, placental stem cell-ECM constructs were fixed with 3.7% formaldehyde for 10 minutes and permeabilized with 0.5% Triton-X 100 for 20 minutes. Placental stem cells were incubated with AlexaFluor 488-conjugated phalloidin to visualize F-actin. For fibronectin staining, samples incubated with a rabbit anti-human fibronectin antibody (Sigma) in blocking buffer (3% bovine serum albumin/1× phosphate-buffered saline) for 1 hour, washed with phosphate-buffered saline, and further incubated with the AlexaFluor 594-conjugated anti-rabbit antibody in blocking buffer for 30 minutes. Samples were again washed with phosphate-buffered saline, mounted on slides, and observed with a fluorescent microscope.

Cytokine Secretion Analysis:

Media samples (100 μl) were removed from cell cultures ECM sheets containing placental stem cells, as well as from tissue culture treated plates containing placental stem cell, at 0, 3, 24 and 48 hrs of culture. Samples were diluted into 1 mL PBS and analyzed for the presence of cytokines. Concentration of each cytokine was calculated from a standard plot of known concentrations of cytokines.

Results

Isolation of ECM:

The dry weight of a typical placenta is about 30 g, corresponding to a wet weight of about 300 g per placenta. As shown in FIG. 1, the osmotic shock step and detergent washing step can be used to remove a considerable amount of non-extracellular matrix tissue, with a final residual weight of about 10 g. The use of a combination of solubilization using NaOH and detergent results in a further decrease in the residual weight to about 6 g. It was found that the time of exposure to NaOH, and the concentration of NaOH, affected the total mass of ECM isolated from the placenta. Variations of our detergent and NaOH wash steps were used to generate 5 variations of the final ECM material. Typically, a single placenta yielded between about 6 g to about 10 g of ECM material.

Biochemical Composition of ECM:

Biochemical analysis of the 5 variations of the ECMs showed that they were composed essentially of collagens; Type I being the major collagen (about 74% to about 90% of total collagen), and Type III (about 4% to about 6% of total collagen) and Type IV (about 2% to about 15% of total collagen) being minor components. The other major extracellular matrix protein found in the placental ECM was elastin. As shown in Table 1, elastin represented about 3-5% of the total dry weight of ECM-1 to ECM-4. However, ECM-5, which was generated without the use of NaOH, contained approximately 12% elastin. While glycosaminoglycans were identified in ECM material made by all five methods, % dry weight appeared to be unaffected by the use of NaOH in the isolation methods. The presence of the important adhesion proteins fibronectin and laminin, conversely, was dramatically sensitive to the use of NaOH. Fibronectin and laminin did not survive the NaOH treatment, and could not be found in ECMs 1 through 4. However, ECM-5, which was isolated without the use of NaOH, has a composition that is richer in the adhesion proteins (Table 1).

TABLE 1

Extracellular matrix components present in placental collagen compositions made by different methods.

| | Fibronectin | Laminin | GAGs | Elastin |
|---|---|---|---|---|
| ECM-5 | 0.6% | 0.16% | 0.40% | 12% |
| ECM-4 | 0 | 0 | 0.28% | 4.7% |
| ECM-3 | 0 | 0 | 0.34% | 3.2% |
| ECM-2 | 0 | 0 | 0.38% | 4.4% |
| ECM-1 | 0 | 0 | 0.59% | 3.5% |

% = percent dry weight

Cell Binding Studies:

Three hours after seeding, similar levels of attachment of placental stem cells were observed on all ECMs (#1-5). The levels of stem cell binding to ECMs were slightly less than that observed on purified collagen. Immunostaining for fibronectin at this time revealed abundant intracellular staining, with no detectable extracellular fibronectin. By 48 hours of culture, placental stem cells were observed to increase in number and to adopt similar well-spread morphologies on purified collagen, ECM2, and ECM4. In contrast, placental stem cells cultured on ECM1 did not thrive. Not only were fewer cells observed, but their morphologies were rounded and not well-spread. Placental stem cells on ECM5 appeared more elongated and polarized than placental stem cells on other ECMs or on collagen.

Determination of cell attachment on ECM3 was somewhat compromised due to the heterogeneity of the surface of the material upon drying. Because it was difficult to image along one plane of focus, it initially appeared that very few cells attached; however observation in different planes of focus revealed some cell attachment on ECM3.

Immunostaining for fibronectin at the 48 hr timepoint revealed an extensive network of extracellular fibronectin matrix fibrils on ECM1-ECM4. These fibronectin matrix fibrils were assembled by placental stem cells, as controls in which placental stem cells were not cultured on ECM did not show evidence of fibronectin fibrils. In contrast to ECM1-ECM4, ECM5 and collagen did not support fibronectin matrix assembly by placental stem cells; no extracellular fibrillar fibronectin was detected on these surfaces.

Cytokine Array Studies:

We investigated the secretion of key cytokines/chemokines from the placental stem cells as a consequence of binding and proliferation on the ECM. Cytokine secretion on ECM was compared to that from placental stem cells incubated on tissue culture treated cell culture plates. A standard a 25-multiplex cytokine array, which includes several interleukins and cytokines (Biosource), was used. The cytokines included IL-1β, IL-1Ra, IL-2R, IL-4, IL-5, IL-6, IL-7, IL-8, IL-10, IL-12p40/p70, IL-13, IL-15, IL-17, TNF-α, IFN-α, IFN-γ, GM-CSF, MIP-1α, MIP-1β, IP-10, MIG, Eotaxin, Rantes, and MCP-1. Of the 25 cytokines studied, increased secretion of 3 cytokines, IL-6, IL-8 and MCP-1 were observed when placental stem cells were cultured on the ECM sheets, over and above secretion by placental stem cells cultured on tissue culture treated plates. FIGS. 2A-2C show a time-dependent increase in cytokine secretion (IL-6, IL-8 & MCP-1) by placental stem cells on the five ECM constructs. All data was normalized for 1000 cells bound/cm$^2$. ECM-5 was anomalous in that there was no apparent increase in MCP-1 secretion, suggesting a change in cellular physiology of the placental stem cells when cultured on this extra-cellular matrix. As previously shown, ECM-5 did not support the expression of fibronectin, quite unlike ECM-1 through-4. It is interesting to note that ECM-5 was the only matrix generated without the use of NaOH and had a biochemical composition that maintained the 2 key cell adhesion proteins fibronectin and laminin.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A composition comprising placental extracellular matrix, wherein said composition comprises at least 80% collagen by dry weight, wherein said collagen comprises (i) between 74% and 90% Type I collagen, between 4% to 6% Type III collagen, and between 2% to 15% type IV collagen, (ii) no detectable amounts of fibronectin or laminin, and (iii) additional extracellular matrix components selected from the following groups:
   (a) 4.7% elastin by dry weight and 0.28% glycosaminoglycans by dry weight;
   (b) 3.2% elastin by dry weight and 0.34% glycosaminoglycans by dry weight;
   (c) 4.4% elastin by dry weight and 0.38% glycosaminoglycans by dry weight; and
   (d) 3.5% elastin by dry weight and 0.59% glycosaminoglycans by dry weight.

2. The composition of claim 1, wherein said placental collagen is human placental collagen.

3. The composition of claim 1, wherein said composition is shaped as a sheet.

4. The composition of claim 1, wherein said composition is shaped to fit to a site of a wound or injury.

5. The composition of claim 1, wherein said composition is formulated as a gel, a cream, a paste, a spray, an aerosol, or a solution.

6. The composition of claim 1, wherein said composition comprises a pharmacologically active agent.

7. The composition of claim 6, wherein said pharmacologically active agent comprises platelet-derived growth factor, insulin-like growth factor, epidermal growth factor, transforming growth factor beta, an angiogenesis factor, an antibiotic, an antifungal agent, a spermicidal agent, a hormone, an enzyme, or an enzyme inhibitor.

8. The composition of claim 1, wherein said composition is prepared by performing the following steps, in order:
   a. macerating placental tissue;
   b. suspending the tissue in an osmotic shock solution;
   c. suspending the tissue in a solution that comprises detergent; and
   d. washing the tissue.

9. The composition of claim 1, wherein the composition further comprises placental stem cells that are allogeneic to the subject.

10. The composition of claim 1, wherein the composition further comprises placental stem cells that are autologous to the subject.

11. The composition of claim 8, wherein the detergent comprises deoxycholate.

12. A method of treating a wound or burn of a subject comprising contacting the wound or burn with the composition of claim 1.

13. The method of claim 12, wherein said composition is used as a wound filler.

14. The method of claim 12, wherein said composition is applied directly to the site of the wound or burn.

15. A method of augmenting the skin of a subject in an area of the subject in need of augmenting, wherein said method comprises administering the composition of claim 1 to said area.

16. The method of claim 15, wherein said composition is administered by injection.

17. The method of claim 15, wherein said composition is administered to augment skin that requires augmentation as a result aging, trauma, disease, sickness, environmental factors, weight loss, or child birth.

18. The method of claim 15, wherein said composition is administered to augment skin that comprises wrinkles, frown lines, worry lines, crow's feet, marionette lines, stretch marks, or scars.

* * * * *